(12) United States Patent
Savage

(10) Patent No.: US 7,521,197 B2
(45) Date of Patent: *Apr. 21, 2009

(54) METHOD FOR PRODUCING CYTOTOXIC T-CELLS

(75) Inventor: Philip Michael Savage, London (GB)

(73) Assignee: Alexis Biotech Limited, London (GB)

( * ) Notice: Subject to any disclaimer, the term of this patent is extended or adjusted under 35 U.S.C. 154(b) by 536 days.

This patent is subject to a terminal disclaimer.

(21) Appl. No.: 10/308,543

(22) Filed: Dec. 3, 2002

(65) Prior Publication Data

US 2004/0096429 A1 May 20, 2004

Related U.S. Application Data

(63) Continuation-in-part of application No. 10/116,901, filed on Apr. 5, 2002, now Pat. No. 7,264,965, which is a continuation-in-part of application No. 09/878,158, filed on Jun. 8, 2001, which is a continuation-in-part of application No. 09/724,985, filed on Nov. 28, 2000, now Pat. No. 7,268,219, and a continuation-in-part of application No. PCT/GB99/01764, filed on Jun. 4, 1999, application No. 10/308,543, which is a continuation-in-part of application No. 09/878,158, filed on Jun. 8, 2001, and a continuation-in-part of application No. 09/724,985, filed on Nov. 28, 2000, now Pat. No. 7,268,219.

(30) Foreign Application Priority Data

| Jun. 5, 1998 | (GB) | ................................ 9812227.8 |
| Apr. 12, 1999 | (GB) | ................................ 9908333.9 |

(51) Int. Cl.
C12N 5/16 (2006.01)
C07K 16/00 (2006.01)

(52) U.S. Cl. ....................... 435/7.24; 435/373; 435/375

(58) Field of Classification Search ....................... None
See application file for complete search history.

(56) References Cited

U.S. PATENT DOCUMENTS

| 5,026,785 | A | 6/1991 | Mage et al. |
| 5,662,907 | A | 9/1997 | Kubo et al. |
| 6,475,483 | B1 | 11/2002 | Steinman et al. |
| 6,548,067 | B1 | 4/2003 | Seeman et al. |
| 7,264,965 | B2 * | 9/2007 | Savage ......................... 435/325 |

FOREIGN PATENT DOCUMENTS

| EP | 0 352 761 A | 1/1990 |
| WO | WO 93/10220 | 5/1993 |
| WO | WO 95/04817 A1 * | 2/1995 |
| WO | WO 96/04314 A1 | 2/1996 |
| WO | WO 97/24446 A2 | 7/1997 |
| WO | WO 98/03552 | 1/1998 |
| WO | WO 99/11775 A1 | 3/1999 |
| WO | WO 99/13095 A2 | 3/1999 |
| WO | WO 99/64464 A2 | 12/1999 |

OTHER PUBLICATIONS

Schultz et al (Cancer Res. 60: 6663-6669, 2000).*
Marti et al (Ann. NY Acad. Sci. 651: 480-483, 1992).*
Kageyama et al (J. Immunol. 154: 567-576, 1995).*
Schade et al (J. Allergy Clin. Immunol. 106: 1155-62, 2000).*
Oka et al (J. Immunol. 164: 1873-1880, 2000).*
Huang, J.H. et al., "Protein transfer of preformed MHC-peptide complexes sensitizes target cells to T cell cytolysis," Immunity, 1(7): 607-13, 1994.
Moris, A. et al., "Cutting Edge: Characterization of Allorestricted and Peptide-Selective Alloreactive T Cells Using HLA-Tetramer Selection", The Journal of Immunology, 166: 4818-4821, 2001.
Ogg, G.S. et al., "Sensitization of tumor cells to lysis by virus-specific CTL using antibody-targeted MHC/peptide complexes," British Journal of Cancer, 82(5): 1058-62, 2000.
Sadovnikova, E. et al., "Generation of human tumor-reactive cytotoxic T cells against peptides presented by non-self HLA molecules", Eur. J. Immunol., 28: 193-200, 1998.
Moris et al, "Cutting Edge: Characterization of Allorestricted and Peptide-Selective Alloreactive T Cells Using HLA-Tetramer Selection", The American Association of Immunologists, p. 4818-4821, 2001, vol. 166.
Sadovnikova et al., "Generation of human tumor-reactive cytotoxic T cells against peptides presented by non-self HLA molecules", Eur. J. Immunol., 28: pp. 193-200, 1998.
Dario Neri et al., "Recombinant Anti-Human Melanoma Antibodies Are Versatile Molecules", The Society For Investigative Dermatology. Inc., 1996, vol. 107, No. 2, pp. 164-170.
Guido Ferrari, et al., "Absence of Immunodominant Anti-Gag p17 (SL9) Responses among Gag CTL-Positive, HIV-Uninfected Vaccine Recipients Expressing the HLA-A*0201 Allele", The Journal of Immunology, 2004, vol. 173, pp. 2126-2133.
Andrew J. Dannenberg et al., "Cyclooxygenase-2 and Epidermal Growth Factor Receptor: Pharmacologic Targets for Chemoprevention", Abstract of Journal of Clinical Oncology, 2005, vol. 23, No. 2, pp. 254-266.
J.L. Xing et al., "Multiple Sclerosis: Characters of magnetic resonance imaging of optic nerve and spinal cord and the new method of intervention", Abstract of Chinese Journal of Clinical Rehabilitation, 2005, vol. 9, No. 9, pp. 151-153.

(Continued)

Primary Examiner—Michael Szperka
Assistant Examiner—DiBrino Marianne
(74) Attorney, Agent, or Firm—Frommer Lawrence & Haug LLP; Thomas J. Kowalski

(57) ABSTRACT

The invention relates to the method for producing antipeptide cytotoxic T lymphocytes (CTLs) by attaching a complex of a class I HLA and a peptide to antigen presenting cell(s) (APCs) present in a sample of peripheral blood lymphocytes (PBLs), optionally removing excess class I HLA/peptide complex, and incubating with proliferative cytokine. The invention further relates to a CTL obtainable by these methods and to a method of treating a subject by administering such a CTL to the subject.

9 Claims, 34 Drawing Sheets

OTHER PUBLICATIONS

Michal Schwartz et al., "Multiple Sclerosis as a By-Product of the Failure to Sustain Protective Autoimmunity: A Paradigm Shift", The Neuroscientist, 2002, vol. 8, No. 5, pp. 405-413.

J. L. Fahey et al., Status of Immune-Based Therapies in HIV Infection and AIDS, Clin. Exper. Immunol., 1992, vol. 88, pp. 1-5.

Norman L. Letvin et al., "Progress in the Development of an HIV-1 Vaccine", Science, 1998, vol. 280, pp. 1875-1880.

Ana Machuca et al., "Human Immunodeficiency Virus Type 2 Infection in Spain", Intervirology, 1999, vol. 42, pp. 37-42.

Ping Gao, et al., "Tumor Vaccination That Enhances Antitumor T-Cell Responses Does Not Inhibit the Growth of Established Tumors Even in Combination With Interleukin-12 Treatment: The Importance of Inducing Intratumoral T-Cell Migration", Journal of Immunotherapy, 2000, vol. 23, No. 6, pp. 643-653.

Xiaoqiang Kang et al., "Induction of Melanoma Reactive T Cells by Stimulator Cells Expressing Melanoma Epitope-Major Histocompatibility Complex Fusion Proteins", Cancer Research, 1997, vol. 57, pp. 202-205.

Alison T. Stopeck et al., "Phase I Study of Direct Gene Transfer of an Allogeneic Histocompatibility Antigen, HLA-B7, in Patients With Metastatic Melanoma", Journal of Clinical Oncology, 1997, vol. 15, No. 1, pp. 341-349.

David N. Garboczi et al., "HLA-A2-peptide complexes: Refolding and crystallilzation of molecules expressed in *Escherichia coli* and complexed with single antigen peptides", Proc. Natl. Acad. Sci., 1992, vol. 89, pp. 3429-3433.

Gert Riethmüller et al., "Monoclonal antibodies in the detection and therapy of micrometastatic epithelial cancers", Current Opinion in Immunology, 1992, vol. 4, pp. 647-655.

G.L. Buraggi et al., "Imaging with [131]I-Labeled Monoclonal Antibodies to a High-Molecular-Weight Melanoma-associated Antigen in patients with Melanoma: Efficacy of Whole Immunoglobulin and Its F(ab')$_2$ Fragments[1]" Cancer Research, 1985, vol. 45, pp. 3378-3387.

D.G. Maloney, "Phase I clinical trial using escalating single-dose infusion of chimeric anti-CD20 monoclonal antibody (IDEC-C2B8) in patients with recurrent B-cell Iymphoma", Blood, 1994, vol. 84, pp. 2457-2466.

Gert Riethmüller et al., "Randomised trial of monoclonal antibody for adjuvant therapy of resected Dukes' C colorectal carcinoma", The Lancet, 1994. vol. 343, pp. 1177-1183.

V. Hird et al., "Adjuvant therapy of ovarian cancer with radioactive monoclonal antibody", Br. J. Cancer, 1993, vol. 68, pp. 403-406.

Monica Moro et al., "Tumor Cell Targeting with Antibody-Avidin Complexes and Biotinylated Tumor Necrosis Factor $\alpha$[1]", Cancer Research, 1997, vol. 57, pp. 1922-1928.

John D. Altman et al., "Phenotypic Analysis of Antigen-Specific T Lymphoncytes", Science, 1996, vol. 274, pp. 94-96.

Peter Brossart et al., "Her-2/neu-derived Peptides Are Tumor-associated Antigens Expressed by Human Renal Cell and Colon Carcinoma Lines and Are Recognized by in Vitro Induced Specific Cytotoxic T Lymphocytes[1]", Cancer Research, 1998, vol. 58, pp. 732-736.

Sophie Lucas et al., "Identification of a New *MAGE* Gene with Tumor-specific Expression by Representational Difference Analysis", Cancer Research, 1998, vol. 58, pp. 743-752.

Srisin Khusmith et al., "Protection Against Malaria by Vaccination with Sporozoite Surface Protein 2 Plus CS Protein", Science, 1991, vol. 252, pp. 715-718.

Mikael Dohlsten et al., "Superantigen-Induced Cytokines Suppress Growth of Human Colon-Carcinoma Cells", Int. J. Cancer, 1993, vol. 54, pp. 482-488.

J.A. Ledermann et al., "A Phase-I Study of Repeated Therapy With Radiolabelled Antibody To Carcinoembryonic Antigen Using Intermittent or Continuous Administration of Cyclosporin a to Suppress the Immune Response", Int. J. Cancer, 1991, vol. 47, pp. 659-664.

Edward A. Bayer et al., "Protein Biotinylation", Methods in Enzymology, 1990, vol. 184, pp. 138-160.

R. Paul Johnson et al., "HIV-1 gag-Specific Sytotoxic T Lymphocytes Recognize Multiple Highly Conserved Epitopes", The Journal of Immunology, 1991, vol. 147, No. 5, pp. 1512-1521.

Jesus Santos-Aguado et al., "Molecular Characterization of Serologic Recognition Sites in the Human HLA-A2 Molecule", The Journal of Immunology, 1988, vol. 141, pp. 2811-2818.

Graham S. Ogg et al., "Quantitation of HIV-1-Specific Cytotoxic T Lymphocytes and Plasma Load of Viral RNA", Science, 1998, vol. 278, pp. 2103-2106.

Kenneth C. Parker et al., "Sequence Motifs Important for Peptide Binding to the Human MHC Molecule HLA-A2", The Journal of Immunology, 1992, vol. 149, pp. 3580-3587.

Pedro Romero et al., "Cytolytic T Lymphocyte Recognition of the Immunodominant HLA-A*0201-Restricted Melan-A/MART-1 Antigen Peptide in Melanoma", The American Association of Immunologists, 1997, vol. 159, pp. 2366-2374.

R.J. Berenson et al., "Elimination of Daudi lymphoblasts from human bone marrow using avidinbiotin immunoadsorption", Blood, 1986, vol. 67, pp. 509-515.

George S. Eisenbarth et al., "Production of Monoclonal Antibodies Reacting with Peripheral Blood Mononuclear Cell Surface Differentiation Antigens", The Journal of Immunology, 1980, vol. 124, No. 3, pp. 1237-1244.

\* cited by examiner

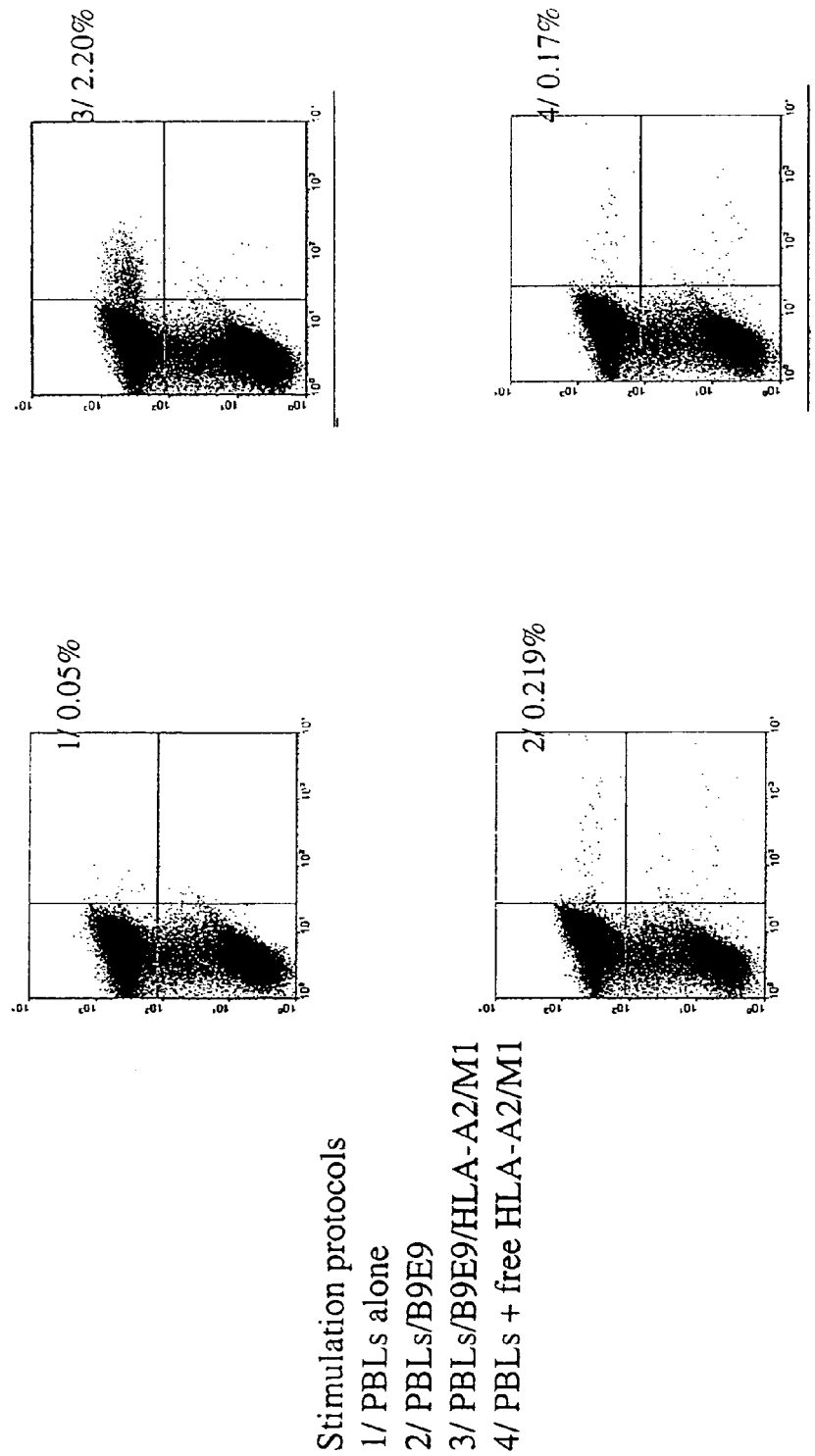

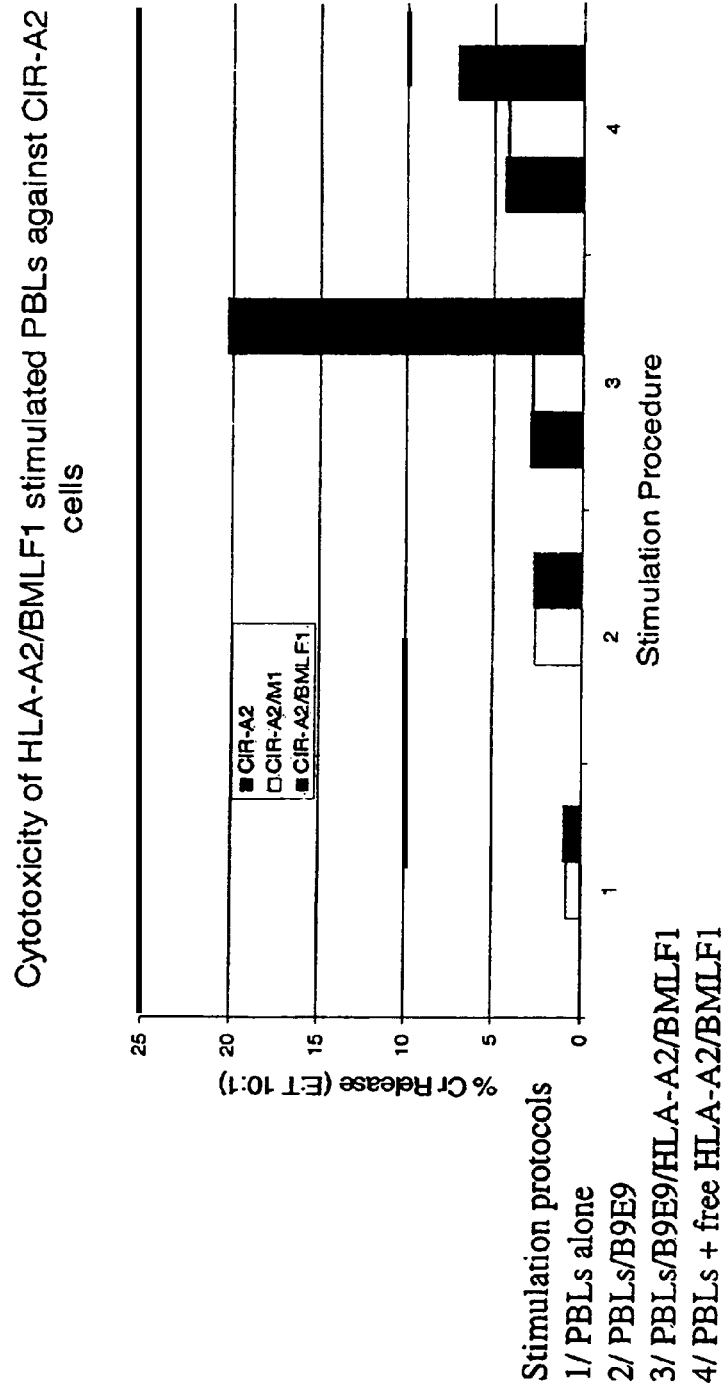

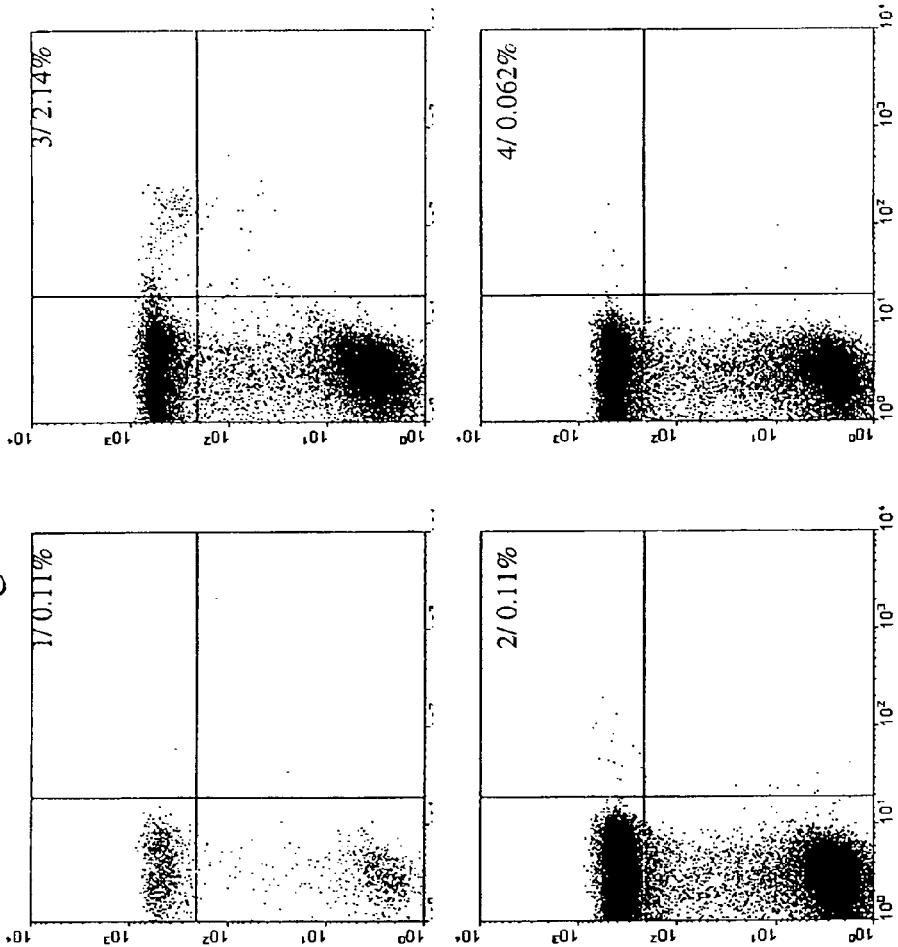

SEQUENCE LISTING

```
<160> NUMBER OF SEQ ID NOS: 177

<210> SEQ ID NO 1
<211> LENGTH: 8
<212> TYPE: PRT
<213> ORGANISM: Epstein-Barr virus

<400> SEQUENCE: 1
```

Arg Ala Lys Phe Phe Gln Leu Leu
1               5

<210> SEQ ID NO 2
<211> LENGTH: 9
<212> TYPE: PRT
<213> ORGANISM: Homo sapiens

<400> SEQUENCE: 2

Ser Leu Tyr Asn Thr Val Ala Thr Leu
1               5

<210> SEQ ID NO 3
<211> LENGTH: 10
<212> TYPE: PRT
<213> ORGANISM: Homo sapiens

<400> SEQUENCE: 3

Glu Ala Ala Gly Ile Gly Ile Leu Thr Val
1               5                   10

<210> SEQ ID NO 4
<211> LENGTH: 9
<212> TYPE: PRT
<213> ORGANISM: Influenza virus

<400> SEQUENCE: 4

Gly Ile Leu Gly Phe Val Phe Thr Leu
1               5

<210> SEQ ID NO 5
<211> LENGTH: 9
<212> TYPE: PRT
<213> ORGANISM: Epstein-Barr virus

<400> SEQUENCE: 5

Gly Leu Cys Thr Leu Val Ala Met Leu
1               5

<210> SEQ ID NO 6
<211> LENGTH: 10
<212> TYPE: PRT
<213> ORGANISM: Homo sapiens

<400> SEQUENCE: 6

Glu Leu Ala Gly Ile Gly Ile Leu Thr Val
1               5                   10

<210> SEQ ID NO 7
<211> LENGTH: 9
<212> TYPE: PRT
<213> ORGANISM: Homo sapiens

<400> SEQUENCE: 7

Glu Ala Asp Pro Thr Gly His Ser Tyr
1               5

<210> SEQ ID NO 8
<211> LENGTH: 9
<212> TYPE: PRT
<213> ORGANISM: Homo sapiens

<400> SEQUENCE: 8

Ser Leu Phe Arg Ala Val Ile Thr Lys

```
1               5

<210> SEQ ID NO 9
<211> LENGTH: 9
<212> TYPE: PRT
<213> ORGANISM: Homo Sapiens

<400> SEQUENCE: 9

Asn Tyr Lys His Cys Phe Pro Glu Ile
1               5

<210> SEQ ID NO 10
<211> LENGTH: 10
<212> TYPE: PRT
<213> ORGANISM: Homo sapiens

<400> SEQUENCE: 10

Glu Val Tyr Asp Gly Arg Glu His Ser Ala
1               5                   10

<210> SEQ ID NO 11
<211> LENGTH: 10
<212> TYPE: PRT
<213> ORGANISM: Homo sapiens

<400> SEQUENCE: 11

Arg Glu Pro Val Thr Lys Ala Glu Met Leu
1               5                   10

<210> SEQ ID NO 12
<211> LENGTH: 9
<212> TYPE: PRT
<213> ORGANISM: Homo sapiens

<400> SEQUENCE: 12

Asp Pro Ala Arg Tyr Glu Phe Leu Trp
1               5

<210> SEQ ID NO 13
<211> LENGTH: 9
<212> TYPE: PRT
<213> ORGANISM: Homo sapiens

<400> SEQUENCE: 13

Ser Ala Phe Pro Thr Thr Ile Asn Phe
1               5

<210> SEQ ID NO 14
<211> LENGTH: 9
<212> TYPE: PRT
<213> ORGANISM: Homo sapiens

<400> SEQUENCE: 14

Ser Ala Tyr Gly Glu Pro Arg Lys Leu
1               5

<210> SEQ ID NO 15
<211> LENGTH: 9
<212> TYPE: PRT
<213> ORGANISM: Homo sapiens

<400> SEQUENCE: 15

Ser Ala Tyr Gly Glu Pro Arg Lys Leu
1               5
```

```
<210> SEQ ID NO 16
<211> LENGTH: 9
<212> TYPE: PRT
<213> ORGANISM: Homo sapiens

<400> SEQUENCE: 16

Lys Met Val Glu Leu Val His Phe Leu
1               5

<210> SEQ ID NO 17
<211> LENGTH: 9
<212> TYPE: PRT
<213> ORGANISM: Homo sapiens

<400> SEQUENCE: 17

Lys Met Val Glu Leu Val His Phe Leu
1               5

<210> SEQ ID NO 18
<211> LENGTH: 9
<212> TYPE: PRT
<213> ORGANISM: Homo sapiens

<400> SEQUENCE: 18

Glu Tyr Leu Gln Leu Val Phe Gly Ile
1               5

<210> SEQ ID NO 19
<211> LENGTH: 9
<212> TYPE: PRT
<213> ORGANISM: Homo sapiens

<400> SEQUENCE: 19

Glu Val Asp Pro Ile Gly His Leu Tyr
1               5

<210> SEQ ID NO 20
<211> LENGTH: 9
<212> TYPE: PRT
<213> ORGANISM: Homo sapiens

<400> SEQUENCE: 20

Phe Leu Trp Gly Pro Arg Ala Leu Val
1               5

<210> SEQ ID NO 21
<211> LENGTH: 9
<212> TYPE: PRT
<213> ORGANISM: Homo sapiens

<400> SEQUENCE: 21

Thr Phe Pro Asp Leu Glu Ser Glu Phe
1               5

<210> SEQ ID NO 22
<211> LENGTH: 9
<212> TYPE: PRT
<213> ORGANISM: Homo sapiens

<400> SEQUENCE: 22

Ile Met Pro Lys Ala Gly Leu Leu Ile
1               5

<210> SEQ ID NO 23
```

```
<211> LENGTH: 10
<212> TYPE: PRT
<213> ORGANISM: Homo sapiens

<400> SEQUENCE: 23

Met Glu Val Asp Pro Ile Gly His Leu Tyr
1               5                   10

<210> SEQ ID NO 24
<211> LENGTH: 9
<212> TYPE: PRT
<213> ORGANISM: Homo sapiens

<400> SEQUENCE: 24

Trp Gln Tyr Phe Phe Pro Val Ile Phe
1               5

<210> SEQ ID NO 25
<211> LENGTH: 10
<212> TYPE: PRT
<213> ORGANISM: Homo sapiens

<400> SEQUENCE: 25

Gly Val Tyr Asp Gly Arg Glu His Thr Val
1               5                   10

<210> SEQ ID NO 26
<211> LENGTH: 9
<212> TYPE: PRT
<213> ORGANISM: Homo sapiens

<400> SEQUENCE: 26

Met Val Lys Ile Ser Gly Gly Pro Arg
1               5

<210> SEQ ID NO 27
<211> LENGTH: 9
<212> TYPE: PRT
<213> ORGANISM: Homo sapiens

<400> SEQUENCE: 27

Gly Leu Tyr Asp Gly Met Glu His Leu
1               5

<210> SEQ ID NO 28
<211> LENGTH: 9
<212> TYPE: PRT
<213> ORGANISM: Homo sapiens

<400> SEQUENCE: 28

Val Arg Ile Gly His Leu Tyr Ile Leu
1               5

<210> SEQ ID NO 29
<211> LENGTH: 9
<212> TYPE: PRT
<213> ORGANISM: Homo sapiens

<400> SEQUENCE: 29

Ala Ala Arg Ala Val Phe Leu Ala Leu
1               5

<210> SEQ ID NO 30
<211> LENGTH: 9
<212> TYPE: PRT
```

```
<213> ORGANISM: Homo sapiens

<400> SEQUENCE: 30

Phe Leu Trp Gly Pro Arg Ala Tyr Ala
1               5

<210> SEQ ID NO 31
<211> LENGTH: 8
<212> TYPE: PRT
<213> ORGANISM: Homo sapiens

<400> SEQUENCE: 31

Tyr Arg Pro Arg Pro Arg Arg Tyr
1               5

<210> SEQ ID NO 32
<211> LENGTH: 9
<212> TYPE: PRT
<213> ORGANISM: Homo sapiens

<400> SEQUENCE: 32

Tyr Tyr Trp Pro Arg Pro Arg Arg Tyr
1               5

<210> SEQ ID NO 33
<211> LENGTH: 11
<212> TYPE: PRT
<213> ORGANISM: Homo sapiens

<400> SEQUENCE: 33

Met Thr Gln Gly Gln His Phe Leu Gln Lys Val
1               5                   10

<210> SEQ ID NO 34
<211> LENGTH: 11
<212> TYPE: PRT
<213> ORGANISM: Homo sapiens

<400> SEQUENCE: 34

Ser Leu Leu Met Trp Ile Thr Gln Cys Phe Leu
1               5                   10

<210> SEQ ID NO 35
<211> LENGTH: 9
<212> TYPE: PRT
<213> ORGANISM: Homo sapiens

<400> SEQUENCE: 35

Ser Leu Leu Met Trp Ile Thr Gln Cys
1               5

<210> SEQ ID NO 36
<211> LENGTH: 9
<212> TYPE: PRT
<213> ORGANISM: Homo sapiens

<400> SEQUENCE: 36

Gln Leu Ser Leu Leu Met Trp Ile Thr
1               5

<210> SEQ ID NO 37
<211> LENGTH: 10
<212> TYPE: PRT
<213> ORGANISM: Homo sapiens
```

```
<400> SEQUENCE: 37

Ala Ser Gly Pro Gly Gly Gly Ala Pro Arg
1               5                   10

<210> SEQ ID NO 38
<211> LENGTH: 9
<212> TYPE: PRT
<213> ORGANISM: Homo sapiens

<400> SEQUENCE: 38

Ala Ala Gly Ile Gly Ile Leu Thr Val
1               5

<210> SEQ ID NO 39
<211> LENGTH: 10
<212> TYPE: PRT
<213> ORGANISM: Homo sapiens

<400> SEQUENCE: 39

Glu Ala Ala Gly Ile Gly Ile Leu Thr Val
1               5                   10

<210> SEQ ID NO 40
<211> LENGTH: 9
<212> TYPE: PRT
<213> ORGANISM: Homo sapiens

<400> SEQUENCE: 40

Ile Leu Thr Val Ile Leu Gly Val Leu
1               5

<210> SEQ ID NO 41
<211> LENGTH: 10
<212> TYPE: PRT
<213> ORGANISM: Homo sapiens

<400> SEQUENCE: 41

Ala Glu Glu Ala Ala Gly Ile Gly Ile Leu
1               5                   10

<210> SEQ ID NO 42
<211> LENGTH: 11
<212> TYPE: PRT
<213> ORGANISM: Homo sapiens

<400> SEQUENCE: 42

Ala Glu Glu Ala Ala Gly Ile Gly Ile Leu Thr
1               5                   10

<210> SEQ ID NO 43
<211> LENGTH: 9
<212> TYPE: PRT
<213> ORGANISM: Homo sapiens

<400> SEQUENCE: 43

Thr Ile Leu Leu Gly Ile Phe Phe Leu
1               5

<210> SEQ ID NO 44
<211> LENGTH: 9
<212> TYPE: PRT
<213> ORGANISM: Homo sapiens

<400> SEQUENCE: 44
```

-continued

Phe Leu Ala Leu Ile Ile Cys Asn Ala
1               5

<210> SEQ ID NO 45
<211> LENGTH: 9
<212> TYPE: PRT
<213> ORGANISM: Homo sapiens

<400> SEQUENCE: 45

Lys Thr Trp Gly Gln Tyr Trp Gln Val
1               5

<210> SEQ ID NO 46
<211> LENGTH: 10
<212> TYPE: PRT
<213> ORGANISM: Homo sapiens

<400> SEQUENCE: 46

Ala Met Leu Gly Thr His Thr Met Glu Val
1               5                   10

<210> SEQ ID NO 47
<211> LENGTH: 9
<212> TYPE: PRT
<213> ORGANISM: Homo sapiens

<400> SEQUENCE: 47

Met Leu Gly Thr His Thr Met Glu Val
1               5

<210> SEQ ID NO 48
<211> LENGTH: 10
<212> TYPE: PRT
<213> ORGANISM: Homo sapiens

<400> SEQUENCE: 48

Ser Leu Ala Asp Thr Asn Ser Leu Ala Val
1               5                   10

<210> SEQ ID NO 49
<211> LENGTH: 9
<212> TYPE: PRT
<213> ORGANISM: Homo sapiens

<400> SEQUENCE: 49

Ile Thr Asp Gln Val Pro Phe Ser Val
1               5

<210> SEQ ID NO 50
<211> LENGTH: 10
<212> TYPE: PRT
<213> ORGANISM: Homo sapiens

<400> SEQUENCE: 50

Leu Leu Asp Gly Thr Ala Thr Leu Arg Leu
1               5                   10

<210> SEQ ID NO 51
<211> LENGTH: 9
<212> TYPE: PRT
<213> ORGANISM: Homo sapiens

<400> SEQUENCE: 51

Tyr Leu Glu Pro Gly Pro Val Thr Ala
1               5

```
<210> SEQ ID NO 52
<211> LENGTH: 10
<212> TYPE: PRT
<213> ORGANISM: Homo sapiens

<400> SEQUENCE: 52

Val Leu Tyr Arg Tyr Gly Ser Phe Ser Val
1               5                   10

<210> SEQ ID NO 53
<211> LENGTH: 9
<212> TYPE: PRT
<213> ORGANISM: Homo sapiens

<400> SEQUENCE: 53

Arg Leu Met Lys Gln Asp Phe Ser Val
1               5

<210> SEQ ID NO 54
<211> LENGTH: 9
<212> TYPE: PRT
<213> ORGANISM: Homo sapiens

<400> SEQUENCE: 54

Arg Leu Pro Arg Ile Phe Cys Ser Cys
1               5

<210> SEQ ID NO 55
<211> LENGTH: 9
<212> TYPE: PRT
<213> ORGANISM: Homo sapiens

<400> SEQUENCE: 55

Leu Ile Tyr Arg Arg Arg Leu Met Lys
1               5

<210> SEQ ID NO 56
<211> LENGTH: 9
<212> TYPE: PRT
<213> ORGANISM: Homo sapiens

<400> SEQUENCE: 56

Ala Leu Asn Phe Pro Gly Ser Gln Lys
1               5

<210> SEQ ID NO 57
<211> LENGTH: 10
<212> TYPE: PRT
<213> ORGANISM: Homo sapiens

<400> SEQUENCE: 57

Ser Leu Ile Tyr Arg Arg Arg Leu Met Lys
1               5                   10

<210> SEQ ID NO 58
<211> LENGTH: 9
<212> TYPE: PRT
<213> ORGANISM: Homo sapiens

<400> SEQUENCE: 58

Ala Leu Leu Ala Val Gly Ala Thr Lys
1               5
```

```
<210> SEQ ID NO 59
<211> LENGTH: 9
<212> TYPE: PRT
<213> ORGANISM: Homo sapiens

<400> SEQUENCE: 59

Val Tyr Phe Phe Leu Pro Asp His Leu
1               5

<210> SEQ ID NO 60
<211> LENGTH: 8
<212> TYPE: PRT
<213> ORGANISM: Homo sapiens

<400> SEQUENCE: 60

Ser Asn Asp Gly Pro Thr Leu Ile
1               5

<210> SEQ ID NO 61
<211> LENGTH: 10
<212> TYPE: PRT
<213> ORGANISM: Homo sapiens

<400> SEQUENCE: 61

Val Ser His Ser Phe Pro His Pro Leu Tyr
1               5                   10

<210> SEQ ID NO 62
<211> LENGTH: 10
<212> TYPE: PRT
<213> ORGANISM: Homo sapiens

<400> SEQUENCE: 62

Phe Leu Thr Pro Lys Lys Leu Gln Cys Val
1               5                   10

<210> SEQ ID NO 63
<211> LENGTH: 10
<212> TYPE: PRT
<213> ORGANISM: Homo sapiens

<400> SEQUENCE: 63

Val Ile Ser Asn Asp Val Cys Ala Gln Val
1               5                   10

<210> SEQ ID NO 64
<211> LENGTH: 10
<212> TYPE: PRT
<213> ORGANISM: Homo sapiens

<400> SEQUENCE: 64

His Ser Thr Asn Gly Val Thr Arg Ile Tyr
1               5                   10

<210> SEQ ID NO 65
<211> LENGTH: 9
<212> TYPE: PRT
<213> ORGANISM: Homo sapiens

<400> SEQUENCE: 65

Lys Cys Asp Ile Cys Thr Asp Glu Tyr
1               5

<210> SEQ ID NO 66
<211> LENGTH: 11
```

```
<212> TYPE: PRT
<213> ORGANISM: Homo sapiens

<400> SEQUENCE: 66

Ser Ser Asp Tyr Val Ile Pro Ile Gly Thr Tyr
1               5                   10

<210> SEQ ID NO 67
<211> LENGTH: 9
<212> TYPE: PRT
<213> ORGANISM: Homo sapiens

<400> SEQUENCE: 67

Tyr Met Asp Gly Thr Met Ser Gln Val
1               5

<210> SEQ ID NO 68
<211> LENGTH: 9
<212> TYPE: PRT
<213> ORGANISM: Homo sapiens

<400> SEQUENCE: 68

Met Leu Leu Ala Val Leu Tyr Cys Leu
1               5

<210> SEQ ID NO 69
<211> LENGTH: 9
<212> TYPE: PRT
<213> ORGANISM: Homo sapiens

<400> SEQUENCE: 69

Ala Phe Leu Pro Trp His Arg Leu Phe
1               5

<210> SEQ ID NO 70
<211> LENGTH: 9
<212> TYPE: PRT
<213> ORGANISM: Homo sapiens

<400> SEQUENCE: 70

Ser Glu Ile Trp Arg Asp Ile Asp Phe
1               5

<210> SEQ ID NO 71
<211> LENGTH: 9
<212> TYPE: PRT
<213> ORGANISM: Homo sapiens

<400> SEQUENCE: 71

Met Ser Leu Gln Arg Gln Phe Leu Arg
1               5

<210> SEQ ID NO 72
<211> LENGTH: 9
<212> TYPE: PRT
<213> ORGANISM: Homo sapiens

<400> SEQUENCE: 72

Ser Val Tyr Asp Phe Phe Val Trp Leu
1               5

<210> SEQ ID NO 73
<211> LENGTH: 9
<212> TYPE: PRT
<213> ORGANISM: Homo sapiens
```

```
<400> SEQUENCE: 73

Thr Leu Asp Ser Gln Val Met Ser Leu
1               5

<210> SEQ ID NO 74
<211> LENGTH: 9
<212> TYPE: PRT
<213> ORGANISM: Homo sapiens

<400> SEQUENCE: 74

Leu Leu Gly Pro Gly Arg Pro Tyr Arg
1               5

<210> SEQ ID NO 75
<211> LENGTH: 9
<212> TYPE: PRT
<213> ORGANISM: Homo sapiens

<400> SEQUENCE: 75

Leu Leu Gly Pro Gly Arg Pro Tyr Arg
1               5

<210> SEQ ID NO 76
<211> LENGTH: 9
<212> TYPE: PRT
<213> ORGANISM: Homo sapiens

<400> SEQUENCE: 76

Ala Asn Asp Pro Ile Phe Val Val Leu
1               5

<210> SEQ ID NO 77
<211> LENGTH: 8
<212> TYPE: PRT
<213> ORGANISM: Homo sapiens

<400> SEQUENCE: 77

Ala Phe Leu Arg His Ala Ala Leu
1               5

<210> SEQ ID NO 78
<211> LENGTH: 10
<212> TYPE: PRT
<213> ORGANISM: Homo sapiens

<400> SEQUENCE: 78

Asp Tyr Pro Ser Leu Ser Ala Thr Asp Ile
1               5                   10

<210> SEQ ID NO 79
<211> LENGTH: 11
<212> TYPE: PRT
<213> ORGANISM: Homo sapiens

<400> SEQUENCE: 79

Met Leu Met Ala Gln Glu Ala Leu Ala Phe Leu
1               5                   10

<210> SEQ ID NO 80
<211> LENGTH: 9
<212> TYPE: PRT
<213> ORGANISM: Homo sapiens

<400> SEQUENCE: 80
```

```
Tyr Leu Ser Gly Ala Asn Leu Asn Leu
1               5

<210> SEQ ID NO 81
<211> LENGTH: 9
<212> TYPE: PRT
<213> ORGANISM: Homo sapiens

<400> SEQUENCE: 81

His Leu Phe Gly Tyr Ser Trp Tyr Lys
1               5

<210> SEQ ID NO 82
<211> LENGTH: 9
<212> TYPE: PRT
<213> ORGANISM: Homo sapiens

<400> SEQUENCE: 82

Lys Phe His Arg Val Ile Lys Asp Phe
1               5

<210> SEQ ID NO 83
<211> LENGTH: 9
<212> TYPE: PRT
<213> ORGANISM: Homo sapiens

<400> SEQUENCE: 83

Asp Phe Met Ile Gln Gly Gly Asp Phe
1               5

<210> SEQ ID NO 84
<211> LENGTH: 9
<212> TYPE: PRT
<213> ORGANISM: Homo sapiens

<400> SEQUENCE: 84

Lys Ile Phe Gly Ser Leu Ala Phe Leu
1               5

<210> SEQ ID NO 85
<211> LENGTH: 9
<212> TYPE: PRT
<213> ORGANISM: Homo sapiens

<400> SEQUENCE: 85

Ile Ile Ser Ala Val Val Gly Ile Leu
1               5

<210> SEQ ID NO 86
<211> LENGTH: 9
<212> TYPE: PRT
<213> ORGANISM: Homo sapiens

<400> SEQUENCE: 86

Arg Leu Leu Gln Glu Thr Glu Leu Val
1               5

<210> SEQ ID NO 87
<211> LENGTH: 9
<212> TYPE: PRT
<213> ORGANISM: Homo sapiens

<400> SEQUENCE: 87

Val Val Leu Gly Val Val Phe Gly Ile
```

```
<210> SEQ ID NO 88
<211> LENGTH: 9
<212> TYPE: PRT
<213> ORGANISM: Homo sapiens

<400> SEQUENCE: 88

Ile Leu His Asn Gly Ala Tyr Ser Leu
1               5

<210> SEQ ID NO 89
<211> LENGTH: 10
<212> TYPE: PRT
<213> ORGANISM: Homo sapiens

<400> SEQUENCE: 89

Tyr Met Ile Met Val Lys Cys Trp Met Ile
1               5                   10

<210> SEQ ID NO 90
<211> LENGTH: 9
<212> TYPE: PRT
<213> ORGANISM: Homo sapiens

<400> SEQUENCE: 90

Val Leu Arg Glu Asn Thr Ser Pro Lys
1               5

<210> SEQ ID NO 91
<211> LENGTH: 9
<212> TYPE: PRT
<213> ORGANISM: Homo sapiens

<400> SEQUENCE: 91

Ile Leu Ala Lys Phe Leu His Trp Leu
1               5

<210> SEQ ID NO 92
<211> LENGTH: 9
<212> TYPE: PRT
<213> ORGANISM: Homo sapiens

<400> SEQUENCE: 92

Ile Leu Ala Lys Phe Leu His Trp Leu
1               5

<210> SEQ ID NO 93
<211> LENGTH: 9
<212> TYPE: PRT
<213> ORGANISM: Homo sapiens

<400> SEQUENCE: 93

Arg Leu Val Asp Asp Phe Leu Leu Val
1               5

<210> SEQ ID NO 94
<211> LENGTH: 9
<212> TYPE: PRT
<213> ORGANISM: Homo sapiens

<400> SEQUENCE: 94

Ser Pro Arg Trp Trp Pro Thr Cys Leu
1               5
```

```
<210> SEQ ID NO 95
<211> LENGTH: 9
<212> TYPE: PRT
<213> ORGANISM: Homo sapiens

<400> SEQUENCE: 95

Ser Thr Ala Pro Pro Ala His Gly Val
1               5

<210> SEQ ID NO 96
<211> LENGTH: 9
<212> TYPE: PRT
<213> ORGANISM: Homo sapiens

<400> SEQUENCE: 96

Ser Thr Ala Pro Pro Val His Asn Val
1               5

<210> SEQ ID NO 97
<211> LENGTH: 9
<212> TYPE: PRT
<213> ORGANISM: Homo sapiens

<400> SEQUENCE: 97

Leu Leu Asn Gln Leu Gln Val Asn Leu
1               5

<210> SEQ ID NO 98
<211> LENGTH: 9
<212> TYPE: PRT
<213> ORGANISM: Homo sapiens

<400> SEQUENCE: 98

Met Leu Trp Gly Trp Arg Glu His Val
1               5

<210> SEQ ID NO 99
<211> LENGTH: 9
<212> TYPE: PRT
<213> ORGANISM: Homo sapiens

<400> SEQUENCE: 99

Leu Tyr Val Asp Ser Leu Phe Phe Leu
1               5

<210> SEQ ID NO 100
<211> LENGTH: 9
<212> TYPE: PRT
<213> ORGANISM: Homo sapiens

<400> SEQUENCE: 100

Ala Tyr Gly Leu Asp Phe Tyr Ile Leu
1               5

<210> SEQ ID NO 101
<211> LENGTH: 9
<212> TYPE: PRT
<213> ORGANISM: Homo sapiens

<400> SEQUENCE: 101

Val Pro Tyr Gly Ser Phe Lys His Val
1               5

<210> SEQ ID NO 102
```

```
<211> LENGTH: 9
<212> TYPE: PRT
<213> ORGANISM: Homo sapiens

<400> SEQUENCE: 102

Leu Pro Arg Trp Pro Pro Pro Gln Leu
1               5

<210> SEQ ID NO 103
<211> LENGTH: 9
<212> TYPE: PRT
<213> ORGANISM: Homo sapiens

<400> SEQUENCE: 103

Glu Tyr Arg Gly Phe Thr Gln Asp Phe
1               5

<210> SEQ ID NO 104
<211> LENGTH: 9
<212> TYPE: PRT
<213> ORGANISM: Homo sapiens

<400> SEQUENCE: 104

Lys Gly Ser Gly Lys Met Lys Thr Glu
1               5

<210> SEQ ID NO 105
<211> LENGTH: 10
<212> TYPE: PRT
<213> ORGANISM: Homo sapiens

<400> SEQUENCE: 105

Val Tyr Asp Tyr Asn Cys His Val Asp Leu
1               5                   10

<210> SEQ ID NO 106
<211> LENGTH: 9
<212> TYPE: PRT
<213> ORGANISM: Homo sapiens

<400> SEQUENCE: 106

Ala Tyr Ile Asp Phe Glu Met Lys Ile
1               5

<210> SEQ ID NO 107
<211> LENGTH: 9
<212> TYPE: PRT
<213> ORGANISM: Homo sapiens

<400> SEQUENCE: 107

Arg Met Phe Pro Asn Ala Pro Tyr Leu
1               5

<210> SEQ ID NO 108
<211> LENGTH: 9
<212> TYPE: PRT
<213> ORGANISM: Homo sapiens

<400> SEQUENCE: 108

Gly Val Ala Leu Gln Thr Met Lys Gln
1               5

<210> SEQ ID NO 109
<211> LENGTH: 9
<212> TYPE: PRT
```

<213> ORGANISM: Homo sapiens

<400> SEQUENCE: 109

Ser Tyr Leu Asp Ser Gly Ile His Phe
1               5

<210> SEQ ID NO 110
<211> LENGTH: 9
<212> TYPE: PRT
<213> ORGANISM: Homo sapiens

<400> SEQUENCE: 110

Phe Pro Ser Asp Ser Trp Cys Tyr Phe
1               5

<210> SEQ ID NO 111
<211> LENGTH: 10
<212> TYPE: PRT
<213> ORGANISM: Homo sapiens

<400> SEQUENCE: 111

Ala Cys Asp Pro His Ser Gly His Phe Val
1               5                   10

<210> SEQ ID NO 112
<211> LENGTH: 9
<212> TYPE: PRT
<213> ORGANISM: Homo sapiens

<400> SEQUENCE: 112

Glu Thr Val Ser Glu Gln Ser Asn Val
1               5

<210> SEQ ID NO 113
<211> LENGTH: 9
<212> TYPE: PRT
<213> ORGANISM: Homo sapiens

<400> SEQUENCE: 113

His Leu Ser Thr Ala Phe Ala Arg Val
1               5

<210> SEQ ID NO 114
<211> LENGTH: 13
<212> TYPE: PRT
<213> ORGANISM: Homo sapiens

<400> SEQUENCE: 114

Cys Val Glu Trp Leu Arg Ile Tyr Leu Glu Asn Gly Lys
1               5                   10

<210> SEQ ID NO 115
<211> LENGTH: 9
<212> TYPE: PRT
<213> ORGANISM: Homo sapiens

<400> SEQUENCE: 115

Ser Leu Phe Glu Gly Ile Asp Ile Tyr
1               5

<210> SEQ ID NO 116
<211> LENGTH: 10
<212> TYPE: PRT
<213> ORGANISM: Homo sapiens

```
<400> SEQUENCE: 116

Tyr Ser Trp Met Asp Ile Ser Cys Trp Ile
1               5                   10

<210> SEQ ID NO 117
<211> LENGTH: 9
<212> TYPE: PRT
<213> ORGANISM: Homo sapiens

<400> SEQUENCE: 117

Ala Glu Pro Ile Asn Ile Gln Thr Val
1               5

<210> SEQ ID NO 118
<211> LENGTH: 9
<212> TYPE: PRT
<213> ORGANISM: Homo sapiens

<400> SEQUENCE: 118

Glu Glu Lys Leu Ile Val Val Leu Phe
1               5

<210> SEQ ID NO 119
<211> LENGTH: 10
<212> TYPE: PRT
<213> ORGANISM: Homo sapiens

<400> SEQUENCE: 119

Ser Glu Leu Phe Arg Ser Gly Leu Asp Tyr
1               5                   10

<210> SEQ ID NO 120
<211> LENGTH: 9
<212> TYPE: PRT
<213> ORGANISM: Homo sapiens

<400> SEQUENCE: 120

Phe Arg Ser Gly Leu Asp Ser Tyr Val
1               5

<210> SEQ ID NO 121
<211> LENGTH: 9
<212> TYPE: PRT
<213> ORGANISM: Homo sapiens

<400> SEQUENCE: 121

Glu Ala Phe Ile Gln Pro Ile Thr Arg
1               5

<210> SEQ ID NO 122
<211> LENGTH: 9
<212> TYPE: PRT
<213> ORGANISM: Homo sapiens

<400> SEQUENCE: 122

Lys Ile Asn Lys Asn Pro Lys Tyr Lys
1               5

<210> SEQ ID NO 123
<211> LENGTH: 10
<212> TYPE: PRT
<213> ORGANISM: Homo sapiens

<400> SEQUENCE: 123
```

-continued

Ser Pro Ser Ser Asn Arg Ile Arg Asn Thr
1               5                   10

<210> SEQ ID NO 124
<211> LENGTH: 9
<212> TYPE: PRT
<213> ORGANISM: Homo sapiens

<400> SEQUENCE: 124

Asp Tyr Ser Ala Arg Trp Asn Glu Ile
1               5

<210> SEQ ID NO 125
<211> LENGTH: 9
<212> TYPE: PRT
<213> ORGANISM: Homo sapiens

<400> SEQUENCE: 125

Ala Tyr Asp Phe Leu Tyr Asn Tyr Leu
1               5

<210> SEQ ID NO 126
<211> LENGTH: 9
<212> TYPE: PRT
<213> ORGANISM: Homo sapiens

<400> SEQUENCE: 126

Ser Tyr Thr Arg Leu Phe Leu Ile Leu
1               5

<210> SEQ ID NO 127
<211> LENGTH: 10
<212> TYPE: PRT
<213> ORGANISM: Homo sapiens

<400> SEQUENCE: 127

Glu Val Ile Ser Cys Lys Leu Ile Lys Arg
1               5                   10

<210> SEQ ID NO 128
<211> LENGTH: 9
<212> TYPE: PRT
<213> ORGANISM: Homo sapiens

<400> SEQUENCE: 128

Arg Val Ala Ala Leu Ala Arg Asp Ala
1               5

<210> SEQ ID NO 129
<211> LENGTH: 16
<212> TYPE: PRT
<213> ORGANISM: Homo sapiens

<400> SEQUENCE: 129

Asp Val Pro Lys Trp Ile Ser Ile Met Thr Glu Arg Ser Val Pro His
1               5                   10                  15

<210> SEQ ID NO 130
<211> LENGTH: 16
<212> TYPE: PRT
<213> ORGANISM: Homo sapiens

<400> SEQUENCE: 130

Trp Asn Arg Gln Leu Tyr Pro Glu Trp Thr Glu Ala Gln Arg Leu Asp
1               5                   10                  15

```
<210> SEQ ID NO 131
<211> LENGTH: 14
<212> TYPE: PRT
<213> ORGANISM: Homo sapiens

<400> SEQUENCE: 131

Leu Leu Lys Tyr Arg Ala Arg Glu Pro Val Thr Lys Ala Glu
1               5                   10

<210> SEQ ID NO 132
<211> LENGTH: 15
<212> TYPE: PRT
<213> ORGANISM: Homo sapiens

<400> SEQUENCE: 132

Thr Ser Tyr Val Lys Val Leu His His Met Val Lys Ile Ser Gly
1               5                   10                  15

<210> SEQ ID NO 133
<211> LENGTH: 14
<212> TYPE: PRT
<213> ORGANISM: Homo sapiens

<400> SEQUENCE: 133

Ala Glu Leu Val His Phe Leu Leu Leu Lys Tyr Arg Ala Arg
1               5                   10

<210> SEQ ID NO 134
<211> LENGTH: 23
<212> TYPE: PRT
<213> ORGANISM: Homo sapiens

<400> SEQUENCE: 134

Arg Asn Gly Tyr Arg Ala Leu Met Asp Lys Ser Leu His Val Gly Thr
1               5                   10                  15

Gln Cys Ala Leu Thr Arg Arg
            20

<210> SEQ ID NO 135
<211> LENGTH: 12
<212> TYPE: PRT
<213> ORGANISM: Homo sapiens

<400> SEQUENCE: 135

Pro Gly Ser Thr Ala Pro Pro Ala His Gly Val Thr
1               5                   10

<210> SEQ ID NO 136
<211> LENGTH: 10
<212> TYPE: PRT
<213> ORGANISM: Homo sapiens

<400> SEQUENCE: 136

Val Leu Leu Lys Glu Phe Thr Val Ser Gly
1               5                   10

<210> SEQ ID NO 137
<211> LENGTH: 18
<212> TYPE: PRT
<213> ORGANISM: Homo sapiens

<400> SEQUENCE: 137

Pro Leu Pro Val Pro Gly Val Leu Leu Lys Glu Phe Thr Val Ser Gly
```

-continued

```
                1               5                  10                  15
Asn Ile

<210> SEQ ID NO 138
<211> LENGTH: 18
<212> TYPE: PRT
<213> ORGANISM: Homo sapiens

<400> SEQUENCE: 138

Val Leu Leu Lys Glu Phe Thr Val Ser Gly Asn Ile Leu Thr Ile Arg
1               5                  10                  15

Leu Thr

<210> SEQ ID NO 139
<211> LENGTH: 18
<212> TYPE: PRT
<213> ORGANISM: Homo sapiens

<400> SEQUENCE: 139

Ala Ala Asp His Arg Gln Leu Gln Leu Ser Ile Ser Ser Cys Leu Gln
1               5                  10                  15

Gln Leu

<210> SEQ ID NO 140
<211> LENGTH: 15
<212> TYPE: PRT
<213> ORGANISM: Homo sapiens

<400> SEQUENCE: 140

Ile Leu Leu Gly Arg Met Ser Leu Phe Met Pro Glu Asp Thr Gly
1               5                  10                  15

<210> SEQ ID NO 141
<211> LENGTH: 13
<212> TYPE: PRT
<213> ORGANISM: Homo sapiens

<400> SEQUENCE: 141

Ser Leu Phe His Pro Glu Asp Thr Gly Gln Val Phe Gln
1               5                  10

<210> SEQ ID NO 142
<211> LENGTH: 15
<212> TYPE: PRT
<213> ORGANISM: Homo sapiens

<400> SEQUENCE: 142

Gln Val Phe Gln Val Ser His Ser Phe Pro His Pro Leu Tyr Asp
1               5                  10                  15

<210> SEQ ID NO 143
<211> LENGTH: 15
<212> TYPE: PRT
<213> ORGANISM: Homo sapiens

<400> SEQUENCE: 143

Asn Asp Leu Met Leu Leu Arg Leu Ser Glu Pro Ala Glu Leu Thr
1               5                  10                  15

<210> SEQ ID NO 144
<211> LENGTH: 13
<212> TYPE: PRT
<213> ORGANISM: Homo sapiens
```

-continued

```
<400> SEQUENCE: 144

Lys Lys Leu Gln Cys Val Gln Leu His Val Ile Ser Met
1               5                   10

<210> SEQ ID NO 145
<211> LENGTH: 15
<212> TYPE: PRT
<213> ORGANISM: Homo sapiens

<400> SEQUENCE: 145

Gly Val Leu Gln Gly Ile Thr Ser Met Gly Ser Glu Pro Cys Ala
1               5                   10                  15

<210> SEQ ID NO 146
<211> LENGTH: 15
<212> TYPE: PRT
<213> ORGANISM: Homo sapiens

<400> SEQUENCE: 146

Gln Asn Ile Leu Leu Ser Asn Ala Pro Leu Gly Pro Gln Phe Pro
1               5                   10                  15

<210> SEQ ID NO 147
<211> LENGTH: 15
<212> TYPE: PRT
<213> ORGANISM: Homo sapiens

<400> SEQUENCE: 147

Asp Tyr Ser Tyr Leu Gln Asp Ser Asp Pro Asp Ser Phe Gln Asp
1               5                   10                  15

<210> SEQ ID NO 148
<211> LENGTH: 13
<212> TYPE: PRT
<213> ORGANISM: Homo sapiens

<400> SEQUENCE: 148

Ser Tyr Leu Gln Asp Ser Asp Pro Asp Ser Phe Gln Asp
1               5                   10

<210> SEQ ID NO 149
<211> LENGTH: 21
<212> TYPE: PRT
<213> ORGANISM: Homo sapiens

<400> SEQUENCE: 149

Arg His Arg Pro Leu Gln Glu Val Tyr Pro Glu Ala Asn Ala Pro Ile
1               5                   10                  15

Gly His Asn Arg Glu
            20

<210> SEQ ID NO 150
<211> LENGTH: 11
<212> TYPE: PRT
<213> ORGANISM: Homo sapiens

<400> SEQUENCE: 150

Glu Ile Trp Arg Asp Ile Asp Phe Ala His Glu
1               5                   10

<210> SEQ ID NO 151
<211> LENGTH: 13
<212> TYPE: PRT
```

<213> ORGANISM: Homo sapiens

<400> SEQUENCE: 151

```
Leu Phe Met Asp Thr Leu Ser Phe Val Cys Pro Leu Cys
1               5                   10
```

<210> SEQ ID NO 152
<211> LENGTH: 13
<212> TYPE: PRT
<213> ORGANISM: Homo sapiens

<400> SEQUENCE: 152

```
Leu Phe Met Asp Ser Leu Asn Phe Val Cys Pro Trp Cys
1               5                   10
```

<210> SEQ ID NO 153
<211> LENGTH: 12
<212> TYPE: PRT
<213> ORGANISM: Homo sapiens

<400> SEQUENCE: 153

```
Phe Ser Trp Ala Met Asp Leu Asp Pro Lys Gly Ala
1               5                   10
```

<210> SEQ ID NO 154
<211> LENGTH: 15
<212> TYPE: PRT
<213> ORGANISM: Homo sapiens

<400> SEQUENCE: 154

```
Gly Glu Leu Ile Gly Ile Leu Asn Ala Ala Lys Val Pro Ala Asp
1               5                   10                  15
```

<210> SEQ ID NO 155
<211> LENGTH: 9
<212> TYPE: PRT
<213> ORGANISM: Homo sapiens

<400> SEQUENCE: 155

```
Phe Met Val Glu Leu Val Glu Gly Ala
1               5
```

<210> SEQ ID NO 156
<211> LENGTH: 9
<212> TYPE: PRT
<213> ORGANISM: Homo sapiens

<400> SEQUENCE: 156

```
Lys Leu Ser Glu Gln Glu Ser Leu Leu
1               5
```

<210> SEQ ID NO 157
<211> LENGTH: 9
<212> TYPE: PRT
<213> ORGANISM: Homo sapiens

<400> SEQUENCE: 157

```
Met Leu Thr Asn Ser Cys Val Lys Leu
1               5
```

<210> SEQ ID NO 158
<211> LENGTH: 9
<212> TYPE: PRT
<213> ORGANISM: Homo sapiens -continued

```
<400> SEQUENCE: 158

Ser Ser Lys Ala Leu Gln Arg Pro Val
1               5

<210> SEQ ID NO 159
<211> LENGTH: 9
<212> TYPE: PRT
<213> ORGANISM: Homo sapiens

<400> SEQUENCE: 159

Ala Thr Gly Phe Lys Gln Ser Ser Lys
1               5

<210> SEQ ID NO 160
<211> LENGTH: 9
<212> TYPE: PRT
<213> ORGANISM: Homo sapiens

<400> SEQUENCE: 160

Lys Gln Ser Ser Lys Ala Leu Gln Arg
1               5

<210> SEQ ID NO 161
<211> LENGTH: 11
<212> TYPE: PRT
<213> ORGANISM: Homo sapiens

<400> SEQUENCE: 161

His Ser Ala Thr Gly Phe Lys Gln Ser Ser Lys
1               5                   10

<210> SEQ ID NO 162
<211> LENGTH: 9
<212> TYPE: PRT
<213> ORGANISM: Homo sapiens

<400> SEQUENCE: 162

Lys Gln Ser Ser Lys Ala Leu Gln Arg
1               5

<210> SEQ ID NO 163
<211> LENGTH: 9
<212> TYPE: PRT
<213> ORGANISM: Homo sapiens

<400> SEQUENCE: 163

Gly Phe Lys Gln Ser Ser Lys Ala Leu
1               5

<210> SEQ ID NO 164
<211> LENGTH: 9
<212> TYPE: PRT
<213> ORGANISM: Homo sapiens

<400> SEQUENCE: 164

Arg Ile Ala Glu Cys Ile Leu Gly Met
1               5

<210> SEQ ID NO 165
<211> LENGTH: 17
<212> TYPE: PRT
<213> ORGANISM: Homo sapiens

<400> SEQUENCE: 165
```

```
Glu Gly Ala Phe His Gly Asp Ala Glu Ala Leu Gln Arg Pro Val Ala
1               5                   10                  15

Ser

<210> SEQ ID NO 166
<211> LENGTH: 17
<212> TYPE: PRT
<213> ORGANISM: Homo sapiens

<400> SEQUENCE: 166

Ile Pro Leu Thr Ile Asn Lys Glu Glu Ala Leu Gln Arg Pro Val Ala
1               5                   10                  15

Ser

<210> SEQ ID NO 167
<211> LENGTH: 17
<212> TYPE: PRT
<213> ORGANISM: Homo sapiens

<400> SEQUENCE: 167

Ala Thr Gly Phe Lys Gln Ser Ser Lys Ala Leu Gln Arg Pro Val Ala
1               5                   10                  15

Ser

<210> SEQ ID NO 168
<211> LENGTH: 17
<212> TYPE: PRT
<213> ORGANISM: Homo sapiens

<400> SEQUENCE: 168

Ala Thr Gly Phe Lys Gln Ser Ser Lys Ala Leu Gln Arg Pro Val Ala
1               5                   10                  15

Ser

<210> SEQ ID NO 169
<211> LENGTH: 17
<212> TYPE: PRT
<213> ORGANISM: Homo sapiens

<400> SEQUENCE: 169

Ala Thr Gly Phe Lys Gln Ser Ser Lys Ala Leu Gln Arg Pro Val Ala
1               5                   10                  15

Ser

<210> SEQ ID NO 170
<211> LENGTH: 24
<212> TYPE: PRT
<213> ORGANISM: Homo sapiens

<400> SEQUENCE: 170

Leu Ile Val Val Ile Val His Ser Ala Thr Gly Phe Lys Gln Ser Ser
1               5                   10                  15

Lys Ala Leu Gln Arg Pro Val Ala
            20

<210> SEQ ID NO 171
<211> LENGTH: 25
<212> TYPE: PRT
<213> ORGANISM: Homo sapiens

<400> SEQUENCE: 171
```

-continued

Ile Val His Ser Ala Thr Gly Phe Lys Gln Ser Ser Lys Ala Leu Gln
1               5                   10                  15

Arg Pro Val Ala Ser Asp Phe Glu Pro
            20                  25

<210> SEQ ID NO 172
<211> LENGTH: 16
<212> TYPE: PRT
<213> ORGANISM: Homo sapiens

<400> SEQUENCE: 172

Thr Met Lys Gln Ile Cys Lys Lys Glu Ile Arg Arg Leu His Gln Tyr
1               5                   10                  15

<210> SEQ ID NO 173
<211> LENGTH: 15
<212> TYPE: PRT
<213> ORGANISM: Homo sapiens

<400> SEQUENCE: 173

Gly Gly Ala Pro Pro Val Thr Trp Arg Arg Ala Pro Ala Pro Gly
1               5                   10                  15

<210> SEQ ID NO 174
<211> LENGTH: 15
<212> TYPE: PRT
<213> ORGANISM: Homo sapiens

<400> SEQUENCE: 174

Trp Arg Arg Ala Pro Ala Pro Gly Ala Lys Ala Met Ala Pro Gly
1               5                   10                  15

<210> SEQ ID NO 175
<211> LENGTH: 25
<212> TYPE: PRT
<213> ORGANISM: Homo sapiens

<400> SEQUENCE: 175

Asn Ser Asn His Val Ala Ser Gly Ala Gly Glu Ala Ala Ile Glu Thr
1               5                   10                  15

Gln Ser Ser Ser Ser Glu Glu Ile Val
            20                  25

<210> SEQ ID NO 176
<211> LENGTH: 17
<212> TYPE: PRT
<213> ORGANISM: Homo sapiens

<400> SEQUENCE: 176

Glu Gly Ala Phe His Gly Asp Ala Glu Ala Leu Gln Arg Pro Val Ala
1               5                   10                  15

Ser

<210> SEQ ID NO 177
<211> LENGTH: 15
<212> TYPE: PRT
<213> ORGANISM: Homo sapiens

<400> SEQUENCE: 177

Ile Gly Arg Ile Ala Glu Cys Ile Leu Gly Met Asn Pro Ser Arg
1               5                   10                  15

METHOD FOR PRODUCING CYTOTOXIC T-CELLS

CROSS-REFERENCE TO RELATED APPLICATIONS

This application is a continuation-in-part of U.S. application Ser. No. 10/116,901, filed Apr. 5, 2002, now U.S. Pat. No. 7,264,965, which is a continuation-in-part of U.S. application Ser. No. 09/878,158, filed Jun. 8, 2001, which is a continuation-in-part of U.S. application Ser. No. 09/724,985, now U.S. Pat. No. 7,268,219, filed Nov. 28, 2000, as a continuation-in-part of PCT/GB99/01764, filed Jun. 4, 1999, designating the U.S., published as WO 99/64464 and claiming priority to UK applications Serial Nos. 9812227.8, filed Jun. 5, 1998 and 9908333.9, filed Apr. 12, 1999. This application is also a continuation-in-part of U.S. application Ser. No. 09/878,158, filed Jun. 8,2001. And, this application is also a continuation-in-part of U.S. application Ser. No. 09/724,985, filed Nov. 28, 2000 now U.S. Pat. No. 7,268,219.

Each of the foregoing applications and patents, each foregoing publication, and each document cited or referenced in each of the foregoing applications and patents, including during the prosecution of each of the foregoing applications and patents ("application and article cited documents"), and any manufacturer's instructions or catalogues for any products cited or mentioned in each of the foregoing applications and patents and articles and in any of the application and article cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

BACKGROUND OF THE INVENTION

Cytotoxic T cells in the cellular immune system are responsible for recognising cells that display "foreign" markings, and triggering an immunological response against such cells. Each cytotoxic T cell expresses a number of cell surface recognition receptors, which recognition receptors all possess precise specificity for a particular "foreign" peptide sequence, which recognition receptors are adapted to bind to HLA class I molecules expressed on the surface of cells scanned by the T cell. HLA class I molecules are cell surface molecules which possess a peptide binding groove exposed on the external surface of the cell, which groove is arranged under normal circumstances to bind a peptide derived from the interior of the cell. When a recognition receptor on a cytotoxic T cell binds to an HLA class I molecule on the surface of a scanned cell, the recognition receptor is enabled to contact the peptide binding groove of the HLA class I molecule and interact with any peptide contained therein. If this peptide matches the specificity of the recognition receptor, the T cell is said to recognise the scanned cell, and may consequently trigger an immunological response against said scanned cell.

Cytotoxic T cells of various specificities within a host immune system are also able to recognise and trigger an immunological response against a cell exhibiting an HLA class I molecule which is of a different allotype from the HLA class I molecules of the host cells. An immunological response of this kind is known as an "alloreactive" response.

An immunological response against a cell usually results in the lysis of the cell and/or the local release of cytokines. It has however been observed that cytotoxic T cells do not trigger the lysis of so-called antigen presenting cells (APCs) in this way. Instead, the immunological response triggered by T cell recognition of an HLA class I molecule on the surface of an antigen presenting cell results in the direct selective proliferation of the cytotoxic T cell. The host immune system consequently becomes immunised against any cells exhibiting the foreign peptide recognised by the surface recognition receptors on this T cell.

It is recognised that the effector mechanisms of the cellular immune system could be a powerful tool in the prevention and treatment of many illnesses, including malignant processes and infectious and auto-immune diseases, including cancer. A small number of the HLA class I molecules on a tumour cell surface may be found to bind peptides which are selectively expressed or over-expressed in tumour cells and are capable of being recognised by cytotoxic T cells in the immune system. Such peptides may furthermore be tumour specific, being found only infrequently, or not at all, on the HLA class I molecules of non-tumour cells. An example of one such tumour specific peptide is the HMW-MAA antigen found on melanoma cells. However, the number of HLA molecules presenting such peptides is generally too small to stimulate an effective immunological response against the tumour cell. Moreover, such peptides are rarely, if ever, presented by HLA class I molecules on the surface of APCs.

Attempts to enhance the response of the cellular immune system to tumour cells have hitherto focused on increasing tumour cell immunogenicity. In particular, various efforts have been made to produce high-level expression of immunogenic HLA class I molecules on the surface of tumour cells, through the techniques of gene therapy. The delivery of cDNA encoding an HLA class I gene containing an immunogenic peptide in the leader sequence of the HLA molecule has been described in Kang (Cancer Res. 57, 1997, 202-205). Meanwhile, Stopeck (J Clinical Oncolosv 15, 1997, 341-349) describes the transfection of allogeneic HLA class I in patients with melanoma. This work has demonstrated some response in clinical trials, but has also highlighted the difficulties involved in targeting tumour cells at multiple sites in vivo through the techniques of gene therapy.

Existing technology for production of alloreactive peptide specific cytotoxic T lymphocytes (CTLs) requires mixing donor cells with, initially, RMA cells (mouse cancer line), CIR or T2 cells (human tumour cell), and then Drosophila cells. This is both complicated and of low efficacy. These methods are also very 'dirty' which in this context means that they use cancer cells. It is undesirable to use cancer cells in the production of CTLs for administration to a subject.

Existing methods for producing CTLs in vitro are very labour intensive and expensive, involving culture of at least three different cell lines and complicated procedures of contacting the CTLs with each of these as part of the method(s). It is an advantageous feature of the present invention that CTL production is simplified and is also cheaper and/or easier and/or faster than existing techniques.

Subjects can be known to tolerate their own tumours rather than mounting an immunological response to them. This is because the tumour can appear as 'own' or 'self' to the immune system. Other people's immune systems (i.e. alloreactive) can fight better. However, the drawback with this approach is that a dual response can be produced in that the ordinary tissues of the recipient can be attacked too. This is the so-called graft versus host disease. The actual host can be attacked, which is problematic. One of the advantages of the present invention is the alleviation of this problem with existing methods by provision of better CTLs, which react with the target peptide in the appropriate context, such as when complexed with HLA-A2.

A number of approaches to the generation of anti-tumour CTLs, including use of dendritic cells, DNA vaccines and peptide administration are in clinical development, aiming to expand autologous tumour reactive CTLs. However producing autologous CTLs against certain targets is difficult or impossible due to immunological tolerance, and existing attempts at producing alloreactive CTLs have serious drawbacks as explained above (Sadovnikova 1998, Stauss 1999, Dutoit 2002).

Furthermore, some. target peptides apparently cannot be targeted by autologous means. Melan-A is an example of a peptide that can be targeted by autologous methods, but many others such as WT1 cannot be targeted by such methods. The present invention advantageously permits the targeting of a far wider range of peptides than conventional autologous methods.

Other techniques for production of CTLs have been described, such as production using T2 cells. T2 cells are a genetically altered human cell line, which is deficient in the genes encoding the transporter associated with antigen processing (TAP). This cell line therefore fails to properly load HLA-A2 Class I molecules with endogenous peptides. Therefore, exogenously added peptides can be made to bind a proportion of the HLA-A2 molecules on the surface of T2 cells. These techniques for producing CTLs rely on the culture of T2 cells, followed by peptide loading, cleaning of the cells and using them as a stimulatory cell to try to stimulate CTLs, for example from PBMC samples. Even when this labour intensive method appears to work, the stimulatory cells have to be constantly prepared and replaced at regular intervals in a rolling maintenance program. The present invention advantageously avoids the use of such T2 cells and also greatly simplifies the procedure. Furthermore, use of T2 cells is limited to HLA-A2, whereas the methods of the present invention are also applicable to other HLA types.

The existing technologies employed to produce alloreactive CTLs are relatively inefficient and the choice of target HLA class I is restricted by the limited allotypes of the commonly used antigen presenting cells, which are themselves genetically altered artificial cell lines.

It is desirable to separate out the beneficial effects of alloreactive transplants 'graft versus leukaemia (tumour) effect' from the unwanted 'graft versus host disease'. Thus, the present invention relates to a method for the production of alloreactive peptide specific CTLs.

The production of alloreactive CTLs is advantageous over autologous CTLs because a subject may be tolerant to the autologous HLA peptide combination whilst tolerance in the alloreactive setting is much less likely. Thus the present invention relates to production of CTLs against a given HLA/peptide complex from a foreign donor (alloreactive) rather than autologous.

Without being bound by theory, it may be that some HLA types can produce better reactivity against certain other HLA types. For example, making an anti-HLA-A2 response may be easier for an HLA1 background but more difficult for an HLA4 background. The methods of the present invention may be advantageously applied to the study of this phenomenon.

OBJECTS AND SUMMARY OF THE INVENTION

It will be appreciated that the invention relates to the production of alloreactive anti-peptide CTLs. Preferably the peptide is a tumour peptide or other antigenic peptide associated with a disorder such as cancer. The peptide may be a modified peptide such as a glycopeptide.

In this aspect, the invention relates to the treatment of a sample of CTLs in such a way as to promote the selection and expansion of CTLs having the desired reactivity. In this manner, alloreactive anti-peptide CTLs are advantageously produced.

In another aspect, the invention provides a method for producing antipeptide CTLs. comprising; providing a sample of peripheral blood lymphocytes (PBLs), attaching a complex of a class I HLA and a peptide to antigen presenting cell(s) (APCs) present in said PBLs, optionally removing excess class I HLA/peptide complex, and incubating with proliferative cytokine.

In a further aspect, the invention provides a method as described above wherein the APC is a B-cell.

The invention also provides a method as described above wherein the complex is attached to the APC by attachment means comprising a molecule capable of selective binding to a B cell.

In still another aspect, the invention provides a method as described above wherein the attachment means comprises sfvSA to CD20 or CD19.

The invention additionally provides a method as described above wherein said sample of PBLs is a sample of a class I HLA negative PBLs.

In another aspect, the invention provides a method as described above wherein the class I HLA is HLA-A2.

In a further aspect, the invention provides a method as described above wherein the peptide is a tumour peptide.

In an additional aspect, the invention provides a method as described above wherein the tumour peptide is selected from the group consisting of Melan-A, WT1 and a telomerase.

The invention also provides a method as described above wherein the proliferative cytokine is a combination of IL-7 and IL-2.

In another aspect, the invention provides a method as described above wherein the incubation is about 7 days. In another aspect, the invention provides a method as described above wherein the incubation step is repeated for a further 7 days.

In another aspect, the invention provides a CTL obtainable or obtained by the methods described above, and a method of treating a subject comprising. administering a CTL as described above to said subject.

In a preferred aspect, the production of alloreactive anti-tumour CTLs is accomplished in vitro. In a further preferred aspect, the present invention relates to a method for treating a subject comprising administering to said subject a sample of alloreactive CTLs according to the present invention.

Other technology for production of alloreactive peptide specific CTLs requires mixing donor PBLs with, initially, RMA cells (mouse cancer line), CIR cells (human tumour cell), and then Drosophila cells. This is both complicated and of low efficacy. These methods are also very 'dirty' which in this context means they use cancer cells. It is clearly undesirable to use cancer cells in the production of CTLs for administration to a subject. Thus, it is an advantage of the present invention that the use of cancer cells in the production of CTLs is avoided. In a preferred aspect of the invention, only PBLs and recombinant peptides/proteins are employed in said methods.

The term "comprising" in this disclosure can mean "including" or can have the meaning commonly given to the term "comprising" in U.S. Patent Law.

Other aspects of the invention are described in or are obvious from (and within the ambit of the invention) the following disclosure.

BRIEF DESCRIPTION OF DRAWINGS

Reference is made to the following accompanying figures, incorporated herein by reference:

FIG. 10 shows a FACs analysis of the time course of binding of HLA-A2/M1 peptide complexes to HLA class I−ve cells (Daudi) via an antibody bridge, detected with an FITC conjugated anti-MHC monoclonal antibody (W6/32) (This antibody (Ancell Ltd.) recognises HLA class I that is conformationally correct.)

FIG. 11A-E shows a bar chart, four scatterplots, a further barchart, four further scatterplots, and six further scatterplots.

In more detail, FIG. 11 illustrates the result of a Tetramer FACs analysis of the cells cultured from peripheral blood cells incubated with or without the anti-CD20 B9E9-streptavidin fusion protein and HLA-A2/M1 peptide complex. The cells are dual stained with a FITC conjugated monoclonal antibody to CD8 and a PE conjugated HLA-A2 tetramer with specificity for HLA-A2/MI. FIG. 11 further shows the results of Tetramer FACs analysis of the cells cultured from PBLs incubated with either the anti-CD20 B9E9-streptavidin fusion protein alone (sample C) or the anti-CD20 B9E9-streptavidin Fusion protein plus either the HLA-A2/MI peptide complex (sample F) or the HLA-A2/BMLF1 peptide complex (sample I). Cells from these samples were then dual stained with a FITC conjugated monoclonal antibody to CD8 and a PE conjugated HLA-A2 tetramer with specificity for HLA-A2/MI or HLA-A2/BMLF1 as indicated.

DETAILED DESCRIPTION

Figure 1:
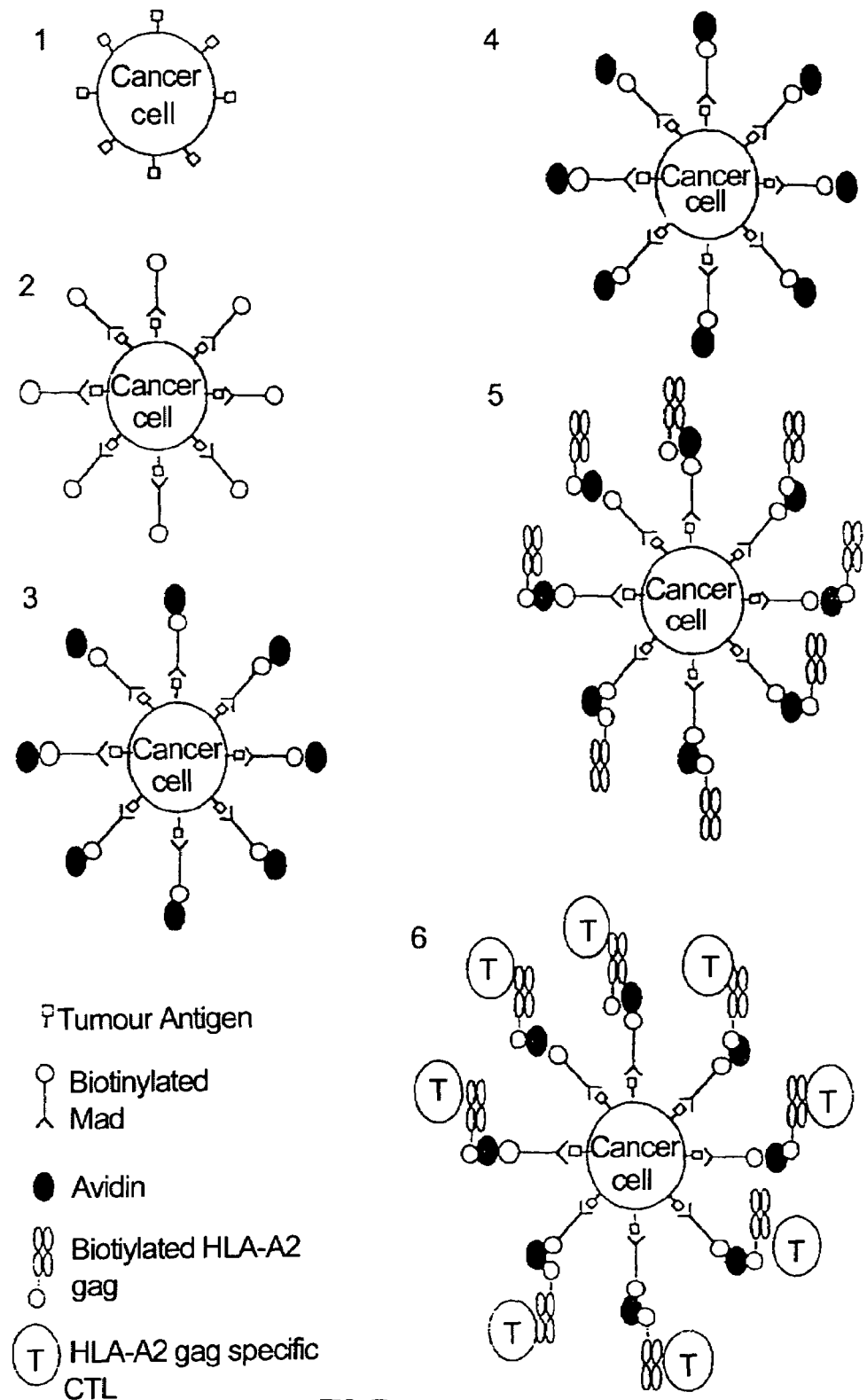
FIG. 1 shows a diagram showing the method/idea for delivering HLA molecules to the surface of tumour cells.

The present invention sets out to provide improved means for producing or enhancing an immunological response against a target cell, and to provide an improved method for treating or preventing cancer and other malignant, infectious or auto-immune diseases, conditions or symptoms.

Accordingly, in one aspect of the present invention there is provided a method for producing antipeptide CTLs comprising providing a sample of PBLs, attaching a complex of a class I HLA and a peptide to APCs present in said PBLs, optionally removing excess class I HLA/peptide complex, and incubating with proliferative cytokine.

In another aspect of the present invention there is provided a method of treating a subject comprising administering a CTL obtainable or obtained by providing a sample of PBLs, attaching a complex of a class I HLA and a peptide to APCs present in said PBLs, optionally removing excess class I HLA/peptide complex, and incubating with proliferative cytokine.

HLA/Peptide Complex

The HLA class I molecule or fragment thereof may bind a peptide, which peptide is arranged to be presented for T cell recognition by said HLA class I molecule or fragment thereof. Said peptide may be attached to the HLA class molecule or fragment thereof in accordance with the method described in Garboczi (*PNAS* 89, 1992, 3429-3433).

The attaching means preferably comprises a linking polypeptide with high specific affinity for a target cell specific molecule on the surface of the target cell. By "target cell specific molecule" herein is meant any molecule that is characteristically expressed or over-expressed on the surface of the target cell. By way of example, in cancer cells said "target cell specific molecule" could include any of the following tumour associated antigens: carcinoembryonicantigen, placental alkaline phosphatase, polymorphic epithelial mucin, human chorionic gonadotrophin, CD20, prostate specific antigen, ca-125, HMW-MAA and others.

Conveniently, the linking polypeptide will comprise an antibody, preferably a monoclonal antibody, raised against said target cell specific molecule (Riethmuller and Johnson, *Curr. Opin. Immunol.* 4, 1992, 647-655). Suitable antibodies for this purpose include C46, 85A12, H17E2, HMFGI, W14, 1F5, 225.28s (Buraggi 1985 *Cancer Res.* 45. 3378-3387), and others. Deposits of the immortalised hybrids producing these antibodies have been made at the American Type Culture Collection, 10801 University Boulevard, Manassas, Va. 20110-2209. Further examples of antibodies are described in Maloney et al (*Blood* 84, 1994, 2457-2466), Riethmuiler et al (*Lancet* 343, 1994, 1177-1183) and Hird et al (*Br. J. Cancer* 68 1993,403-406).

Said linking polypeptide may comprise an antibody raised against a target cell specific molecule and a coupling system for coupling said antibody to said HLA class I molecule or fragment thereof. The coupling system may comprise a two- or three-step chain of well-characterised paired small molecules, joined to the antibody and the HLA class I molecule so as to form a stable bridge between the two. Examples of paired small molecules which might be used in this connection include (but are not limited to) biotin and avidin/streptavidin (Moro, 1997 *Cancer Res.* 57, 1922-1928; Altman et al, *Science* 274, 1996, 9496), and calmodulin and calmodulin binding peptides (Neri, 1996, *J. Invest. Dermatol.* 107, 164-170). Alternatively, said linking polypeptide may comprise an antibody-raised against a target cell specific molecule, which. antibody is adapted to be attached directly to said HLA class I molecule or fragment thereof.

In a further possible embodiment of the invention, said complex may comprise a recombinant protein, which recombinant protein includes a moiety comprising said HLA class I molecule or fragment thereof, and a moiety comprising said attaching means.

The HLA class I molecule or fragment thereof may be purified from plasma or platelets or made recombinantly. The HLA class I molecule or fragment thereof may further be arranged to bind and present for T cell recognition a defined peptide of choice, such as a viral, bacterial, parasitic, or tumour-specific peptide. Attachment of the HLA class I molecule or fragment thereof to the target cell may be achieved by introducing said HLA class I molecule or fragment thereof and said attaching means to the vicinity of the target cell. The target cell may be a culture cell in vitro, but will advantageously be in the body of a patient. Preferably, the target cell will be arranged to be contacted by a cytotoxic T cell, which cytotoxic T cell is adapted to recognise said HLA class I molecule or fragment thereof either as being of a mismatched allotype or as binding a foreign peptide, and which cytotoxic T cell is capable of triggering an immunological response against said target cell.

The HLA/peptide complex for use in production of alloreactive CTLs may be any HLA/peptide complex that is of immunological interest. In a preferred embodiment, the HLA used in the complex is the same HLA for which the PBLs (i.e.

the CTLs) are negative. Preferably, the HLA is a class I HLA. Preferably the class I HLA comprises one or more of HLA-A1, HLA-A2, HLA-A3 or HLA-B7. In a preferred embodiment, the HLA is HLA-A2. Thus, in a highly preferred embodiment, the CTLs are HLA-A2 negative and the HLA in the complex is HLA-A2. Specific examples of HLA/peptide complexes include, but are not limited to, HLA class I/telomerase (pan tumor), HLA-A2/melan A (melanoma), HLA-A2/WT1 (leukaemia), or any other peptides of interest. Further examples of peptides of interest are given in Tables 1-7.

TABLE 1

Class I HLA-restricted cancer/testis antigens (SEQ ID NOS: 7-37). All these antigens were found to be expressed by normal spermatocytes and/or spermatogonia of testis. Occasionally MAGE-3, MAGE-4 and the GAGE genes were found to be expressed also in placenta. The NY-ESO-1 antigen was found to be expressed in normal ovary cells.

| Gene | HLA allele | Peptide epitope | Author | Tissue distribution among tumorsa |
|---|---|---|---|---|
| MAGE-A1 | A1 | EADPTGHSY | Traversari et al., 1992 | Melanoma, breast carcinoma, SCLC - |
| MAGE-A1 | A3 | SLFRAVITK | Chaux et al., 1999a | sarcoma, NSCLC - thyroid medullary |
| MAGE-A1 | A24 | NYKHCFPEI | Fujie et al., 1999 | carcinoma - colon carcinoma - |
| MAGE-A1 | A28 | EVYDGREHSA | Chaux et al., 1999a | laryngeal tumors |
| MAGE-A1, -A2-A3, -A6 | B37 | REPVTKAEML | Tanzarella et al., 1999 | Melanoma, colon and breast carcinomas, SCLC - sarcoma, NSCLC - thyroid medullary carcinoma, H/N tumors, bronchial SCC - laryngeal tumors - leukemias |
| MAGE-A1 | B53 | DPARYEFLW | Chaux et al., 1999a | Melanoma, breast carcinoma, SCLC - |
| MAGE-A1 | Cw2 | SAFPTTINF | Chaux et al., 1999a | sarcoma, colon carcinoma, NSCLC - |
| MAGE-A1 | Cw3 | SAYGEPRKL | Chaux et al., 1999a | thyroid medullary carcinoma |
| MAGE-A1 | Cw16 | SAYGEPRKL | van der Bruggen et al., 1994b | |
| MAGE-A2 | A2 | KMVELVHFL | Visseren et al., 1997 | Melanoma, colon and breast carcinomaa, |
| MAGE-A2 | A2 | YLQLVFGIEV | Visseren et al., 1997 | SCLC - sarcoma, NSCLC - thyroid medullary |
| MAGE-A2 | A24 | EYLQLVFGI | Tahara et al., 1999 | Carcinoma - laryngeal tumors - leukemias |
| MAGE-A3 | A1 | EVDPIGHLY | Gaugler et al., 1994 | Melanoma, colon and breast carcinomas - |
| MAGE-A3 | A2 | FLWGPRALV | van der Bruggen et al., 1994a | H/N tumors - bronchial SCC, thyroid |
| MAGE-A3 | A24 | TFPDLESEF | Oiso et al., 1999 | medullary and bladder carcinoma, |
| MAGE-A3 | A24 | IMPKAGLLI | Tanaka et al., 1997 | sarcomas, SCLC, NSCLC - leukemias |
| MAGE-A3 | B44 | MEVDPIGHLY | Herman et al., 1996 | |
| MAGE-A3 | B52 | WQYFFPVIF | Fleischhauer et al., 1996 Russo et al. 2000 | |
| MAGE-A4 | A2 | GVYDGREHTV | Duffour et al., 1999 | Melanoma, NSCLC, sarcomas, esophageal, colon and breast carcinomas |
| MAGE-A6 | A34 | MVKISGGPR | Zorn and Hercend, 1999b | Melanoma, NSCLC, colon carcinoma, leukemias |
| MAGE-A10 | A2 | GLYDGMEHL | Huang et al., 1999 | Not defined |
| MAGE-A12 | Cw7 | VRIGHLYIL | Panelli et al., 2000, Heidecker et al., 2000 | Melanoma, myeloma, brain tumors, sarcoma, leukemias, SCLC, NSCLC, H/N tumors, bladder, lung, esophageal, breast, prostate and colorectal carcinoma |
| BAGE | Cw16 | AARAVFLAL | Boël et al., 1995 | Melanoma, bladder and mammary carcinomas, H/N SCC, NSCLC, sarcoma |
| DAM-6, -10 | A2 | FLWGPRAYA | Fleischhauer et al., 1998 | Melanoma, skin tumors, mammary and ovarian carcinomas - lung carcinoma - seminomas |
| GAGE-1, -2, -8 | Cw6 | YRPRPRRY | Van den Eynde et al., 1995 De Backer et al. 1999 | Melanoma, sarcoma, NSCLC, SCLC, mesothelioma, sarcoma, seminoma, leukemias, lymphomas, H/N tumors, bladder, esophageal, mammary, colon, prostate carcinomas |
| GAGE-3, -4, -5, -6, -7B | A29 | YYWPRPRRY | De Backer et al. 1999 | Melanomas, H/N tumors, leukemias, esophageal, lung and bladder carcinomas |
| NA88-A | B13 | MTQGQHFLQKV | Moreau-Aubry et al., 2000 | Melanoma |
| NY-ESO-1 | A2 | SLLMWITQCFL | Jäger et al., 1998 | Melanoma, sarcoma, B-lymphomas, |
| NY-ESO-1a (CAG-3) | A2 | SLLMWITQC | Jäger et al., 1998 | hepatoma, H/N tumors, bladder, lung, |
| | A2 | QLSLLMWIT | Jäger et al., 1998 | prostate, ovarian, thyroid and breast |
| | A31 | ASGPGGGAPR | Wang et al., 1998b | carcinoma |

Tissue distribution among tumors as described in the given references when different from the paper first reporting the sequence of the epitope.

TABLE 2

Class I HLA-restricted melanocyte differentiation antigens
(SEQ ID NOS: 38-76). These antigens can only be expressed in normal
and neoplastic cells of the same lineage (namley melanocytes, skin,
retina, peripheral ganglia) or in normal cells of the prostate gland.

| Gene | HLA allele | Peptide epitope | Authors |
|---|---|---|---|
| MART-1/Melan-A[a] | A2 | AAGIGILTV | Coulie et al. 1994 |
| | | | Kawakami et al., 1994a |
| | A2 | EAAGIGILTV | Schneider et al., 1998 |
| | A2 | ILTVILGVL | Castelli et al., 1995 |
| | B45 | AEEAAGIGIL | Schneider et al., 1998 |
| | B45 | AEEAAGIGILT | Schneider et al., 1998 |
| MC1R | A2 | TILLGIFFL | Salazar-Onfray et al., 1997 |
| | A2 | FLALIICNA | Salazar-Onfray et al., 1997 |
| Gp100 | A2 | KTWGQYWQV | Bakker et al., 1995 |
| | A2 | AMLGTHTMEV | Tsai et al., 1997 |
| | A2 | MLGTHTMEV | Tsai et al., 1997 |
| | A2 | SLADTNSLAV | Tsai et al., 1997 |
| | A2 | ITDQVPFSV | Kawakami et al., 1995 |
| | A2 | LLDGTATLRL | Kawakami et al, 1994b |
| | A2 | YLEPGPVTA | Cox et al., 1994 |
| | A2 | VLYRYGSFSV | Kawakami et al., 1995 |
| | A2 | RLMKQDFSV | Kawakami et al., 1998 |
| | A2 | RLPRIFCSC | Kawakami et al., 1998 |
| | A3 | LIYRRRLMK | Kawakami et al., 1998 |
| | A3 | ALNFPGSQK | Kawashima et al., 1998 |
| | A3 | SLIYRRRLMK | Kawashima et al, 1998 |
| | A3 | ALLAVGATK | Skipper et al., 1996 |
| | A24 | VYFFLPDHL | Robbins et al., 1997 |
| | Cw8 | SNDGPTLI | Castelli et al., 1999 |
| PSA | A1 | VSHSFPHPLY | Corman et al., 1998 |
| | A2 | FLTPKKLQCV | Correale et al., 1997 |
| | A2 | VISNDVCAQV | Correale et al., 1997 |
| PSM | A1 | HSTNGVTRIY | Corman et al., 1998 |
| Tyrosinase | A1 | KCDICTDEY | Kittlesen et al., 1998 |
| | A1 | SSDYVIPIGTY | Kawakami et al., 1998 |
| | A2 | YMDGTMSQV | Wölfel et al., 1994 |
| | A2 | MLLAVLYCL | Wölfel et al., 1994 |
| | A24 | AFLPWHRLF | Kang et al., 1995 |
| | B44 | SEIWRDIDF | Brichard et al., 1996 |
| TRP-1 (or gp75) | A31 | MSLQRQFLR | Wang et al., 1996b |
| TRP-2 | A2 | SVYDFFVWL | Parkhurst et al., 1998 |
| | A2 | TLDSQVMSL | Noppen et al., 2000 |
| | A31 | LLGPGRPYR | Wang et al., 1996a |
| | A33 | LLGPGRPYR | Wang et al, 1998a |
| | Cw8 | ANDPIFVVL | Castelli et al., 1999 |

[a] Two different groups simultaneously discovered this gene and gave it two different names, MART-1 and Melan-A respectively.

TABLE 3

Class I HLA-restricted widely expressed antigens.
(SEQ ID NOS: 77-106).

| Gene | HLA allele | Peptide epitope | Tissue distribution | | Reference |
|---|---|---|---|---|---|
| | | | Tumors | Normal tissues | |
| ART-4 | A24 | AFLRHAAL DYPSLSATDI | SCC, SCLC, H/N tumors, leukemia, lung, esophageal, gastric, cervical, endometrial, ovarian and breast carcinomas | Testis, placenta, fetal liver | Kawano et al, 2000 |
| CAMEL | A2 | MLMAQEALAFL | Melanoma | Testis, placenta, heart, skeletal muscle, pancreas | Aarnoudse et al., 1999 |
| CEA | A2 | YLSGANLNL (CAP-1)[a] | Melanoma | Testis, placenta, heart, skeletal muscle, pancreas | Tsang et al., 1995 |
| CEA | A3 | HLFGYSWYK | Colon, rectum, pancreas, gastric, breast and lung carcinomas | Gastrointestinal embryonic tissue | Kawashima et al., 1999 |
| Cyp-B | A24 | KFHRVIKDF DFMIQGGDF | Lung adenocarcinoma, T cell leukemia, lymphosarcoma - bladder, ovarian, uterine and esophageal SCC | Ubiquitously expressed in normal tissues. | Gomi et al., 1999 |
| HER2/neu | A2 | KIFGSLAFL | Melanoma - ovarian and breast carcinomas | Epithelial cells | Fisk et al., 1995 |
| HER2/neu | A2 | IISAVVGIL | Melanoma, ovarian, pancreatic[b] and breast carcinomas | Epithelial cells | Peoples et al, 1995 |
| HER2/neu | A2 | RLLQETELV | Melanoma, ovarian, gastric, pancreatic and breast carcinomas | Epithelial cells | Kono et al., 1998 |
| HER2/neu | A2 | VVLGVVFGI ILHNGAYSL YMIMVKCWMI | Melanoma, ovarian, gastric, pancreatic and breast carcinomas | Epithelial cells | Rongcun et al., 1999 |
| HER2/neu | A3 | VLRENTSPK | Melanoma, ovarian, gastric, pancreatic and breast carcinomas | Epithelial cells | Kawashima et al., 1999 |
| hTERT[c] | A2 | ILAKFLHWL | Lung and ovarian carcinomas - multiple myeloma, melanoma, sarcoma, acute leukemias, non-Hodgkin's lymphomas | Hematopoietic stem cells and progenitors; germinal center cells; basal keratinocytes; gonadal cells; certain proliferating epithelial cells | Vonderheide et al., 1999 |
| hTRT[c] | A2 | ILAKFLHWL RLVDDFLLV | Lung, prostate and ovarian carcinomas, multiple myeloma, melanoma, sarcoma, acute leukemias, non-Hodgkin's lymphomas | Circulating B cells; germinal center B cells; thymocytes; CD34+ progenitor hematopoietic cells | Minev et al., 2000 |

TABLE 3-continued

Class I HLA-restricted widely expressed antigens.
(SEQ ID NOS: 77-106).

| Gene | HLA allele | Peptide epitope | Tissue distribution | | |
|---|---|---|---|---|---|
| | | | Tumors | Normal tissues | Reference |
| iCE | B7 | SPRWWPTCL | RCC | Kidney, colon, small intestine, liver, heart, pituitary gland, adrenal gland, prostate, stomach | Ronsin et al., 1999 |
| MUC1 | A11 | STAPPAHGV | Breast and ovarian carcinomas, multiple myeloma, B-cell lymphoma | None[d] | Domenech et al. 1995 |
| MUC1 | A2 | STAPPVHNV | Breast and ovarian carcinoma, multiple myeloma, B-cell lymphoma | None[d] | Brossart et al., 1999 |
| MUC2 | A2 | LLNQLQVNL MLWGWREHV | Ovary, pancreas and breast mucinous tumors, colon carcinoma of non-mucinous type | Colon, small intestine, bronchus, cervix and gall bladder | Böhm et al., 1998 |
| PRAME | A24 | LYVDSLFFL | Melanoma, H/N and lung SCC, NSCLC, RCC, adenocarcinoma, sarcoma, leukemias | Testis, endometrium, ovary, adrenals, kidney, brain, skin | Ikeda et al., 1997 |
| P15 | A24 | AYGLDFYIL | Melanoma | Testis, spleen, thymus, liver, kidney, adrenal tissue, lung tissue, retinal tissue | Robbins et al., 1995 |
| RU1 | B51 | VPYGSFKHV | Melanoma, renal and bladder carcinomas | Testis, kidney, heart, skin, brain, ovary, liver, lung, lymphocytes, thymus, fibroblasts | Morel et al, 2000 |
| RU2 | B7 | LPRWPPPQL | Melanoma, sarcomas, leukemia - brain, esophageal and H/N tumors - renal, colon, thyroid, mammary, bladder, prostatic and lung carcinomas | Testis, kidney, liver, urinary bladder | Van den Eynde et al. 1999 |
| SART-1 | A24 | EYRGFTQDF | Esophageal, H/N and lung SCC - adenocarcinoma, uterine cancer | Testis, fetal liver | Kikuchi et al, 1999 |
| SART-1 | A*2601 | KGSGKMKTE | Esophageal, H/N and lung SCC, adenocarcinoma, uterine cancer | Testis, fetal liver | Shichijo et al., 1998 |
| SART-3 | A24 | VYDYNCHVDL AYIDFEMKI | H/N, esophageal and lung SCC, adenocarcinoma, leukemia, melanoma | Lymphoid cells, fibroblasts, testis, fetal liver | Yang et al., 1999 |
| WT1 | A2 | RMFPNAPYL | Gastric, colon, lung, breast, ovary, uterine, thyroid and hepatocellular carcinomas - leukemia (including AML, ALL and CML) | Kidney, ovary, testis, spleen | Oka et al., 2000 |

[a]CAP-1 is an alternative name of this peptide.
[b]Tissue distribution among tumors as described in the given references when different from the paper first reporting the sequence of the epitope.
[c]Telomerase is expressed in most human tumors: those listed were shown to be susceptible to lysis by cytotoxic T lymphocytes.
[d]All epithelial tissues express mucin like hyperglycosylated molecules.

TABLE 4

Class I HLA-restricted tumor specific antigens, including both unique (CDK-4, MUM-1, MUM-2, β-catenin, HLA-A2-R170I, ELF2m, myosin-m, caspase-8, KIAA0205, HSP70-2m) and shared (CAMEL, TRP-2/INT2, GnT-V, G 250) antigens.
(SEQ ID NOS: 107-128).

| Gene | HLA allele | Peptide epitope | Tissue distribution | | |
|---|---|---|---|---|---|
| | | | Tumors | Normal tissues | Reference |
| AFP | A2 | GVALQTMKQ | Hepatocellular carcinoma | Fetal liver | Butterfield et al, 1999 |
| β-catenin/m | A24 | SYLDSGIHF | Melanoma | None | Robbins et al. 1996 |
| Caspase-8/m | B35 | FPSDSWCYF | H/N tumors | None | Mandruzzato et al., 1997 |
| CDK-4/m | A2 | ACDPHSGHFV | Melanoma | None | Wölfel et al., 1995 |
| ELF2M | A68 | ETVSEQSNV | Lung SCC | None | Hogan et al., 1998 |
| GnT-V | A2 | VLPDVFIRC(V)[a] | Melanoma, brain tumors, sarcoma | Breast and brain (low expression) | Guilloux et al., 1996 |
| G250 | A2 | HLSTAFARV | RCC, colon, ovarian and cervical carcinomas | None | Vissers et al., 1999 |
| HA-A*0201-R170I | A2 | CVEWLRIYLENGK | RCC | None | Brandle et al., 1996 |
| HSP70-2M | A2 | SLFEGIDIY | RCC, melanoma, neuroblastoma | None | Gaudin et al., 1999 |
| HST-2 | A31 | YSWMDISCWI | Gastric signet cell carcinoma | None | Suzuki et al., 1999 |
| KIAA0205 | B44*03 | AEPINIQTV | Bladder cancer | None | Gueguen et al., 1998 |
| MUM-1 | B44 | EEKLIVVLF | Melanoma | None | Coulie et al., 1995 |
| MUM-2 | B44 | SELFRSGLDY | Melanoma | None | Chiari et al., 1999 |
| MUM-2 | Cw6 | FRSGLDSYV | Melanoma | None | Chiari et al., 1999 |

TABLE 4-continued

Class I HLA-restricted tumor specific antigens, including both unique (CDK-4, MUM-1, MUM-2, β-catenin, HLA-A2-R170I, ELF2m, myosin-m, caspase-8, KIAA0205, HSP70-2m) and shared (CAMEL, TRP-2/INT2, GnT-V, G 250) antigens.
(SEQ ID NOS: 107-128).

| Gene | HLA allele | Peptide epitope | Tissue distribution | | Reference |
|---|---|---|---|---|---|
| | | | Tumors | Normal tissues | |
| MUM-3 | A28 | EAFIQPITR | Melanoma | None | Baurain et al., 2000 |
| Myosin/m | A3 | KINKNPKYK | Melanoma | None | Zom and Hercend, 1999a |
| RAGE | B7 | SPSSNRIRNT | Melanoma, sarcomas, mesotheliomas, H/N tumors, bladder, renal, colon and mammary carcinomas | Retina only | Gaugler et al., 1996 |
| SART-2 | A24 | DYSARWNEI AYDFLYNYL SYTRLFLIL | H/N and lung SCC, lung adenocarcinoma, RCC, melanoma, brain tumors, esophageal and uterine cancers | None | Nakao et al., 2000 |
| TRP-2/INT2 | A68 | EVISCKLIKR | Melanoma | None | Lupetti et al., 1998 |
| TRP-2/INT2 | A68 | EVISCKLIKR | Melanoma | None | Lupetti et al., 1998 |
| 707-AP | A2 | RVAALARDA | Melanoma | None[b] | Morioka et al., 1995 |

[a]VLPDVFIRC(V) = nonamer and decamer peptides are both recognized by CTLs.
[b]This antigen is not expressed in normal cells but, as the tissue of the testis was not tested, it will not become clear to which category the antigen may belong until more information is available.

TABLE 5

Class II HLA-restricted antigens.
SEQ ID NOS: 129-154).

| Gene | HLA- allele | Peptide epitope | Tissue expression | | Reference |
|---|---|---|---|---|---|
| | | | Tumors | Normal tissues | |
| Epitopes from normal protein antigens | | | | | |
| Annexin II | DRB*0401 | DVPKWISIMTERSVPH | Melanoma | Not done | Li et al., 1998 |
| Gp100 | DRB1*0401 | WNRQLYPEWTEAQRLD | Melanoma | Melanocytes | Li et al., 1998 |
| MAGE-1, -2, -3, -6 | DRB*1301, DRB*1302 | LLKYRAREPVTKAE | Melanoma, lung and breast carcinomas, H/N SCC | Testis, placenta | Chaux et al.; 1999a |
| MAGE-3 | DR*1101 | TSYVKVLHHMVKISG | Melanoma, lung and breast carcinomas, H/N SCC | Testis, placenta | Manici et al., 1999 |
| MAGE-3 | DRB*1301, DRB*1302 | AELVHFLLLKYRAR | Melanoma, lung and breast carcinomas, H/N SCC | Testis, placenta | Chaux et al., 1999b |
| MART-1/Melan-A | DRB1*0401 | RNGYRALMDKSLHVGTQCALTRR | Melanoma | Melanocytes | Zarour et al., 2000 |
| MUC1 | DR3 | PGSTAPPAHGVT | Breast and ovarian cancers, multiple myeloma, B-cell lymphoma | None[a] | Hiltbold et al., 1998 |
| NY-ESO-1 | DRB4*0101 | VLLKEFTVSG | Melanoma, B-lymphoma, hepatoma[b], sarcoma, H/N tumors, -bladder, lung, prostate, ovarian, thyroid and breast carcinomas | Testis | Zeng et al., 2000 |
| NY-ESO-1 | DRB4*0101-0103 | PLPVPGVLLKEFTVSGNI VLLKEFTVSGNILTIRLT AADHRQLQLSISSCLQQL | B-lymphoma, melanoma, sarcoma, H/N tumors, hepatoma -bladder, lung, prostate, ovarian, thyroid and breast carcinomas | Testis | Jäger et al. 2000 |
| PSA | DR4 | ILLGRMSLFMPEDTG SLFHPEDTGQVFQ QVFQVSHSFPHPLYD NDLMLLRLSEPAELT KKLQCVQLHVISM GVLQGITSMGSEPCA | Prostate carcinoma | Prostate gland | Corman et al., 1998 |
| Tyrosinase | DRB1*0401 | QNILLSNAPLGPQFP DYSYLQDSDPDSFQD SYLQDSDPDSFQD | Melanoma | Melanocytes | Topalian et al., 1994 Topalian et al., 1996 |

TABLE 5-continued

Class II HLA-restricted antigens.
SEQ ID NOS: 129-154).

| Gene | HLA-allele | Peptide epitope | Tumors | Tissue expression Normal tissues | Reference |
|---|---|---|---|---|---|
| Tyrosinase | DRB1*1501 | RHRPLQEVYPEANAPIGHNRE | Melanoma | Melanocytes | Kobayashi et al., 1998a |
| Tyrosinase | DRB1*0405 | EIWRDIDFAHE | Melanoma | Melanocytes | Kobayashi et al, 1998b |
| | | Epitopes from mutated protein antigens | | | |
| HPV-E7 | DR*0401, DR*0407 | LFMDTLSFVCPLC LFMDSLNFVCPWC | Cervical carcinoma | None | Höhn et al., 1999 |
| CDC27/m | DRB1*0401 | FSWAMDLDPKGA | Melanoma | None | Wang et al., 1999a |
| TPI/m | DRB1*0101 | GELIGILNAAKVPAD | Melanoma | None | Pieper et al., 1999 |

[a]All epithelial tissues express highly glycosilated mucins whereas tumor cells often show hypoglycosilated mucins with a normal protein sequence.
[b]Tissue distribution among tumors as described in the given references when different from the paper first reporting the sequence of the epitope.

TABLE 6

Epitopes derived from fusion proteins (fusion proteins are never found in normal tissues)
(SEQ ID NOS: 155-177).

| Gene | HLA allele | Peptide epitope | Tissue distribution among tumors | Reference |
|---|---|---|---|---|
| | | HLA class I restricted epitopes | | |
| bcr-abl[a] | A2 | FMVELVEGA KLSEQESLL MLTNSCVKL | CML | Buzyn et al., 1997 |
| bcr-abl p210(b3a2) | A2 | SSKALQRPV | CML | Yotnda et al., 1998a |
| bcr-abl (b3a2) | A3 | ATGFKQSSK KQSSKALQR | CML | Greco et al., 1996 |
| bcr-abl p210 (b3a2) | A3, A11 | HSATGFKQSSK | CML | Bocchia et al., 1996 |
| bcr-abl p210(b3a2) | A3 | KQSSKALQR | CML | Norbury et al., 2000 |
| bcr-abl p210(b3a2) | B8 | GFKQSSKAL | CML | Norbury et al., 2000 |
| ETV6/AML | A2 | RIAECILGM | ALL | Yotnda et al., 1998b |
| | | HLA class II restricted epitopes | | |
| bcr-abl p190 (e1a2) | DRB1*1501 | EGAFHGDAEALQRPVAS | ALL | Tanaka et al., 2000 |
| bcr-abl p210 (b2a2) | DRB5*0101 | IPLTINKEEALQRPVAS | CML | ten Bosch et al., 1999 |
| bcr-abl p210 (b3a2) | DRB1*0401 | ATGFKQSSKALQRPVAS | CML | ten Bosch et al., 1996 |
| bcr-abl p210 (b3a2) | DRB1*1501 | ATGFKQSSKALQRPVAS | CML | ten Bosch et al., 1995 |
| bcr-abl (b3a2) | DRB1*0901 | ATGFKQSSKALQRPVAS | CML | Yasukawa et al., 1998 |
| bcr-abl (b3a2) | DRB1*1101 | LIVVIVHSATGFKQSSKALQRPVA | CML | Pawelec et al., 1996 |
| bcr-abl (b3a2) | DR11 | IVHSATGFKQSSKALQRPVASDFEP | CML | Bocchia et al., 1996 |
| Dek-cain | DRB4*0103 | TMKQICKKEIRRLHQY | AML | Ohminami et al., 1999 |
| LDLR/FUT | DRB1*0101 | GGAPPVTWRRAPAPG WRRAPAPGAKAMAPG | Melanoma | Wang et al., 1999b |
| Pml/RARα | DR11 | NSNHVASGAGEAAIETQSSSSEEIV | APL | Gambacorti-Passerini et al., 1993 |
| p190 minor bcr-abl (e1a2) | DRB1*1501 | EGAFHGDAEALQRPVAS | AML | Tanaka et al., 2000 |
| TEL/AML1 | DP5, DP17 | IGRIAECILGMNPSR | AML | Yun et al., 1999 |

[a]These bcr-abl epitopes are not true fusion proteins generated-epitopes, because they derive from outside the bcr-abl junction

TABLE 7

Frequency of epitopes recognized by a given HLA allele.

| Antigen | No. of epitopes | HLA-A | HLA-B | HLA-C |
|---|---|---|---|---|
| MAGE-1, -2, -3, -4, -6, -10, -12 | 24 | 13 (54%) | 7 (29%) | 4 (17%) |
| GAGE-1, -2, -3, -4, -5, -6, -7B, -8 | 8 | 5 (62.5%) | 0 | 3 (37.5%) |
| MART-1 | 6 | 4 (67%) | 2 (33%) | 0 |
| Gp100 | 12 | 11 (92%) | 0 | 1 (8%) |
| Tyrosinase | 6 | 5 (83%) | 1 (17%) | 0 |

Attachment

In this embodiment of the invention, the attachment means is capable of selectively binding to an APC, and to the HLA/peptide complex. Preferably the APC is a B cell. Preferably the complex is attached to the APC by attachment means comprising a molecule capable of selective binding to a B cell. Preferably the attachment means comprises sfvSA to CD20 or CD19. Preferably the attachment means comprises sfvSA to CD20, such as the B9E9 moiety.

Target Cells

In one embodiment of the present invention the target cell is of a type which may be lysed as a result of an immunological response thereagainst. Advantageously, the target cell is a tumour cell or any diseased or foreign cell the presence of which is undesired in a patient, such as a cancer cell, leukaemia cell, a cell infected with the HIV virus or with any other microbe or virus, a cell responsible for detrimental activity in auto-immune disease, and so on. In order to accelerate the triggering of an immunological response against said target cell in a patient, said HLA class I molecule or fragment thereof will preferably be capable of producing a powerful immune response from the cellular immune system of the patient. Accordingly, said HLA class I molecule or fragment thereof may bind a viral or microbial peptide, preferably a viral or microbial peptide to which the patient is likely to have had previous exposure. In particular, said HLA class I molecule or fragment thereof may bind an influenza virus peptide, a measles virus peptide, an Epstein-Barr virus peptide, in particular an Epstein-Barr virus peptide comprising the RAKFFQLL (SEQ ID NO: 1) epitope of the lytic protein BZLFI, a Cytomegalovirus peptide, or a tetanus toxoid peptide. Alternatively, said HLA class I molecule or fragment thereof may bind any peptide which already has a strong cytotoxic T cell response or which is capable of inducing a powerful immune response. The allotype of said HLA class I molecule or fragment thereof may additionally be different from the allotype of the HLA class I molecules of the patient, so that an alloreactive response may additionally be triggered against said target cell.

In another embodiment of the invention the target cell is an antigen presenting cell (APC). Recognition by a cytotoxic T cell of an HLA class I molecule or fragment thereof attached to said APC may result in direct and selective proliferation of the cytotoxic T cell. Accordingly, said HLA class I molecule or fragment thereof will advantageously be adapted to present for T cell recognition a tumour specific peptide as defined above, or a viral peptide, or a bacterial peptide, or a parasitic peptide, or any peptide which is exclusively or characteristically presented by HLA class I molecules on the surface of diseased, malignant or foreign cells the presence of which is undesirable in a patient. Peptides linked to malignant conditions have been characterised (Brossart, 1998 *Cancer Res.* 58. 732-736 and Lucas, 1998 *Cancer Res.* 58, 743752), as have peptides of parasitic origin (Khusmith, 1991 *Science* 252, 715718). The attachment of an HLA class I molecule or fragment thereof to an APC, in accordance with the present invention, may be used for in vivo immunisation against cells presenting a given peptide, or ex vivo production of cytotoxic T cells of a particular specificity.

Where the target cell is a tumour cell or microbially infected cell, the pharmaceutical composition of the present invention may be used for the treatment of a tumour or microbial disease respectively, and there is provided a method of treating a tumour or microbial disease in a patient, comprising the step of administering to a patient in need thereof an effective amount of said pharmaceutical composition.

It must be noted that whilst many tumour types express tumour associated antigens, heterogeneity in the level of expression does occur, so some tumour cells may not be targeted by antibody and lysed directly. However, in vitro date from the analogous antibody-superantigen system shows that the high local levels of cytokines released by activated T cells can lead to the death of untargeted bystander tumour cells (Dohlsten et al, *Int. J. Cancer* 54, 1993, 482488). It is likely that similar effects will occur in a targeting system using MHC class I/peptide complexes. Similarly, it is possible that the presence of activated cytotoxic T cells releasing cytokines in the tumour may lead to enhancement of a specific anti-tumour immune response. Where the target cell is an APC and the HLA class I molecule or fragment thereof binds a tumour-specific peptide or any peptide which is exclusively or characteristically presented by HLA class I molecules on the surface of a virally, bacterially, parasitically or microbially infected cell, the pharmaceutical composition of the present invention may be used for immunising against the tumour or viral, bacterial, parasitic or microbial infection respectively, and there is provided a method of immunising against a tumour or viral, bacterial, parasitic or microbial infection in a patient, comprising the step of administering to a patient in need thereof an effective amount of said pharmaceutical composition.

The response of said patient may be improved by in vivo cytokine support, or by the infusion of antigen-specific cytotoxic T cells expanded ex vivo. Transient immunosuppression (Ledermann at al, *Int. J. Cancer* 47, 1991, 659664) may be used to minimise the immunogenic response of a patient to components of the targeting system such as the avidin bridge. The administration of said pharmaceutical composition may be by way of oral, sublingual, transdermal or parenteral administration.

Said effective amount of the pharmaceutical composition will depend on factors such as the nature and severity of the disorder being treated and on the weight, age and condition of the patient.

T Cell Receptor Genes

In addition to their direct use in therapy, the alloreactive CTLs of the present invention can also be used for cloning of their T cell receptor (TCR) genes. This is preferably accomplished by methods commonly used in the art e.g. PCR amplification and cloning of the TCR genes of the alloreactive CTLs.

The T cell receptor genes obtained in accordance with the present invention find application in gene therapy, for example using TCR transfer technology, as well as for making recombinant TCR molecules for therapy, and in any other techniques making use of cloned TCR gene(s).

Preferably when the recombinant TCR molecules are used in therapy, the Avidex technology is employed to produce soluble TCR molecules (see below).

Furthermore, the dismantling of the alloreactive T cell receptor, co-receptor, and binding site on appropriate cells into their component parts is advantageously carried out. These can then be modified, for example to discover new small molecule drug candidates.

Techniques are now available to produce stable, soluble, reproducible T cell proteins that provide the same range of opportunities as monoclonal antibodies did for the humoral immune system; new protein drugs, diagnostics, reagents of importance to the pharmaceutical industry, and improvement of existing drugs by site-directed targeting are therefore within the scope of the present invention through the alloreactive CTLs provided herein.

Thus, the alloreactive T cells of the present invention may be used for the production of T cell proteins, a key component of the body's immune system, as stable compounds suitable for a broad range of clinical applications. One way in which they may be so used is through recombinant DNA technology to clone the TCRs and produce them in vitro. This is preferably accomplished following the techniques from the teachings of Bent Jakobsen et al. (Institute of Molecular Medicine, University of Oxford), and the technologies stemming from and commercially available from Avidex Limited, Abingdon, Oxfordshire, UK.

Further Applications of Alloreactive CTLs

In addition to their direct use in therapy, the alloreactive CTLs of the present invention can also be used in vitro; for example in purging cell preparations of tumour cells such as bone marrow cells. Advantageously this may be accomplished in accordance with the methods of Gao et al. (Gao et al. 2000 *Blood* 95:2198-203).

The BQ cells described herein that recognize all A2/peptide complexes are also embraced by the present invention. These cells and their TCRs are useful, for example, in preventing organ transplant rejection as soluble TCRs that block all anti-HLA-A2 cells binding transplant organ cells. They may also be used for therapy of patients who develop allogeneic tumours after organ transplant, an unusual. but acute medical problem.

Starting Material

The methods of making CTLs described herein preferably begin with a sample of peripheral blood lymphocytes (PBLs/PBMCs). In a preferred aspect, the methods of making CTLs described herein do not involve comixing of the PBLs with any further cell(s) in vitro.

In a preferred aspect of the invention, these PBLs are chosen so that they are complementary to the HLA type of the intended recipient. For example, if the intended recipient is HLA-A2, then preferably the PBLs are HLA-A2 negative so that the strongest alloreactive CTLs are produced.

It is an advantage of the present invention that the APCs used are those that are present in the starting material PBLs. In this way, the comixing of other cell(s) with the CTLs is advantageously avoided.

Expansion/Proliferation of CTLs

Expansion/proliferation of CTLs is advantageously accomplished. In this embodiment of the invention, the proliferative cytokine may be a single cytokine or a combination thereof. Preferably the proliferative cytokine is a combination of IL-7 and IL-2.

Typically, the incubation period for expansion is about 7 days. Optionally, the incubation step is repeated for about 7 further days, and may be advantageously repeated for further time periods if desired, such as a further 7 days (e.g. 21 days in total) or even more.

It will be appreciated that the present invention relates to a CTL obtainable by the methods of the present invention. Thus the invention further relates to a method of treating a subject comprising administering a CTL obtainable by the methods of the present invention to said subject.

Preferably said CTL is directly obtained by the methods of the present invention. Thus the invention further relates to a method of treating a subject comprising administering a CTL obtained by the method of the present invention to said subject.

Treatment of a Subject

It is to be appreciated that all references herein to treatment include one or more of curative, palliative and prophylactic treatment. Preferably, the term treatment includes at least curative treatment and/or prophylactic treatment.

The treatment may be of one or more of cancer, tumour or related complaint. Treatment may be for producing/enhancing/augmenting immune response(s) in malignant illnesses such as cancer/leukaemia/lymphoma. Furthermore, treatment may be for infectious diseases including HIV and leprosy.

The CTLs of the present invention may be used as therapeutic agents—i.e. in therapy applications.

As with the term "treatment", the term "therapy" includes curative effects, alleviation effects, and prophylactic effects.

The therapy may be on humans or animals.

In one aspect, CTLs are produced in vitro from donor PBLs according to the present invention. They are then expanded as described herein. Expansion may also be accomplished by any other suitable method known to those skilled in the art either in combination with or instead of the expansion techniques disclosed herein. Preferably, the expansion techniques are as disclosed herein.

Alloreactive peptide specific CTLs may then be introduced/administered into a subject. This may be by any suitable technique such as by infusion.

It will be appreciated that advantageously alloreactive CTLs from a single donor may be used to treat many different subjects. Preferably such subjects are HLA-A2 positive and the CTLs are HLA-A2 negative.

Administration

CTLs can be introduced into the subject using known methods, via various routes of administration and at various sites, e.g., renal subcapsular, subcutaneous, central nervous system (including intrathecal), intravascular, intrahepatic, intrasplanchnic, intraperitoneal (including intraomental), or intramuscular implantation. Typically, a physician or other health care provider or professional will determine the approximate cell dosage that will be most suitable for an individual subject. The specific dose for any particular subject may be varied and will depend upon a variety of factors including the age, body weight, general health, mode and time of administration and the severity of the particular condition in the subject undergoing transplantation.

The invention is now illustrated and further described by way of further examples, which should not be regarded as limiting in scope.

EXAMPLES

Example 1

The following components were used:

Target cells: A human melanoma cell line Mel 1, deposited at the Department of Immunology, Institute of Molecular Medicine, Oxford, that carries the HLA class I allotype HLA-A2. The cell line was grown in standard RPMI tissue culture media. A human melanoma cell line Mel 2, deposited at the Department of Immunology, Institute of Molecular Medicine, Oxford, that does not carry the HLA class I allotype HLA-A2. The cell line was grown in standard RPMI tissue culture media.

Attaching means: A monoclonal antibody 225.28s (Buraggi 1985 *Cancer Res.* 45 3378-3387) that binds to the HMW-MAA antigen on human melanoma cells. Biotin is chemically conjugated onto this antibody as described in Bayer 1990, *Methods Embryology* 184, 138-160.

Pure hen egg avidin obtained commercially from Societa Prodotti Antibiotics, Milan, Italy.

HLA: Biotin conjugated recombinant HLA class I allotype HLA-A2 molecules, as described in Altman 1996, *Science* 274, 94-96, further containing the "gag" peptide that is part of the HIV virus. This peptide comprises the amino acid sequence -SLYNTVATL-(SEQ ID NO: 2). Methods for the preparation/isolation thereof are described in Johnson 1991, *J Immunol* 147, 1512. The "gag" peptide was attached to the HLA-A2 molecules as described in Garboczi 1992, *PNAS* 89, 3429-3433.

T cells: HLA-A2/gag specific cytotoxic T cells obtained from an A2+ve HIV patient as described in Altman 1994, *Science* 274, 94-96.

In order to establish the ability of the attaching means to cause display of the HLA class I molecules on the surface of Mel 2 target cells, approximately 200,000 cells were first incubated with biotin conjugated monoclonal antibody 225.28s at a final concentration of 20 µg/ml at 37° C. for 30 minutes. Following this the cells were washed in tissue culture media (RPMI 1640, obtainable from Gibco, Scotland). The Mel 2 cells were then incubated with avidin at a final concentration of 10 µg/ml for 10 minutes at 37° C. and washed in tissue culture media. Finally, the Mel 2 cells were incubated with biotin conjugated HLA class I HLA-A2/gag molecules at a final concentration of 20 µg/ml at 37° C. for 20 minutes.

Figure 2:
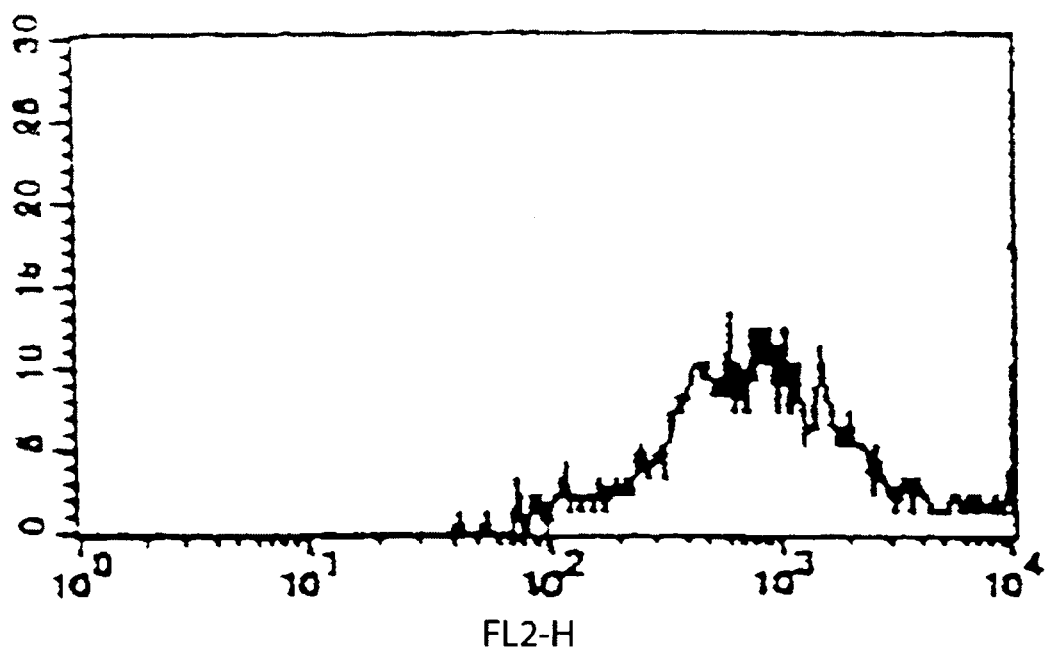
FIG. 2 shows a FACs analysis of HLA-A2 −ve Mel 2 melanoma cells treated with biotin-conjugated monoclonal antibody 225.28s, avidin, biotin-conjugated HLA-A2/gag complexes, anti-HLA-A2 monoclonal antibody BB7.2 and phycoerythrin-conjugated rabbit anti-mouse antibody.

The binding of recombinant HLA-A2 to the treated Mel 2 cells was shown by the attachment of anti-HLA-A2 monoclonal antibody BB7.2 (Santos-Aguado 1988, *J. Immunol* 141, 2811-2818) following incubation with BB7.2 antibody at a final concentration of 10 µg/ml at 37° C. for 30 minutes. After washing in tissue culture media the cells were incubated with phycoerythrin conjugated rabbit anti-mouse antibody (Sigma, Poole, UK) at a final concentration of 10 µg/ml for 30 minutes at 37° C. and analysed in a Becton Dickson Facscan machine. The result of this analysis is shown in FIG. 2 which demonstrates a positive signal indicating the presence of HLA-A2 molecules attached to the surface of the Mel 2 cells.

A chromium release T cell cytotoxicity assay was then performed in order to establish the ability of HLA-A2/gag specific T cell clones to lyse Mel 1 cells coated with HLA-A2/gag in accordance with the present method. Approximately $10^6$ Mel 1 cells were first pre-incubated with 1.85 µBq $Na_2^{51}CrO_4$ (obtained from Amersham International, Amersham, UK) for 1 hour at 37° C. The pre-incubated Mel 1 cells were then incubated with biotin conjugated monoclonal antibody 225.28s at a final concentration of 20 µg/ml at 37° C. for 30 minutes, and washed in tissue culture media. Following this, the Mel 1 cells were incubated with avidin at a final concentration of 10 µg/ml for 10 minutes at 37° C. and then washed again in tissue culture media. The Mel I cells were then incubated with biotin conjugated HLA class I HLA-A2/gag molecules at a final concentration of 20 µg/ml at 37° C. for 20 minutes and washed with tissue culture media.

Having been coated with HLA class I HLA-A2/gag, the chromium-treated Mel I cells were then incubated with HLA-A2/gag specific cytotoxic T cells in ratios of 0:1 to 20:1 of effector to target cells at 37° C. for 20 hours. Lysis of Mel I cells treated with $Na_2^{51}CrO_4$ results in the release of radioactive chromium, which may be detected by analysis in a scintillation counter. In order to establish the percentage of Mel 1 cells lysed following incubation with HLA-A2/gag specific cytotoxic T cells, the following measurements were taken: background release of chromium from the Mel I cells in media alone ("M"); release of chromium from the Mel 1 cells following incubation with the T cells ("E"); release of chromium from the Mel I cells following final treatment with 5°/o Triton X-100 detergent ("T"). Treatment with detergent will cause the lysis of all the remaining intact Mel 1 cells.

% Mel 1 lysis by cytotoxic T cells was calculated as follows:

$$\% \text{ lysis} = 100 \times \frac{(E - M)}{(T - M)}$$

This analysis was carried out on Mel 1 cells treated with biotin-conjugated 225.28s, avidin, and biotin-conjugated HLA-A2/gag. As a control, the analysis was also carried out on Mel 1 cells treated with biotin-conjugated 225.28s and avidin alone, and on Mel 1 cells treated with avidin and biotin-conjugated HLA-A2/gag alone.

Figure 3:
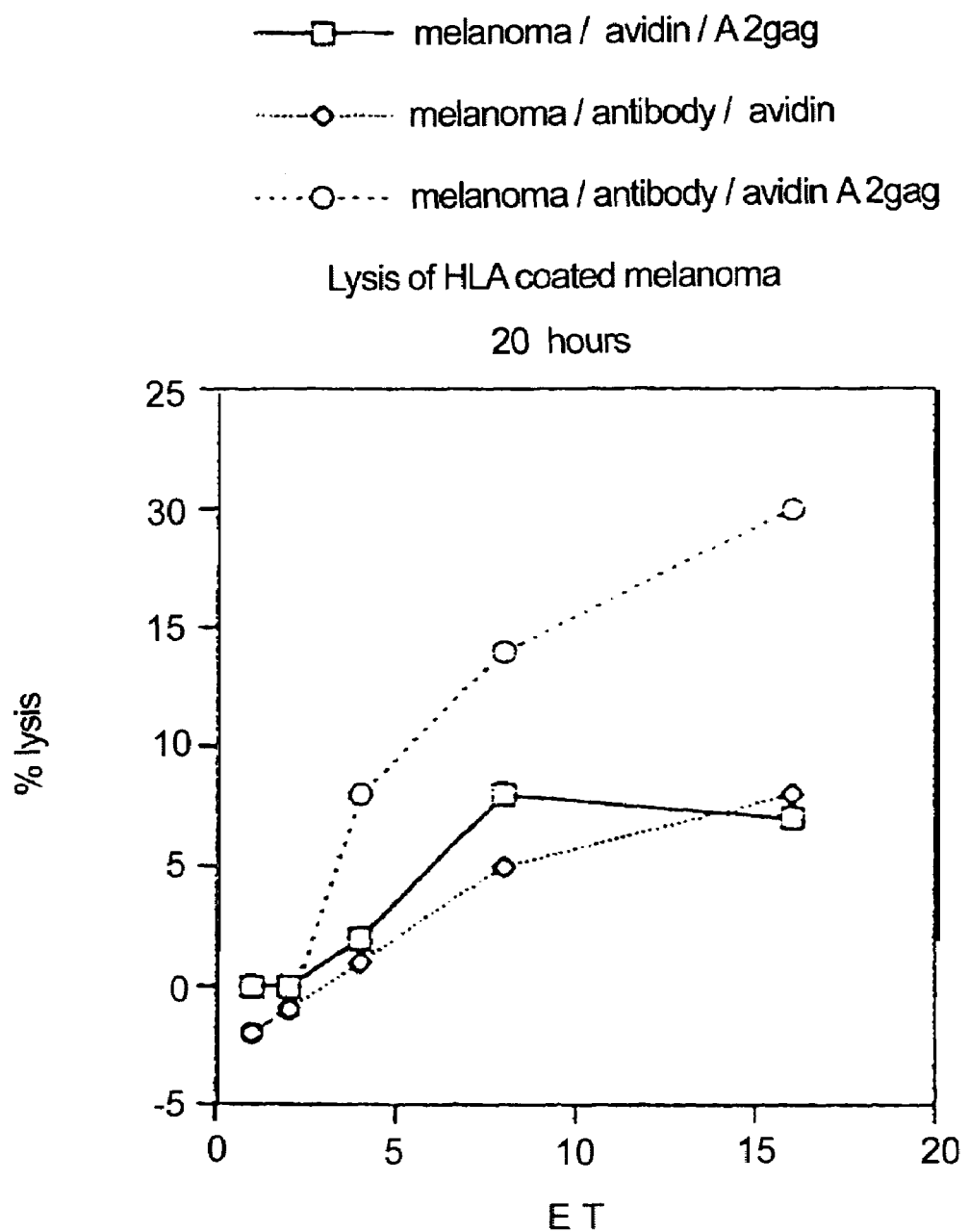
FIG. 3 shows the results of a T cell cytotoxicity chromiun release assay with Mel I cells treated with the delivery system of biotin-conjugated monoclonal antibody 225.28s, avidin, and biotin-conjugated HLA-A2/gag complexes. These cells were incubated with HLA-A2/gag specific cytotoxic T cells with effector/target ratios of 0:1-20:1 for 20 hours.
Figure 4:
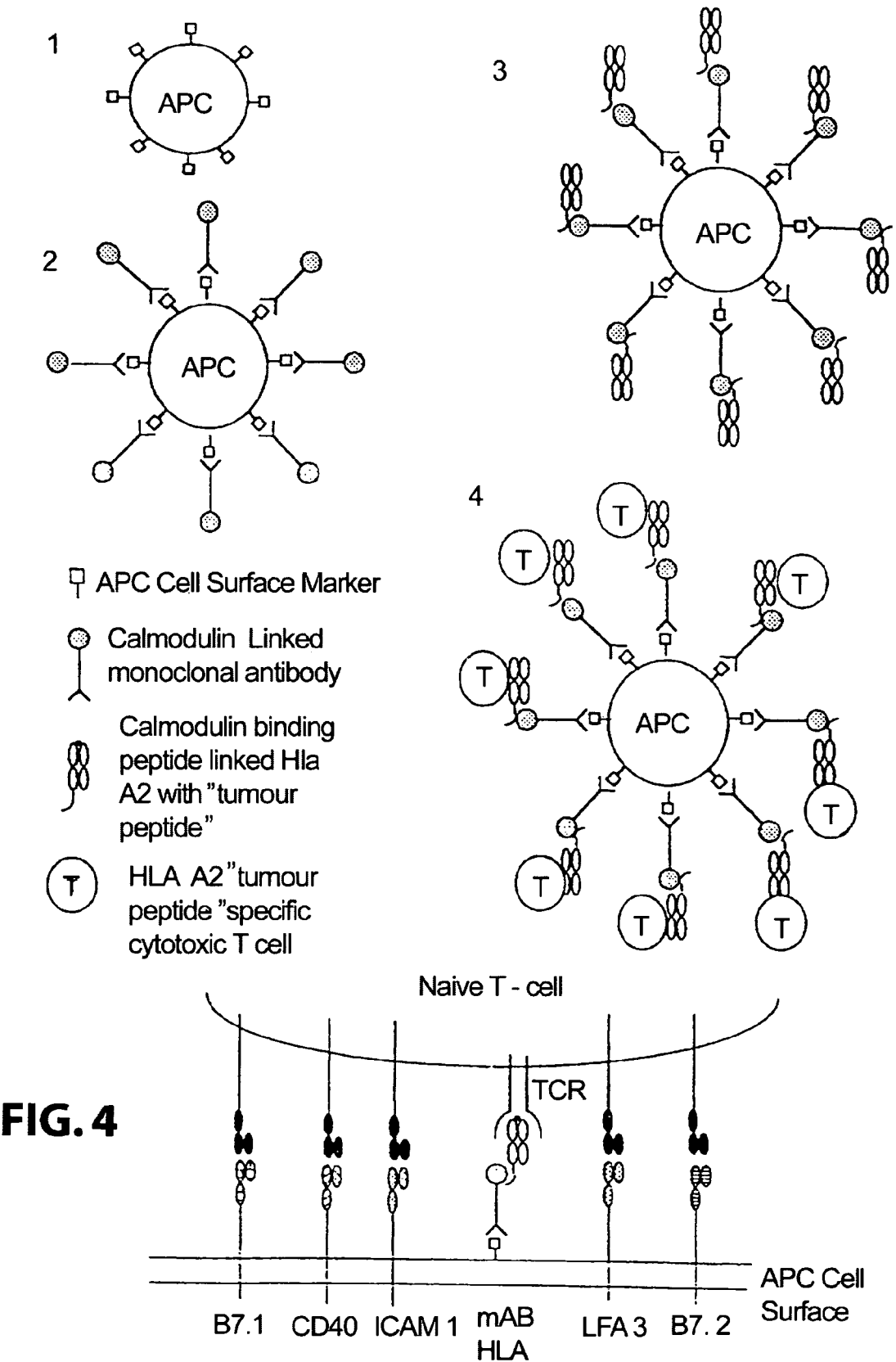
FIG. 4 shows a diagram showing the method/idea for delivering HLA class I/peptide complexes to antigen presenting cells.

The key results of this analysis are illustrated in FIG. 3, which indicates that significant lysis (20%) of Mel 1 cells by HLA-A2/gag specific cytotoxic T cells occurs only when the Mel 1 cells have been treated with all the components of the attaching and delivery means of the present invention (ie biotin-conjugated 225.28s monoclonal antibodies, avidin, and biotin-conjugated HLA-A2/gag). No significant increase in cell lysis over background levels was observed in either of the control runs.

Example 2

The following components were used:

Target cells: The Daudi B cell line (MHC class I-negative), melanoma line SK-mel29 (HLA-A2.1-positive), 0.221/A2 (HLA-A2.1-positive), were maintained in RPMI media with 10% fetal calf serum and antibiotics in a 37° C. incubator with 5% $CO_2$.

Attaching means: Monoclonal antibodies 225.28s (Buraggi 1985 *Cancer Res.* 45 3378-3387) and 2147 that bind to the I-IMW-MAA antigen. Biotin is chemically conjugated onto these antibodies as described in Bayer 1990, *Methods Embryology* 184, 138-160.

Pure hen egg avidin obtained commercially from Societa Prodotti Antibiotici, Milan, Italy.

HLA : Biotinylated complexes of recombinant MHC class I and peptide were produced as described previously. (Altman et al, *Science* 274, 1996, 94-96; Ogg et al, *Science* 279, 1998, 2103). Prokaryotic expression of B2M and MHC class I heavy chain, modified by the C terminal addition of a target sequence for the biotin ligase enzyme BirA, was followed by inclusion body purification. Following refolding of heavy chain and B2M around specific peptide, complexes of 45 kD were isolated by gel filtration, biotinylated overnight using BirA in the presence of ATP, Mg2+ and biotin, and then purified by gel filtration and anion exchange.

T cells: Human cytotoxic T cell clones 010 (specific for HLA-A2/gag 77-85=SLYNTVATL (SEQ ID NO: 2) (Parker et al, J Immunol. 149. 1992, 3580-3587)) and IF9 (specific for HLA-A2/melan-A 26-35=EAAGIGILTV (SEQ ID NO: 3) (Romero et al, J. Immunol. 159, 1997, 2366) were maintained in media supplemented with 5% human serum and IL-2 100 IU/ml.

The stability of the MHC class I/peptide complexes was first established by an ELISA assay. Various MHC class I/peptide complexes, including HLA-A2/Gag3Y, HLA-A2/Gag3F, HLAA2/Lmp2, HLA-B35/Env and HLA-B35/nef, were prepared as outlined above, and were pre-incubated at 10 µg/ml in tissue culture media for 0-20 hours at 37° C. ELISA plates were coated with the mAb W6/32 (5 ug/ml in carbonate buffer pH 9.6 overnight at 4° C.) which recognises conformationally correct MHC class I molecules (Parham, 1979), and then blocked by incubation in 1% bovine serum albumin for 2 hours at 37° C. The MEC class I/peptide complexes were incubated for 30 minutes with the ELISA plates at room temperature, and binding was detected with rabbit anti-human B2 microglobulin followed by alkaline phosphatase conjugated goat anti-rabbit immunoglobulin, and substrate. All incubations were separated by extensive washes in PBS.

Absorbances at 600 nm were measured in a TITERTEK Multiscan ELISA reader. Three assays were performed for each sample, and the mean reading was calculated.

Figure 5:
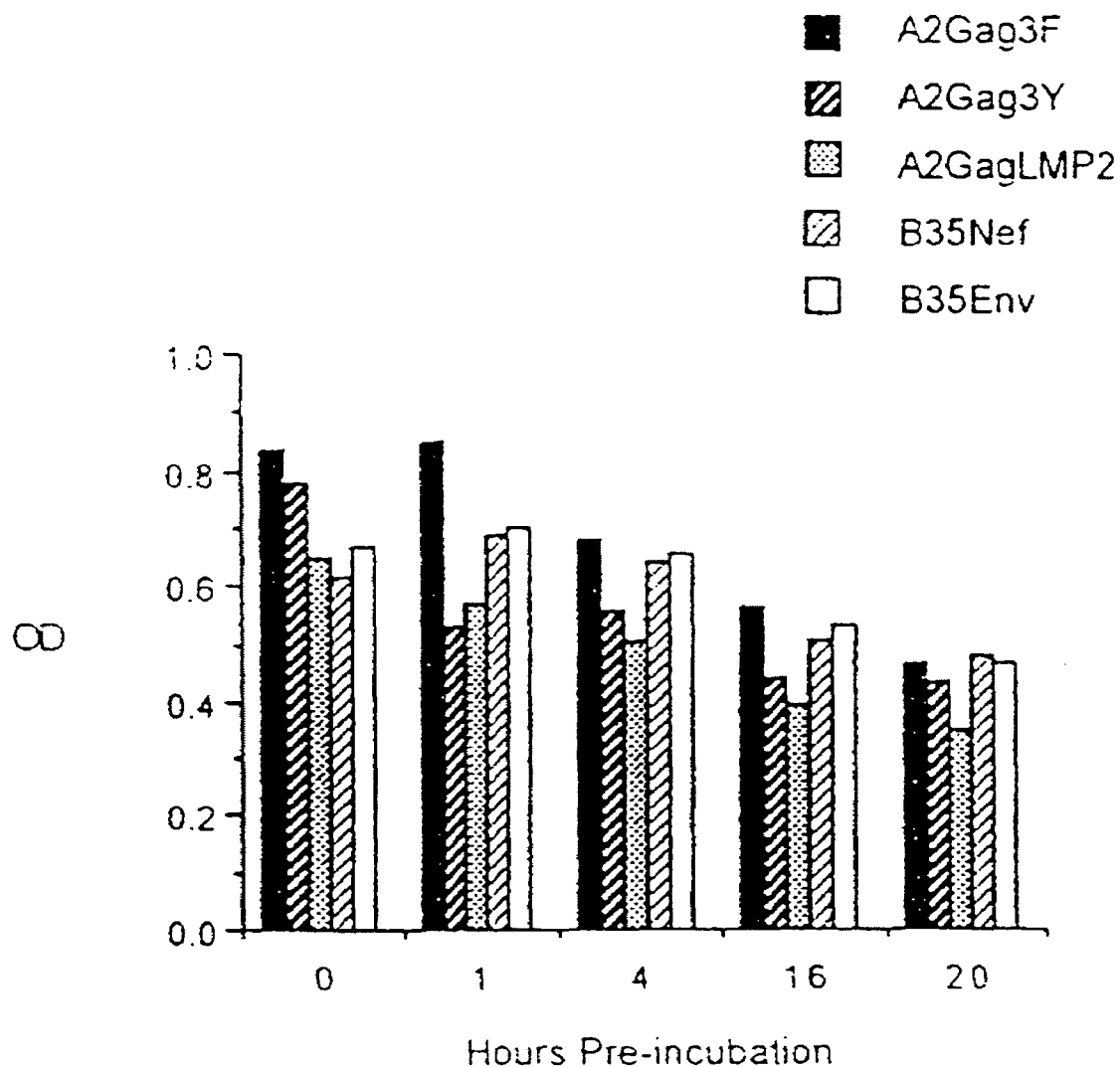
FIG. 5 shows the results of an ELISA assay, described in Example 2 below, for demonstrating the stability of various MHC class I/peptide complexes at 37° C. The results shown are the mean of assays performed on each sample in triplicate.

The results obtained with samples preincubated for 0, 1, 4, 16 and 20 hours are shown in FIG. 5. The results demonstrate that the HLA-A2/gag complexes have appreciable stability in culture media at 37° C., with an estimated half-life in excess of 24 hours.

In storage at 0.5-1 mg/ml at 4° C. HLA-A2/gag complexes appear to be stable for at least 12 months.

To demonstrate the ability of the attaching means to cause display of MHC class I on the surface of Daudi cells, Daudi cells deficient in MHC class I were sequentially incubated at 4° C. with biotinylated anti-CD20 (Ancell, Nottingham, UK; mAb 2H7 (Berenson et al, Blood 67, 1986, 509-515) at 1 µg/ml for 30 minutes); hen egg avidin (S. P. A., Milan, Italy, at 10 µg/ml for 10 minutes); biotinylated HLA-A2/gag (at 10 µg/ml for 10 minutes); and FITC labelled anti-MHC class I (Ancell, Nottingham, UK; mAB 3FI0 (Eisenbarth et al, J. Immunol. 124, 1980,1237-1244) at 10 µg/ml). Parallel controls omitted one or other incubation. Cells were washed 3 times in PBS between stages and then fixed in PBS plus 2% formaldehyde and analysed by flow cytometry.

Figure 6:
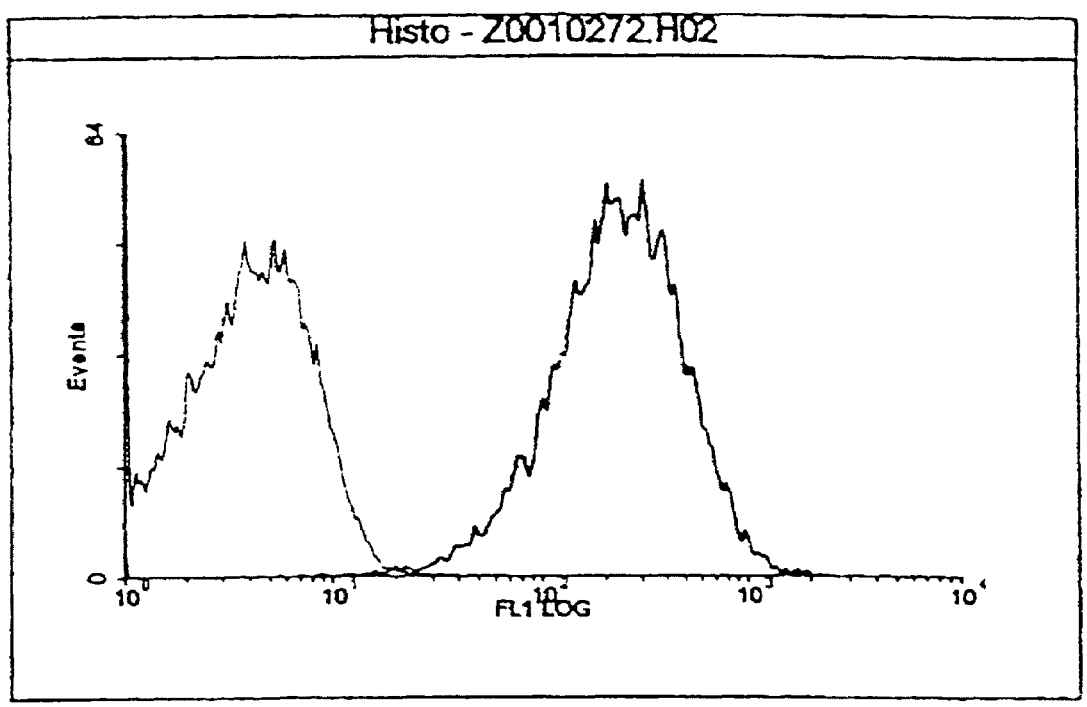
FIG. 6 shows a FACS analysis of HLA-class 1 deficient Daudi cells targeted with HLA-A2 via biotinylated anti-CD20 mAb. Trace 1 (lefthand trace) corresponds to native untargeted Daudi cells. Trace 2 (righthand trace) corresponds to Daudi cells targeted with mAb/avidin/HLA-A2/gag/FITC anti-MHC class I. Mean fluorescence trace 1=0.31, mean fluorescence trace 2=24.3 (arbitrary fluorescence units).

Cells incubated with all three layers of the labelling system had high levels of detectable MHC class I/peptide on their surface compared to untreated Daudi cells (FIG. 6). Cells treated with only any 2 components of the 3-step system gave fluorescence levels comparable to untreated cells.

A chromium release cytotoxicity assay was carried out to establish the ability of specific T cell clones to lyse Daudi or SK-mel-29 cells in accordance with the present invention. Daudi or SK-mel-29 cells were incubated with $^{51}CrO_4$ at 2uCi/uL for 1 hour at 37° C. and then sequentially incubated with: the biotinylated mAbs 2H7 or 225.28s (anti-HMW-MAA) respectively; avidin; and biotinylated HLA-A2/gag complexes as detailed above. Peptide pulsed target cells were incubated with gag 77-85 or melan-A 26-35 peptides at 0.1 uM for 1 hour at 37° C. After washing, labelled target cells were plated into 96-well round bottom plates at 2,500 cells per well, followed by human CTLs at various effector:target ratios. Following incubation at 37° C., 20ul of supernatant was collected and the amount of $^{51}Cr$ released was determined. The percentage of cytotoxicity (lysis) obtained at each effector:target ratio was calculated as: $100\times(E-M)/(T-M)$, where E=Experimental release, M=Release in media and T=Release in 5% Triton X-100 detergent.

Figure 7:
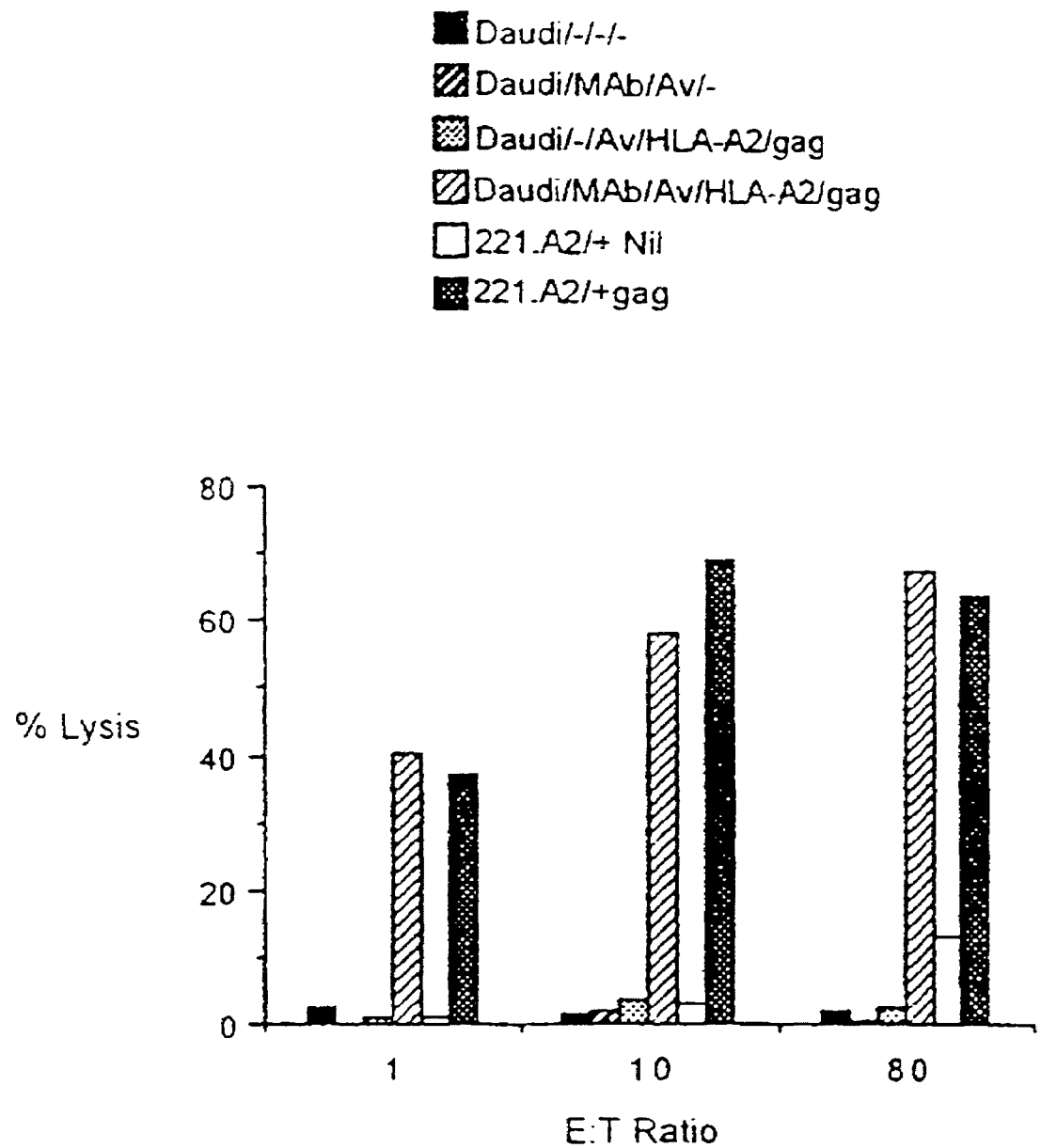
FIG. 7 shows the results of a four hour chromium release assay, described in Example 2 below, in which HLA class I-deficient Daudi cells targeted with various components of the HLA-A2/gag delivery system were incubated with HLA-A2/gag specific cytotoxic T cell clones. A comparison was made with native and peptide-pulsed 221.A2 cells (HLA-A2+ve).

The results shown in FIG. 7 are the mean of experiments performed in duplicate. As shown by these results, the CTL clone (010) efficiently lysed HLA-A2-positive targets (0.221/A2) only when these were pre-incubated with the HLA-A2/gag peptide. MHC class I-negative Daudi cells, when targeted with the HLA-A2/gag complexes of the present invention, were recognised and lysed by this CTL clone to an equivalent degree. Untargeted Daudi cells and cells targeted with only 2 of the 3 components of the targeting system were not recognised (maximal lysis <4°/a at E:T ratios of up to 80:1).

Control CTL, showing a different HLA-A2-restricted specificity (HLA-A2/melan-A), did not lyse Daudi cells targeted with the HLA-A2/gag complexes (FIG. 8), demonstrating the fine specificity of the targeting approach.

Untreated Daudi cells pulsed with gag peptide alone were not lysed by clone 010 (data not shown), in keeping with their lack of endogenous MHC class I.

Figure 8:
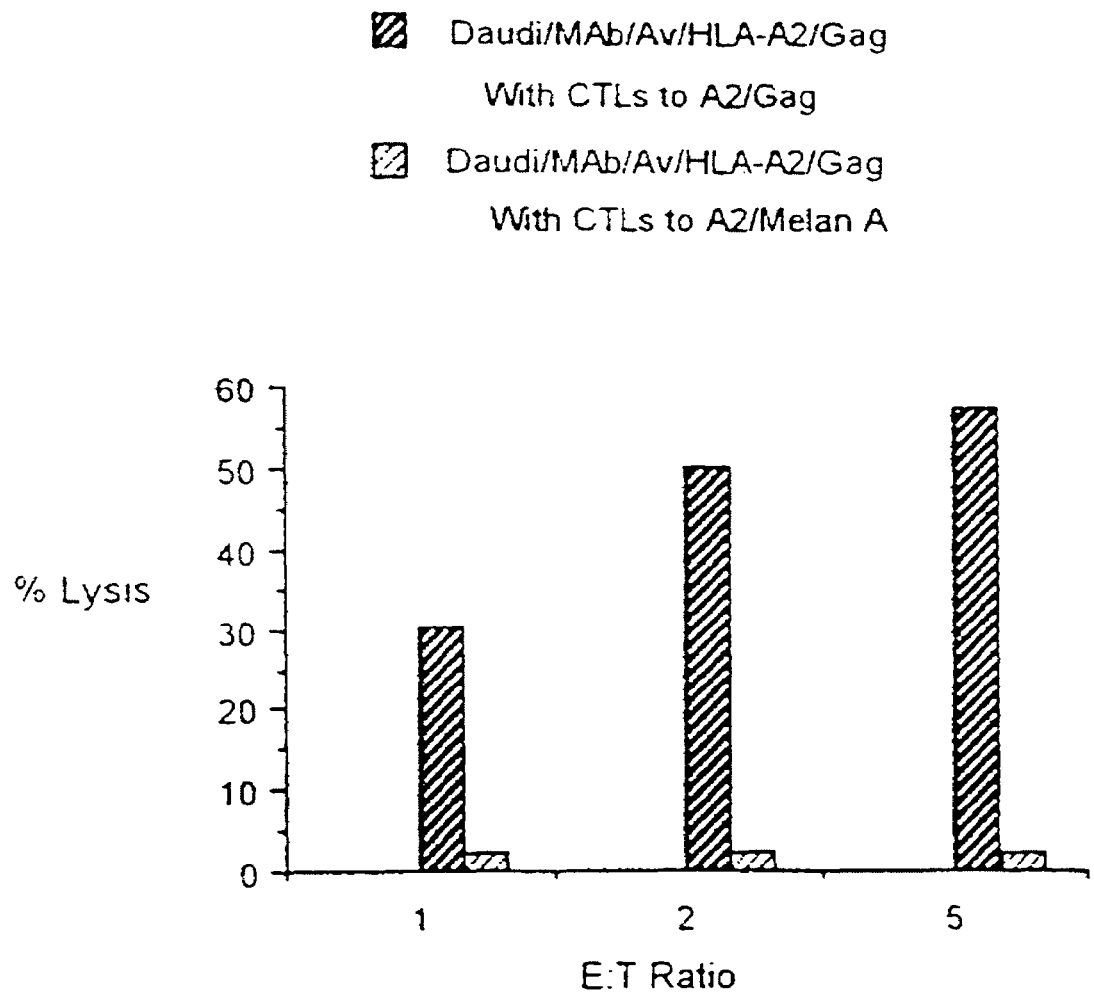
FIG. 8 shows the results of a four hour chromium release assay, described in Example 2 below, in which HLA-A2/gag targeted Daudi cells were incubated with HLA-A2/gag-specific and HLA-A2/Melan A-specific cytotoxic T cell clones.
Figure 9:
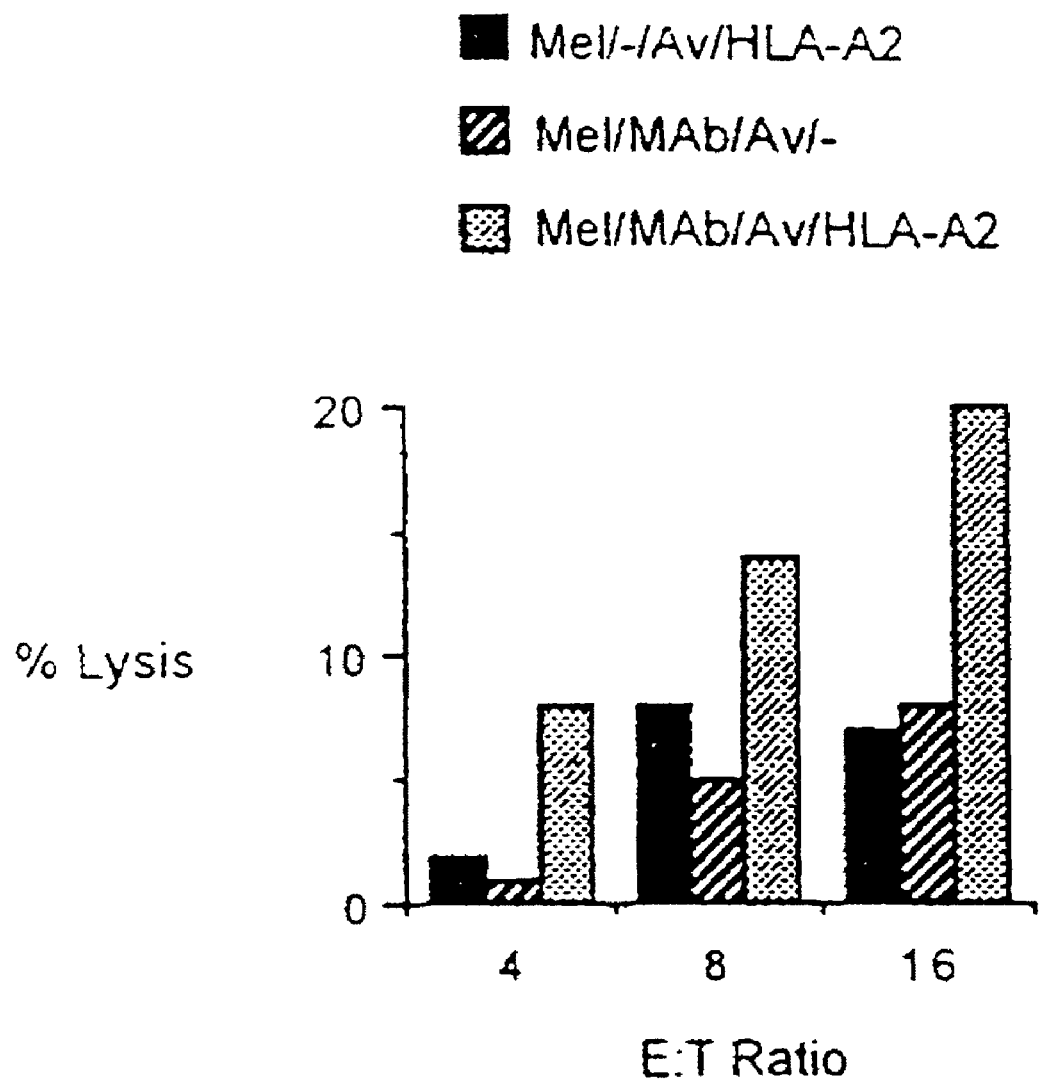
FIG. 9 shows the results of a twenty hour chromium release assay, described in Example 2 below, in which HLA-A2+ve SK29.Mel cells were incubated with HLA-A2/gag specific cytotoxic T cell clones.

The ability of antibody-directed HLA-A2/gag complexes to sensitise the melanoma cell line SK-mel29 to lysis by HLA-A2/gag-specific CTL line is shown in FIG. 8. At all E:T ratios, melanoma cells targeted by complexes linked to surface proteins were lysed substantially more than controls exposed to only two components of the 3-step targeting system. Additionally, MM9 melanoma cells that do not express HLA-A2 were also lysed in a similar manner (data not shown).

Example 3

Immunization/vaccination of a subject using HLA class I/peptide complex(es) to produce and/or amplify immune response(s) directed at particular cell surface molecule(s) may be accomplished according to the present invention. The immune response(s) thus produced are preferably directed at tumour cells which comprise the particular cell surface molecule(s) to which the immune response is produced. The form of this response is influenced by the particular HLA class I/peptide complex(es) used in the immunisation procedure(s).

In this example, use of antibody targeted HLA class I/peptide complexes to amplify a specific CTL response is demonstrated. Thus, example 3 also encompasses a method for delivering HLA class I/peptide complexes to the surface of antigen presenting cells.

In brief, it is demonstrated that biotinylated HLA-A2/peptide complexes immobilised on the surface of an antigen presenting cell via an antibody bridge cause the activation, amplification and expansion of cytotoxic T cells (CD8+ve) reactive with this specific HLA class I/peptide combination.

Materials and Methods

The following components were used:

Daudi cells: a human B cell lymphoma line derived from a patient with Burkitts lymphoma. The cell line was grown in RPMI standard tissue culture media.

Peripheral Blood Cells: peripheral blood mononuclear cells from a donor previously demonstrated to be HLA-A2. These cells were separated from whole blood by differential centrifugation using Ficoll Hypaque and cultured in standard RPMI tissue culture media.

C1R-A2 cells: an HLA class I negative, human B cell line transfected with the gene for HLA-A2. These cells were cultured in RPMI tissue culture media supplemented with G418 400 ug/ml.

Attaching means: B9E9-streptavidin fusion protein, a tetrameric recombinant monoclonal antibody that binds to the B cell antigen CD20 (Schultz et al Cancer Research 2000).

HLA class I/peptide complexes: biotin conjugated recombinant HLA class I allotype HLA-A2 molecules as described by (Altman 1996 (Science 274, 94-96)). These complexes can contain the choice of immunogenic peptides including the influenza matrix MI or EBV BMLF1 peptides. The complexes were obtained from ProImmune Ltd Oxford England.

FACs Analysis:

Methods:

1. Confirmation of ability to target HLA-A2/M1 peptide complexes to surface of B cells.

To confirm the ability of this system to target HLA-A2/M1 peptide complexes to the surface of B cells that can act as APCs, the HLA class I deficient Daudi B cell lymphoma line was used.

Approximately 1 million Daudi cells were first incubated with B9E9-SA diluted to 10 ug/ml in PBS for 1 hr at room temperature.

Following this the cells were washed twice in PBS and then incubated with biotinylated HLA-A2/MI diluted to 1 ng/ml in PBS for 1 hr at room temperature.

The cells were then washed and placed back in a small tissue culture flask containing 5mls of RPMI and incubated at 37° C. in a 5% $CO_2$ atmosphere.

The binding and time course of the residence of recombinant HLA-A2 on the cell surface of the targeted Daudi cells was demonstrated by FACs analysis.

At various time points treated Daudi cells were removed, washed in PBS and incubated for 30 minutes at room temperature with an FITC labelled anti-HLA class I monoclonal (Ancell Ltd) antibody diluted to 10 ug/ml in PBS.

After washing in PBS the cells were analysed on a Becton Dickinson FACscan machine.

2. In vitro immunisation procedure.

30 mls of whole blood was obtained from a healthy volunteer (previously documented by tissue typing to be HLA-A2 +ve). Peripheral blood mononuclear cells were isolated by centrifugation using Ficoll-Hypaque.

Cells were then washed in PBS and then incubated with the B9E9 anti-CD20 streptavidin fusion protein at 10 ug/ml for 1 hr at room temperature.

The cells were then washed in PBS×2, and then incubated with the HLA-A2/peptide combination of choice at a concentration of 0.5 ug/ml for 1 hr at room temperature.

After a further wash in PBS the cells were placed in to 24 well plates at $2 \times 10^6$ cells per well cultured in RPMI+10% FCS (heat inactivated)

On day 1 IL-7 was added to a concentration of 20 ng/ml. On day 4 and every subsequent 3 days IL-2 was added to a concentration of 10 U/ml.

The cells were incubated in a 37° C. incubator with 5% $CO_2$ for the duration of the experiment.

Various controls were also set up using this method including;
PBMCs alone,
PBMCs with the B9E9 antibody,
PBMCs without the B9E9 antibody but with free HLA-A2/peptide complex.

3. Measurement of the induction/amplification of CTL activity.

The effect of the in vitro immunisation procedure on inducing the expansion of specific cytotoxic lymphocytes was assessed by two different modalities. The functional chromium release assay and the more recently described use of fluorogenic HLA-class I tetramers that specifically stain cells with the desired T cell receptor specificity.

a. Fluorogenic HLA class I Tetramer assay.

Samples from these same cells were analysed by tetramer assay. In brief, $3 \times 10^5$ cells were washed in PBS and then re-suspended in 100 uL of PBS. 1 uL of an HLA-A2/peptide tetramer (ProImmune, Oxford England) was added per sample and incubated for 1 hr at room temperature. The cells were then washed in PBS and then incubated at room temperature for 1 hr with a FITC conjugated monoclonal antibody to CD8. (Dako) After further washing in PBS the cells were fixed in a 1% solution of formaldehyde in PBS and analysed on a Becton Dickinson FACscan machine.

Figure 11A:
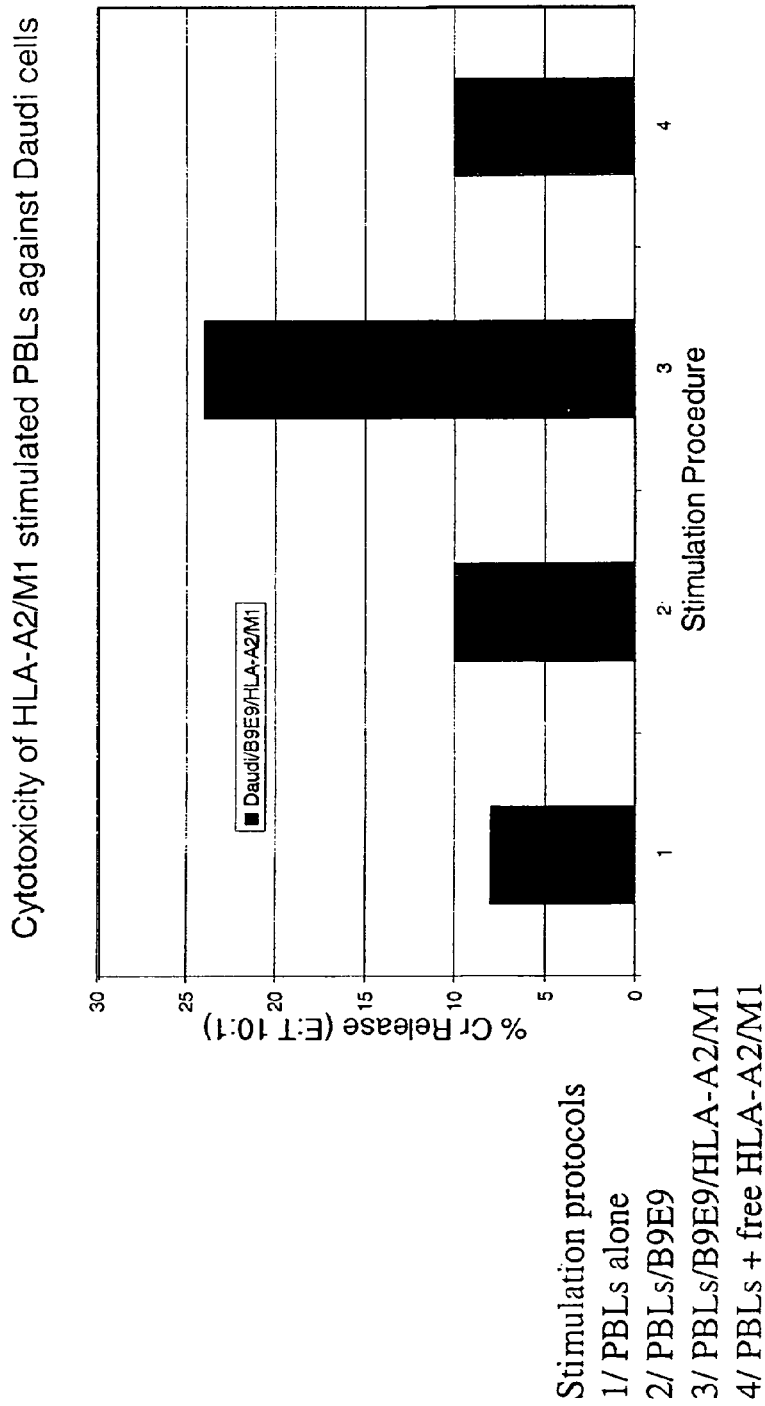
Figure 11E:
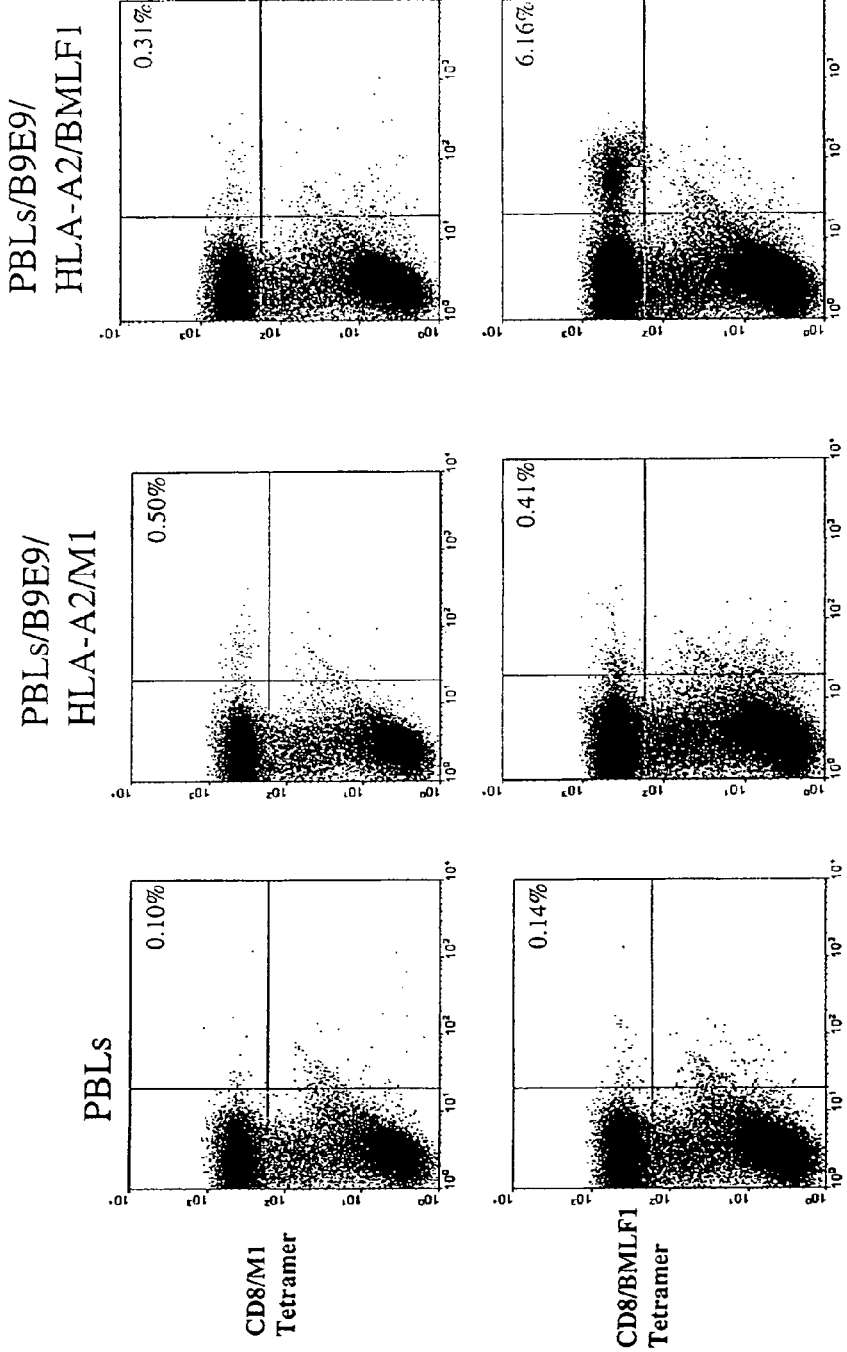

The results are shown in FIG. 11.

b. The $^{51}Cr$ release assay.

This assay follows standard laboratory methods. In brief CIR-A2 cells were labelled with radioactive Chromium (2uCi/ml) by incubation for 1 hr at 37° C. in a solution of $^{51}Cr$ (Amersham). The cells were then washed and then 'pulsed' with a choice of immunogenic peptides at a concentration of 20 uM or no peptide at all for the negative controls. Alternatively Daudi lymphoma cells were used as target cells. Daudi cells were coated with HLA-A2/M1 monomers by first incubating with the B9E9-streptavidin fusion protein (10 ug/ml) for 1 hr at room temperature.

After washing in PBS biotinylated HLA-A2/M1 peptide complexes were added at 1 ng/ml and then incubated for 1 hr at room temperature. Following further washing the cells were used as targets in the CTL assay. These cells were then added to round bottom 96 well plates and various numbers of the cells produced form the 'in vitro immunization' procedure added to give the required 'effector:target' ratios.

After incubation for 4 hours at 37° C., 50 uL of the supernatant was removed and the amount of $^{51}Cr$ released from lysed CIR-A2 or Daudi cells was estimated using a scintillation counter. The results are shown in Tables 8 and 9.

Results and Discussion

1. Demonstration of the binding and prolonged residence of HLA-A2/M1 peptide complexes targeted to CD20+ve cells via the B9E9 fusion protein.

Figure 10:
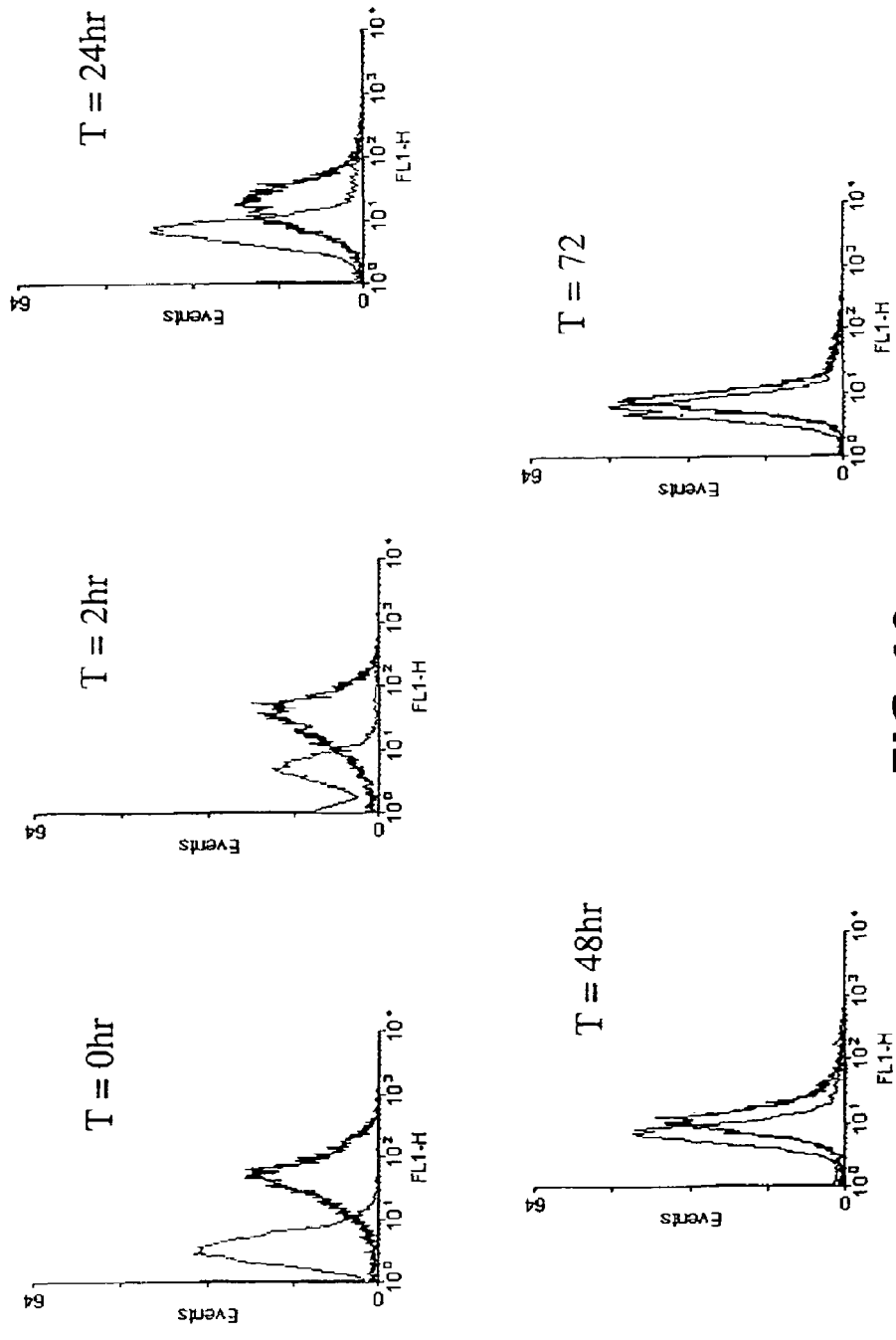
FIG. 10 shows 5 graphs. In more detail.

FIG. 10. Demonstrates the time course for the retention of the HLA-A2/M1 peptide complexes bound via the B9E9/SA fusion protein to Daudi B cells.

The results demonstrate that the binding of the HLA class I/peptide complexes via the B9E9 fusion protein results in their immobilisation on the surface of these cells.

The sequential FACs analyses demonstrate an increase in signal resulting from the bound HLA class I/peptide complexes at time 0 hrs compared to the native cells. This increase over background reduces with time but is still positive after 72 hrs incubation.

2. Demonstration by Tetramer analysis of the expansion of specific CTLs via the binding of HLA-A2/peptide complexes to B cells via CD20

FIG. 11

Introduction

The results of the tetramer analysis are shown in FIG. 11 in both graphical (scatterplot) and numerical form. The value of the X axis varies with the degree of tetramer bind whilst the Y axis varies with the degree of binding of the monoclonal antibody to CD8. Each dot represents an individual cell that has. both an X and Y value.

The cursors are set to produce cut-off values resulting in the formation of 4 quadrants.

The cells in the bottom left quadrant are judged as being negative for CD8 and tetramer binding. The cells in the left upper quadrant are positive for CD8 but negative for tetramer. The cells in the lower right quadrant are positive for tetramer but negative for CD8. The cells in the upper right quadrant are positive both for CD8 and tetramer staining, these cells are the cytotoxic T cells (CTLs) the specificity as defined by the tetramer.

1. Targeting of HLA Complexes

This experiment was performed using the HLA-A2/M1 peptide complex molecule in monomeric form for the in vitro immunization and in tetrameric form for the tetramer analysis.

Results

Sample A1

These are the results from PBMCs incubated without the B9E9 fusion protein or any biotinylated HLA-A2/peptide complexes. Here only 0.089% of all the CD8+ve cytotoxic lymphocytes in the sample have specificity for the HLA-A2/M1 tetramer.

Sample A2

These are the results from PBMCs incubated with the B9E9 fusion protein but without the addition of any biotinylated HLA-A2/M1 complexes. Here 0.0287% of all the CD8 +ve cytotoxic lymphocytes in the sample have specificity for the HLA-A2/M1 tetramer.

Sample A3

These are the results from PBMCs incubated with the B9E9 fusion protein and with the addition of the biotinylated HLA-A2/M1 complexes.

Here 2.19% of all the CD8 +ve cytotoxic lymphocytes in the sample have specificity for the HLA-A2/M1 tetramer.

Sample A4

These are the results from PBMCs incubated without the B9E9 fusion protein but with the addition of the biotinylated HLA-A2/M1 complexes.

Here only 0.197% of all the CD8 +ve cytotoxic lymphocytes in the sample have specificity for the HLA-A2/M1 tetramer.

Further exemplary results may be found in FIG. 11.

These results show that by immobilising HLA class I/peptide complexes on to the surface of an antigen presenting cell (in this example a B lymphocyte, via a streptavin conjugated monoclonal antibody fusion protein with specificity for CD20) that a specific cytotoxic T cell response can be induced as detected by tetramer analysis.

This effect is seen when the complexes are immobilised on the cell surface—PBMCs incubated in an identical way (with IL-7 and Il-2) produce no effect (A1), neither does binding of the B9E9 fusion protein alone (A2) or the addition of free HLA class I peptide complexes (A4).

A further experiment was performed that looked at the specificity of the response to the 'in vitro immunization' procedure using two different HLA class I/peptide combinations and their respective tetramers.

2. In vitro Immunisation Experiment

Similar in vitro immunizations of PBMCs were set up using the following combinations of the B9E9 fusion protein and HLA-A2/M1 and HLA-A2/BMLF1 complexes.

C/PBMCs with B9E9 but without any HLA-A2/peptide complex

F/PBMCs with B9E9 and with the HLA-A2/M1 complex

I/PBMCs with B9E9 and with the HLA-A2/BMLF1 complex

After 10 days incubation tetramer analysis using the antibody to CD8 and the PE conjugated tetramers HLA-A2/M1 and HLA-A2/BMLF1 were performed.

Results

The results of the dual staining were;

|  | CD8 + ve and M1 tetramer + ve | CD8 + ve and BMLF1 tetramer + ve |
| --- | --- | --- |
| Sample C | 0.021% | 0.048% |
| Sample F | 0.254% | 0.074% |
| Sample I | 0.095% | 3.80% |

These results show that the immune response from CTLs as measured by tetramer analysis is specific to the identity of the HLA class I/peptide complex used in the 'in vitro immunization'.

In sample C which had no HLA class/peptide complex added the level of cells staining positive for CD8 and tetramer is low 0.021% for the HLA-A2/MI tetramer and 0.048% for the HLA-A2/BMLF1 tetramer.

Sample F had the HLA-A2/MI peptide complex immobilized on the B cells via B9E9 during the 'in vitro immunization' and here the level of HLA-A2/M1 tetramer positive cells has increased over 10 fold to 0.254% whilst the HLA-A2/BMLF1 tetramer posive cells are similar to sample C at 0.074%.

The ability of the HLA-A2/BMLF1 peptide complex when immobilised on the B cells via the B9E9 fusion protein to specifically expand CTLs reactive with this peptide is shown in the results of Sample I. Here the numbers of CD8 +ve cells reactive with the HLA-A2/M1 tetramer is 0.095%, which is similar to the unstimulated sample C, however now 3.80% of the CD8+ve cells bind the HLA-A2/BMLF1 tetramer, an approximately 80 fold increase in relative number.

Further exemplary results may be found in FIG. 11.

These results support the disclosure of Experiment 1 (targeting experiment; see also predecessor applications) that the immobilised HLA class I/peptide complexes can induce a CTL response and further demonstrate that the response is specific for the HLA-classI/peptide combination. The immobilised HLA-A2/MI complex produces an expansion in CTLs that bind the HLA-A2/MI tetramer, whilst the immobilised HLA-A2/BMLF1 complex produces an expansion in CTLs that bind the HLA-A2/BMLF1 tetramer. There appears to be little non-specific activation of CTLs of the other specificity although some modest expansion may be expected due to the release of cytokines within the cell culture.

3. Demonstration by cytotoxicity $^{51}$Chromium release analysis of the expansion of specific CTLs via the binding of HLA-A2/peptide complexes to B cells via CD20 according to the present invention.

The chromium release assay is another method for reading out T cell activity and can give information on the functional capability of CTLs. Target cells (in this case CIR-A2 or Daudi) cells are labelled with radioactive $^{51}$Chromium and then incubated with varying numbers of 'effector' cells that have been produced by the 'in vitro immunization' procedure with the PBMCs described above.

After incubation (usually 4 hours) a sample of the cell supernatant is taken and assayed for the presence of radioactive $^{51}$Cr which has been released from the target cells as a result of the action of specific cytotoxic lymphocytes in the effector cell population.

The Daudi cells do not express any HLA class I molecules on their cell surface. However if HLA class I /peptide complexes are attached to their surface via a monoclonal antibody they can serve as effective targets for CTLs (Ogg et al 2000).

The CIR-A2 cells serve as targets, they only possess one HLA class I allele the A2 molecule and the exact specifty of this can be altered by placing a peptide of choice within the peptide binding grove by 'peptide pulsing' in vitro. After performing peptide pulsing the target cells have on their cell surface of the HLA-A2 molecules a high proportion containing the peptide of choice and so form a reliable and reproducible target for CTLs of this specificity.

Targeted Lysis Experiment

The results are expressed in terms of the degree of lysis of the target cells during the $^{51}$Cr release assay.

This is calculated according to this equation;

% lysis is calculated as:

$$100\% \times \frac{E-M}{T-M}$$

Where, E=experimental release

M=Media release

T=Maximal release in 5% Triton 100

The ability of the following PBMC preparations to lyse Daudi cells 'coated' with HLA-A2/M1 peptide complexes at an E;T ratio of 10:1 was;

Sample A1

These are the results from PBMCs incubated without the B9E9 fusion protein or any biotinylated HLA-A2/peptide complexes.

Sample A2

These are the results from PBMCs incubated with the B9E9 fusion protein but without the addition of any biotinylated HLA-A2/M1 complexes.

Sample A3

These are the results from PBMCs incubated with the B9E9 fusion protein and with the addition of the biotinylated HLA-A2/M1 complexes.

Sample A4

These are the results from PBMCs incubated without the B9E9 fusion protein but with the addition of the biotinylated HLA-A2/M1 complexes.

Results

TABLE 8

Results of a T cell chromium release assay using HLA class I negative Daudi B cell lymphoma cells as targets. These cells were coated with HLA-A2/M1 peptide complexes attached via the anti-CD20 B9E9-streptavidin fusion protein. The % Lysis of HLA-A2/M1 coated Daudi cells by PBMCs stimulated +/− HLA-A2/M1 complexes

| A1 = | 8% |
|---|---|
| A2 = | 10% |
| A3 = | 24% |
| A4 = | 10% |

These results demonstrate that the treatment of PBMCs with the B9E9-streptavidin fusion protein and biotinylated HLA-A2/M1 peptide complexes in accordance with the present invention results in the amplification of the CTL response to HLA-A2/M1 as measured in this assay. PBMCs treated with both parts of the system (A3) produced 24% lysis whilst the lysis produce by untreated PBMCs (A1), or PBMCs treated with the B9E9 fusion protein alone (A2) or PBMCs treated with free HLA-A2/M1 complexes produced a maximum of only 10% lysis.

Specific Amplification Experiment

To demonstrate that the amplification of CTL response is specific to the identity of the HLA class I/peptide combination, the experiment was repeated with two HLA-A2/peptide specificities.

The results of this show differing patterns of activity for PBMCs treated with B9E9 fusion protein and the two differing HLA-A2/peptide complexes or for those treated without any HLA-A2 peptide complexes.

In this experiment CIR-A2 cells (native or peptide pulsed) were used as target cells.

The figures given are the percent lysis of peptide pulsed target cells. (E:T ratio, 5:1).

TABLE 9

Results of a T cell chromium release assay using CIR-A2 target cells that had been 'pulsed' with either nothing or the flu M1 or EBV BMLF1 peptides as indicated. The effector cells were cultured from peripheral blood cells, of an HLA-A2 + ve healthy donor, incubated with the anti-CD20 B9E9-streptavidin fusion protein alone and HLA-A2/M1 or HLA-A2/BMLF1 complexes.
Immunization protocol:

| Targets | B9E9-SA + Nil (sample C) | B9E9-SA + HLA-A2/M1 (sample F) | B9E9-SA + HLA-A2/BMLF1 (sample I) |
|---|---|---|---|
| CIR-A2 + Nil | 5.3% | 11.9% | 10.7% |
| CIR-A2 + MI | 4.8% | 13.6% | 10.2% |
| CIR-A2 + BMLF1 | 7.3% | 16.4% | 23.7% |

In this experiment it is again demonstrated that PBMCs that are just targeted with the B9E9 molecule do not produce any significant lysis of target cells either native CIR-A2 or peptide pulsed with the M1 or BMLF1 peptides.

PBMCs targeted with B9E9 and HLA-A2/M1 complexes produced a weak response in this particular experiment without any clear pattern of enhanced lysis.

PBMCs targeted with B9E9 and HLA-A2/BMLF1 complexes produced CLS that had enhanced activity against CIR-A2 cells pulsed with BMLF1 (23.7%) but no increased lysis against either native CIR-A2 cells (10.7%) or CIR-A2 cells pulsed with M1 peptide (10.2%).

These results further illustrate the production of a CTL response that is predominantly against the HLA class I/peptide complex which is immobilised on the surface of the antigen presenting cell according to the present invention (in this Example, B cells via CD20 using B9E9 fusion protein).

Summary

The data in this document demonstrate that HLA-class/peptide complexes when immobilised on the surface of an antigen presenting cell via an antibody bridge result in the amplification of the immune response to that specific HLA-class/peptide complex.

The ability to specifically produce amplification of cytotoxic T cell numbers and/or activity to a particular HLA class 1/peptide combination is an advantageous feature of the present invention.

The system(s) described herein offer considerable possibilities as methods for producing/enhancing/augmenting immune response(s) in malignant illnesses such as cancer/leukaemia/lymphoma. Furthermore, these systems may find application in infectious diseases including HIV and leprosy.

Example 4

In vivo Cancer Cell Therapy

In certain embodiments, the invention relates to using anti-viral CTLs in therapeutic approaches to combat tumour/cancer cells.

In this example, it is demonstrated that anti-viral Cytotoxic T cells inhibit the growth of cancer cells bearing antibody targeted MHC class I/peptide complexes in SCID mice.

In the present invention, cytotoxic T cells (CTLs) of non-tumour specificity are redirected against cancer cells. It is demonstrated herein that cancer cells targeted with recombinant HLA-class I/peptide complexes via an antibody delivery system can be effectively lysed by anti-viral CTLs in vitro. Furthermore, this example demonstrates effects in vivo in a mammalian system.

This system uses the recombinant anti-CD20 B9E9 sfvSCSA fusion protein to target HLA-A2/M1 complexes to CD20+ve Daudi lymphoma cells. Binding of the B9E9 sfvScSA fusion protein to Daudi cells in culture had no apparent effect on growth kinetics. Using an HLA-A2/M1 specific human T cell clone, in vitro killing of targeted Daudi cells was achieved with HLA class I concentrations as low as 5 pg/ml. A tumour protection assay using human CTL to the HLA-A2/M1 complex was performed in SCID mice. Applicant demonstrates that only 1 of 4 mice receiving Daudi cells targeted with both the B9E9 sfvSCSA fusion protein and the HLA-A2/M1 complex developed tumours, whilst in the control mice with receiving CTL but native Daudi cells 4 of 4 developed tumours, as did 4 of 4 receiving targeted Daudi cells but no CTLs.

This demonstration of the in vivo activity for the combination of targeted HLA class I/peptide complexes and anti-viral T cells, demonstrates the effectiveness of the antibody HLA class I targeting system. Clearly, this system may be advantageously combined with autologous CTLs produced by vaccination or ex vivo expansion.

This example also embraces aspects of the delivery (targeting) system. This example further illustrates a useful model system.

The B cell surface antigen CD20 serves as a good target for this system as it is expressed on many B cell malignancies, remains on the cell surface for days and is not internalised on antibody binding. Monoclonal antibodies to CD20 are available and are well characterised (Hainsworth 2000). Recombinant antibody fragments have also been developed. The tetravalent B9E9 sfvScSA fusion protein (see Schultz et al 2000) is useful as a targeting system.

To demonstrate the abilities of human CTLs of anti-viral specificity to interact with tumour cells targeted with HLA-A2/peptide complexes in a physiological setting, a model was developed as explained below.

Severe combined immunodeficient (SCID) mice are capable of supporting functional human CTLs for periods, possibly requiring a degree of cytokine support (de Kroon J. et al 1997, Buchsbaum et al 1996)

The human B cell lymphoma Daudi cell line can grow as a xenograft in SCID mice without requiring further routine immunosuppression and has been used in a variety of therapeutic systems (see Gidlof et al 1997, Ghetie et al 1996).

This example demonstrates the in vivo interaction of human anti-viral CTLs and HLA targeted Daudi cells in a tumour protection experiment.

Cell lines:

Clone 25—A human cytotoxic T cell clone with specificity for HLA-A2/M1 was maintained in RPMI with 10% AB serum and antibiotics.

Daudi B cell lymphoma—A CD 20 +ve human B cell lymphoma cell line that is deficient for the expression of HLA class I. Daudi cells were maintained in RPMI media supplemented with 10% FCS and antibiotics in a 37° C. incubator with 5% $CO_2$.

Antibodies:

Anti MHC class I (W6/32) Fitc conjugated (Sigma)

B9E9 sfvscSA. A recombinant tetravalent scFV/streptavidin fusion protein with specificity for CD20 (Schultz et al, 2000)

Mice:

Male SCID mice aged 6-8 weeks were maintained in sterile conditions in a suitable animal facility.

Facs analysis:

Becton Dickinson FACscan machine with relevant software.

Methods

Action of B9E9 scFvSA on Daudi cell growth

Daudi cells were washed in PBS and then incubated with dilutions of the B9E9 scFvSA in PBS for 1 hour at room temperature. After two washes the cells were resuspended in 5 mls of tissue culture media and incubated at 37° C. in a 5% CO2 atmosphere. The proliferation of the antibody treated cells and controls was assessed by sequential counts of the viable cells using Trypan blue exclusion and a haemocytometer.

Effect of HLA Dilutions on in vitro CTL Mediated Lysis

Standard Chromium release assays were performed using the Daudi B cell line as the target cell. Briefly, cells were labelled with 100 uCi of $^{51}Cr$ (Amersham Pharmacia) for 1 hr at 37° C. After washing in PBS, cells were incubated with B9E9 at 10 ug/ml for 1 hr at room temperature. After two further washes cells were incubated with dilutions of HLA-A2/M1 complexes in PBS for 1 hour at 4° C. After 2 further washes the cells were plated out at 3000 cells per well in U-bottomed 96 well plates. Tissue culture media, dilutions of CTLs or 5% Triton X-100 were added to a final volume of 200 uL. Plates were incubated for 4 hours at 37° C. in a 5% CO2 atmosphere and then 50 uL of supernatant collected and added to 150 uL of scintillant in a standard scintillation plate and counted.

The specific lysis was calculated as;

$$\% \text{ lysis} = \frac{\text{experimental cpm} - \text{spontaneous cpm}}{\text{maximum cpm} - \text{spontaneous cpm}} \times 100$$

The spontaneous release was measured from the cells incubated in media alone, the maximum release was measured from the cells incubated in Triton.

FACS analysis was performed on the cells targeted with B9E9 sfvScSA fusion protein and HLA-A2/M1 prepared as above. Samples of cells were washed in PBS and then incubated with FITC labelled-anti-MHC class I (Ancell, Nottingham UK) and analysed by flow cytometry on a Becton Dickinson FACscan.

In vivo Tumour Protection Assay

Healthy male SCID mice aged 6-8 weeks were used for the tumour protection assay. Four mice were used in each of the 3 groups A, B and C, treated as follows;

Group A

Mice in Group A were injected IP with $3 \times 10^6$ clone 25 cells in 0.2 ml of sterile PBS on Day 1. On Day 2 $1 \times 10^6$ Daudi cells targeted sequentially, ex vivo, with B9E9 sfvFSA (10 ug/ml) and HLA-A2/M1 (0.5 ug/ml) were injected IP in 0.2ml of sterile PBS.

Group B

Mice in group B were injected IP with $3 \times 10^6$ clone 25 cells in 0.2 ml of sterile PBS on Day 1. On Day 2 $1 \times 10^6$ native Daudi cells were injected IP in 0.2 ml of sterile PBS.

Group C

Mice in group C were injected with 0.2 ml of sterile PBS on Day 1. On Day 2 $1 \times 10^6$ Daudi cells targeted sequentially, ex vivo, with B9E9 sfvFSA (10 ug/ml) and HLA-A2/M1 (0.5 ug/ml) were injected IP in 0.2 ml of sterile PBS.

The mice in all 3 groups received IP injections with human IL-2 (Chiron) 2,500 U in 0.1 ml PBS daily on days 1-3.

Effects of B9E9 SFVSCSA Binding on Daudi Cell Kinetics in vitro

To investigate the possibility of any apparent effect on cell kinetics from the binding of the B9E9 sfvSA fusion protein to the Daudi lymphoma cells a simple in vitro study was performed. The results from this shown in Table 10 show the growth over 4 days of the cells treated with dilutions of B9E9 sfvScSA and the untreated control cells. The rates of proliferation for the native and antibody bound cells appear comparable with no significant effect on the growth of the Daudi lymphoma cells in culture resulting from B9E9 sfvScSA binding.

TABLE 10

Effects of B9E9 sfvSA binding to Daudi cell growth kinetics in vitro. (Results expressed as cells × $10^4$/ml)

|  | Day 0 | Day 1 | Day 2 | Day 3 | Day 4 |
|---|---|---|---|---|---|
| Expt 1 (B9E9) 19.3.01 |  |  |  |  |  |
| Daudi + nil | 20 | 27 | 33 | 51 | — |
| Daudi + 0.1 ug/ml | 20 | 34 | 33 | 54 | — |
| Daudi + 1 ug/ml | 20 | 23 | 33 | 76 | — |
| Daudi + 10 ug/ml | 20 | 26 | 27 | 76 | — |
| Expt 2 (B9E9) 9.4.01 |  |  |  |  |  |
| Daudi + Nil | 20 | 22 | 29 | 36 | 71 |
| Daudi + 10 ug/ml | 20 | 11 | 17 | 32 | 70 |

Dose Response of HLA Binding Concentration (Measured by FACS Signal and Cr Release Assay)

To investigate the effects of varying of the concentration of biotinylated HLA class I molecules delivered to the target cells a dose response was obtained using FACs analysis and Cr release assays as shown in Table 11.

The results indicate that a positive signal could be obtained by FACs with concentrations of biotinylated HLA down to approximately 1-5 ng/ml. The functional chromium release assay show that effective lysis of target cells can occur when exposed to concentrations of biotinylated HLA class as low as 5 pg/ml, which is producing levels of HLA binding that are significantly below the level of FACs detection.

TABLE 11

HLA-A2/M1 complex concentration/ml

|  | FACs (Gm) | $^{51}$Cr |
|---|---|---|
| Nil | 5.8 | 2% |
| 10 μg | 18.98 | n/d |
| 1 μg | 22.54 | n/d |
| 0.1 μg | 18.41 | n/d |
| 10 ng | 8.47 | 42% |
| 5 ng | 7.40 | n/d |
| 1 ng | 5.71 | 51% |
| 0.5 ng | 5.8 | 50% |
| 0.1 ng | 4.6 | 42% |
| 50 pg | — | 34% |
| 10 pg | — | 22% |
| 5 pg | — | 18% |
| 1 pg | — | 1% |

(4 hour chromium release assay E:T ratio 5:1)

In Vivo Tumour Protection Assay

The ability of anti-viral CTLs to interact with cancer cells targeted with the HLA-class I peptide complexes was assayed in a tumour protection assay in SCID mice. After inoculation of the tumour cells the animals were monitored and sacrificed at day 60 when signs of disease became apparent. After sacrifice the mice were dissected and the tumour tissue weighed.

The results of the 3 groups were:
Group A (Day 1 Clone 25, Day 2 Daudi+B9E9+HLA-A2/M1)
 1) Tumour mass 2.4 g
 2) No tumour
 3) No tumour
 4) No tumour
Group B (Day 1 Clone 25, Day 2 Daudi-native)
 1) Tumour mass 5.64 g
 2) Tumour mass 0.66 g
 3) Tumour mass 1.54 g
 4) Tumour mass 2.36 g
Group C (Day 1 PBS, Day 2 Daudi+B9E9+HLA-A2/M1)
 1) Tumour mass 3.78 g
 2) Tumour mass 1.50 g
 3) Tumour mass 3.06 g
 4) Tumour mass 3.47 g Thus, use of the cellular immune system to selectively attack cancer cells according to the present invention has been demonstrated.

There are an increasing number of tumour associated peptides described that may serve to immunologically distinguish cancer from normal cells, and may therefore be useful in targetting aspects of the present invention. Particularly suitable are tumour specific or tumour associated cell surface antigens that can be bound by monoclonal antibodies. A number of these antibodies are now available, and could be adapted to deliver complexes of the present invention to the surface of tumour cells.

The production of large numbers of CTLs reactive with viral epitopes useful in the present invention is relatively easy in vivo as a result of infection by the relevant virus(es) and/or vaccination with said viral epitope(s). These CTLs may even be prepared/supplied ex vivo by specific antigenic stimulation.

The use of antibody targeted HLA class I/peptide complexes to redirect the lytic action of CTLs having anti-viral specificity against tumour cells according to the present invention is demonstrated. Antibody targeted HLA class I tetramers may be used, and a range of tumour cells targeted may be effectively killed by anti-viral CTLs. These aspects of the present invention are further illustrated by the in vivo data presented herein.

The applicant has advantageously reduced the number of targeting steps to two in this example by the use of the B9E9-sfvScSA fusion protein.

To investigate if binding of B9E9 to the Daudi cells used in the in vivo examples had any effect itself on said cells, the applicant examined the effects of binding B9E9 on cell growth. The results shown in Table 10 demonstrate that there was no significant effect on cell growth. Thus, without wishing to be bound by theory, the effects observed clearly flow from the methods of the present invention, and not from a mere effect of antibody binding.

The results shown in Table 11 demonstrate that significant lysis of tumour cells occurs in vitro even at very low concentrations of the biotinylated HLA class I/M1 complex. Only at levels of 50 pg/ml or below does the degree of lysis begin to reduce slightly and activity is maintained down to 5 pg/ml.

The very high affinity of biotin-streptavidin interaction ($10^{-15}$M) means that binding takes place efficiently even at these low concentrations. In a clinical scenario, with possible difficulties of targeting access, a possible degree of antigen shedding and possibly a relatively short half-life of polypeptide chain types of recombinant HLA class I molecules, this advantageous feature of the present invention (ie. the ability to produce functionally effective targeting at low HLA concentrations and/or to produce effective CTL mediated lysis with only relatively small numbers of molecules immobilised on each target cell) may be very valuable.

Function of the system in vivo is demonstrated. Of the animals pre-treated with the anti- HLA-A2/M1 CTL clone 25 and then injected with targeted Daudi cells, only 1 of the 4 developed a tumour. In contrast, the control groups (i.e. either mice pre-treated with clone 25 but receiving-native Daudi cells, or mice with no CTL pre-treatment receiving targeted Daudi cells), all 4 of each group developed tumours.

Thus, it is demonstrated that anti-viral CTLs can effectively interact in vivo with these cells and are effectively targeted with antibody targeted HLA class I/peptide complexes according to the present invention.

The low toxicity of the targeting antibody and of the recombinant HLA class I peptide complexes demonstrates that sufficient molecules may be delivered to target cells, facilitating effective CTL activity according to the present invention.

HLA stability may advantageously be improved by the production of single chain recombinant versions.

Production of CTLs by vaccination, or the administration of CTLs expanded ex vivo such as described for the treatment of EBV associated lymphoma (Savoldo et al 2000) may be advantageously employed in the present invention.

TABLE 12

| HLA cone | Clone 25 E:T 8:1 | Clone 25 E:T 10:1 | Clone 12 E:T 5:1 |
|---|---|---|---|
| 10 ug/ml | 91% | | |
| 5 ug/ml | 38% | | |
| 1 ug/ml | 69% | | |
| 100 ng/ml | 69% | | |
| 10 ng/ml | 46% | 97% | 42% |
| 1 ng/ml | 75% | 85% | 51% |
| 0.5 ng/ml | — | 79% | 50% |
| 0.1 ng/ml | 49% | 87% | 42% |
| 0.05 ng/ml | — | — | 34% |
| 0.01 ng/ml | 27% | 44% | 22% |
| 0.005 ng/ml | — | 26% | 18% |
| 0.001 ng/ml | 13% | 12.8% | 1.4% |

Example 5

Induction of Viral and Tumour Specific CTL Responses using Antibody Targeted HLA Class I Peptide Complexes Introduction A central aim of cancer immunotherapy is the induction of effective cytotoxic T cell activity that recognises HLA class I/peptide complexes that are either. specific to or over-represented on tumour cells (Rosenberg, 1996). There is increasing evidence that low levels of CTLs specific for 'tumour' peptides are present in a number of malignancies (Pittet et al, 1999), however the magnitude of these pre-existing responses frequently appears to be insufficient for effective in vivo activity.

The interaction between the HLA class I/peptide complex and the T cells antigen receptor is the final pathway in the expansion of CD8+ve CTLs. A range of approaches aim to reach this interaction, starting with either defined tumour associated peptide or more complex cellular based preparations. These methods include vaccination with peptides (Rosenberg et al, 1998), naked DNA (Mincheff et al, 2000) or irradiated tumour cells (Chan and Morton, 1998), these systems rely on processing and presentation by native antigen presenting cells (APCs). Alternatively ex vivo expanded dendritic cells can be used either with peptide pulsing (Hsu et al, 1996, Brossart et al, 2000), loading with tumour lysate (Nestle et al, 1999) or transfected with genes encoding tumour proteins (Wang B et al, 2000). Recombinant HLA-class I/peptide complexes either immobilised on beads (Lone et al, 1998, Tham et al, 2001), incorporated into antibody based fusion proteins (Cullen et al, 1999), or as recombinant MHC tetramers (Wang T et al, 2000) have also produced effective CTL responses both in vitro and in pre-clinical models.

Dendritic cells are the most effective APCs but are present in low numbers in vivo and are difficult to culture, in contrast B cells are present in large numbers, are simple to manipulate in vitro and have been demonstrated to act effectively as APCs inducing specific CTL responses in vivo (Gajewski et al, 2001).

Figure 12:
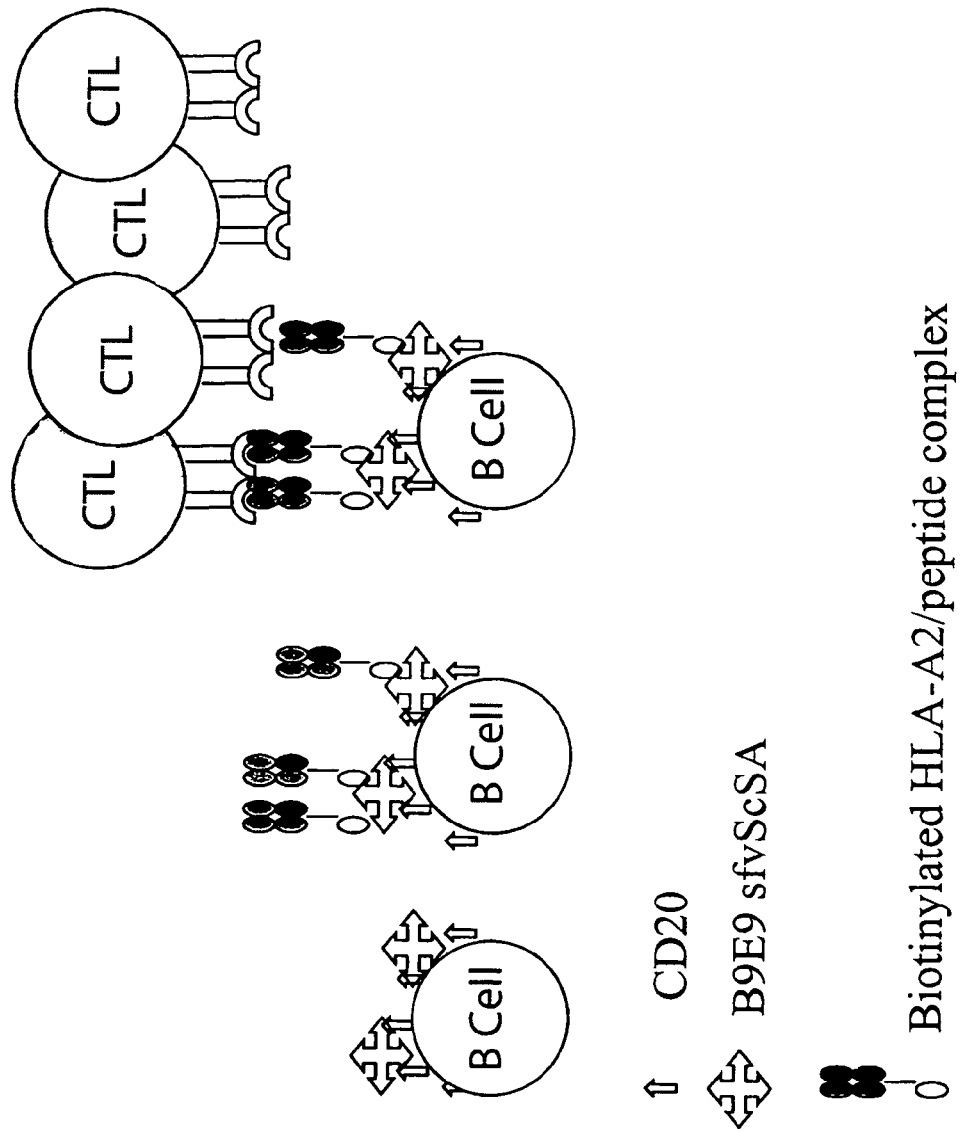
FIG. 12 shows schematic representation of the two-step targeting system delivering HLA-class I peptide complexes to the surface of B cells. Step 1 is the delivery of the antiCD20 B9E9 sfvScSA fusion protein. Step 2 the delivery of recombinant biotinylated HLA class I peptide. These steps are followed by the selective proliferation of peptide specific CTLs.

In a previous example we demonstrate that HLA class I/viral peptide complexes targeted to B cells via an antibody delivery system can serve as effective targets for the lytic action of anti-viral CTLs (see also Ogg et al, 2000, Savage et al, 2002). In this example we have used a similar system to investigate if the 2-step antibody delivery system (see FIG. 12) is able to produce the specific expansion of CTLs of chosen specificities from unselected populations of PBMCs.

Materials and Methods

Antibodies:

The B9E9 scFvSA fusion protein contains the single-chain variable region of the murine IgG2a anti-CD20 murine antibody B9E9 fused to the genomic streptavidin of *Streptomyces avidinii*. The protein is secreted into the periplasm of genetically engineered *E. coli* as monomeric subunits (43,400 Daltons) that spontaneously fold into soluble tetramers with a molecular weight of 173, 600 Daltons. The four antigen-binding and biotin-binding sites of the fusion protein retain the functional capabilities of the parent molecules (Schultz et al, 2000). The FITC conjugated monoclonal antibodies used in flow cytometry were anti-MHC class I (W6/32) (Cymbus Biotechnology, Harrow, UK), anti-CD19, anti-CD80 and anti-CD86 (Dako, Ely, UK).

Cells:

The CIR-A2 (Storkus et al, 1989) and Daudi (Klein et al, 1968) cell lines were grown in RPMI+10% FCS supplemented with Penicillin and Streptomycin in a 37° C. incubator with 5% $CO_2$. PBMCs were isolated from healthy volunteers and melanoma patients previously documented to be HLA-A2+ve. Approximately 30 mls of venous blood was obtained by venepuncture and unfractionated PBMCs were obtained by differential centrifugation using Histopaque (Sigma, Poole, UK).

HLA-A2/peptide complex monomers and tetramers:

Recombinant HLA-A2 class I molecules were obtained from ProImmune Ltd, (Oxford Science Park, Oxford UK). In brief, recombinant HLA -A2 heavy chain and beta-2 microglobulin were produced in *E. Coli*. The functional HLA class I/peptide complex were produced by refolding around the peptide of choice and then biotinylation via the Bir A site on the HLA heavy chain. (Garboczi et al, 1992, Altman et al, 1996)

The peptides used in these experiments were Influenza virus M1 peptide GILGFVFTL (SEQ ID NO: 4) (Gotch et al, 1987), Epstein-Barr virus (EBV) BMLF1 peptide GLCTL-VAML (SEQ ID NO: 5) (Steven et al, 1997) and the modified melanoma associated Melan A peptide ELAGIGILTV (SEQ ID NO: 6) (Valmori et al 1998). The PE conjugated fluorescent HLA-A2/peptide tetramers of the same specificities used for flow cytometric analysis were also obtained from ProImmune.

Methods

Targeting of B9E9 scFvSA and HLA-A2/Peptide Complexes to HLA Class I −ve B Cells.

HLA class I−ve Daudi cells were used to investigate the binding of the HLA-A2/class I peptide complexes via the B9E9 scFvSA. Cells were washed in PBS and incubated with B9E9 scFvSA diluted in PBS at 10 ug/ml for 1 hour at RT. After washing the cells were incubated with either biotinylated HLA-A2/M1 peptide complexes at 0.5 ug/ml or PBS alone for 30 minutes at RT. After further washing the two groups of cells were resuspended in RPMI+10% FCS and grown at 37° C. in a 5% $CO_2$ atmosphere. At various time points parallel samples of cells were removed, washed and incubated for 30 minutes at RT with FITC conjugated W6/32, after washing the cells were analysed by flow cytometry.

The Effects of B9E9 scFvSA Binding on the Expression of Co-stimulatory Molecules in PBMC B Cells.

PBMCs prepared by differential centrifugation were incubated with B9E9 scFvSA (10 ug/ml), IL-7 (10 ng/ml), B9E9 scFvSA and IL-7 or PBS alone for 1 hour at RT. After washing the cells were placed into tissue culture media and returned to culture at 37° C. Samples were removed and double stained with PE conjugated anti-CD19 and either FITC conjugated anti-CD80 or anti-CD86 and analysed on a Becton Dickinson FACScan using FACScomp software.

In vitro Immunisation Protocol

PBMCs were incubated with the B9E9 scFvSA (10 ug/ml) diluted in PBS for 1 hour at RT. After washing cells were incubated with the biotinylated HLA class I/peptide complex (0.5 ug/ml in PBS) for 30 minutes at RT. Various controls, omitting the B9E9 scFvSA or the HLA class I/peptide complex were also performed. After washing, cells were placed into 24 well plates at 3×10⁶ cells per well and cultured in RPMI with 10% human AB serum. IL-7 (R and D Systems, Minneapolis, Minn.) was added on day 1 at 10 ng/ml and IL-2 (Chiron, Harefield, UK) was added at 10 U/ml on day 4 and every further 3 days following the method described by Lalvani (Lalvani et al, 1997). In the experiments with a second stimulation cycle further PBMCs were obtained and treated as above. These new cells were then mixed with the existing culture at a 1:2 ratio and the culture continued for a further 8 days.

Flow Cytometry and Tetramer Analysis

To stain CD8+ve cells from the PBMC culture approximately 1×10⁶ cells were washed in PBS, resuspended and incubated with tetramer solution for 30 minutes at 37° C. followed by FITC conjugated anti-CD8 for 20 minutes at 4° C. After incubation the cells were washed, resuspended in PBS and analysed by dual colour flow cytometry. The results of flow cytometry analysis of dual stained PBMCs are shown with anti-CD8 (Y axis) and HLA-A2/M1 tetramers (X axis). Percentage figures relate to the number of tetramer positive CD8 +ve cells from the total CD8+ve population.

Chromium Release Assay

Daudi or CIR-A2 cells were labelled with 2 uCi/uL of $^{51}Cr$ (Amersham Pharmacia, UK) for 1 hr at 37° C. then washed. Daudi cells were sequentially coated with B9E9 sfvScSA and HLA-A2/M1 complexes following the method above whilst CIR-A2 cells were pulsed with the peptide of choice at a concentration of 10 uM for 1 hr at 37° C. The target cells were plated at 3000 cells per well in U bottomed 96 well plates. PBMCs, media or 5% Triton X-100 were added to a final volume of 200 ul. Plates were incubated for 4 hours at 37° C. in a 5% $CO_2$ atmosphere and 5 ul of supernatant was collected and added to 150 ul of scintillant.

The specific lysis was calculated as:

$$\% \text{ lysis} = \frac{\text{experimental cpm} - \text{spontaneous cpm} \times 100}{\text{maximum cpm} - \text{spontaneous cpm}}$$

The spontaneous release was measured from the cells incubated in media alone, the maximum release was measured from the cells incubated in 5% Triton.

Results

1. Sequential analysis of the binding of biotinylated HLA-A2/M1 complexes to Daudi B-cell lymphoma cells via B9E9 scFvSA.

Figure 13:
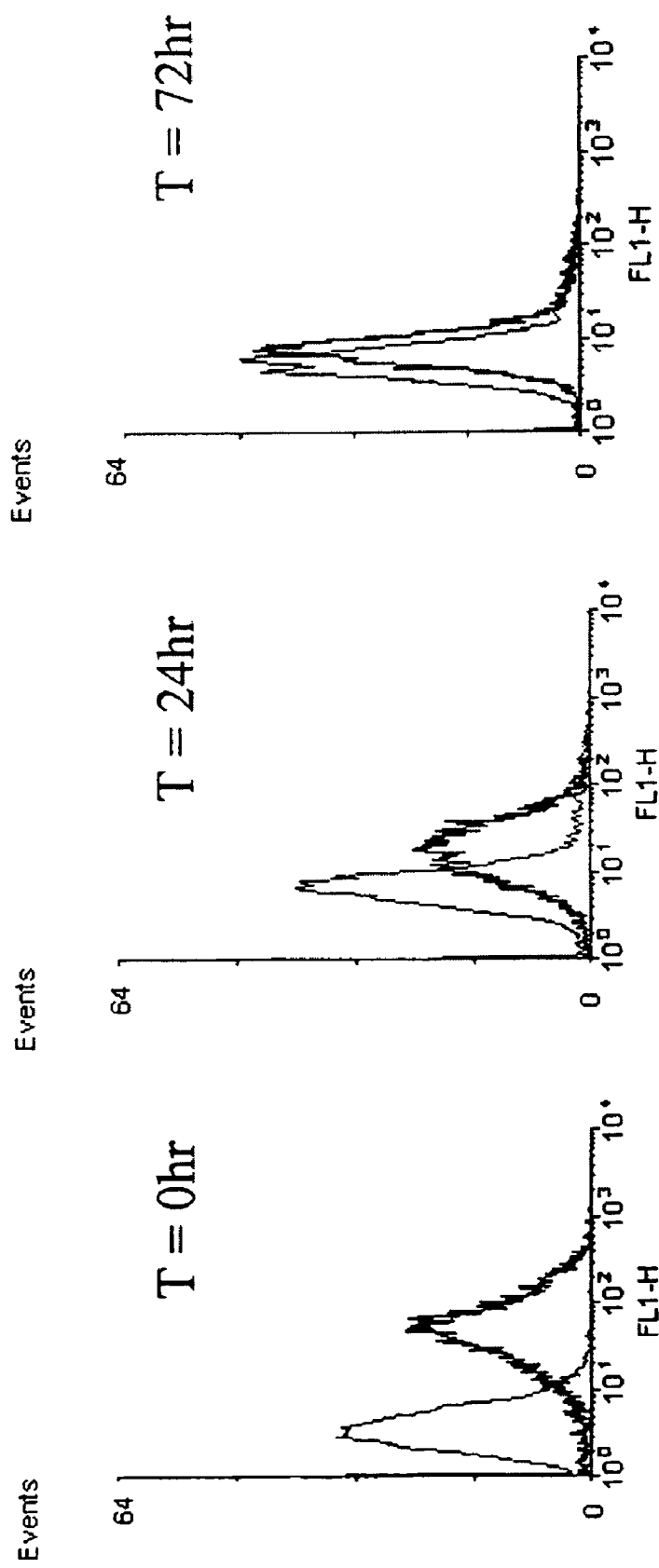
FIG. 13 shows time course analysis of HLA-A2/M1 complexes immobilized on the surface of HLA-class 1 −ve Daudi cells via B9E9 sfvScSA. Complexes are detected via the binding of W6/32 which binds conformationally correct HLA-class I. Daudi cells targeted with B9E9 sfvScSA alone are shown in grey, in black are Daudi cells targeted with B9E9 sfvScSA and HLA-A2/M1.

The time course of the retention of the targeted HLA-A2/M1 complexes retention the HLA class I −ve Daudi cells is demonstrated in the sequential flow cytometry analyses in FIG. 13. An increased fluorescence signal is demonstrated in the targeted cells which decreases with time. However a positive signal is still maintained at +72 hours and it is probable that HLA class I/peptide complexes persist at functional levels beyond this time.

2. Effects of B9E9 scFvSA binding on the expression of co-stimulatory molecules in PBMC B cells.

Figure 14:
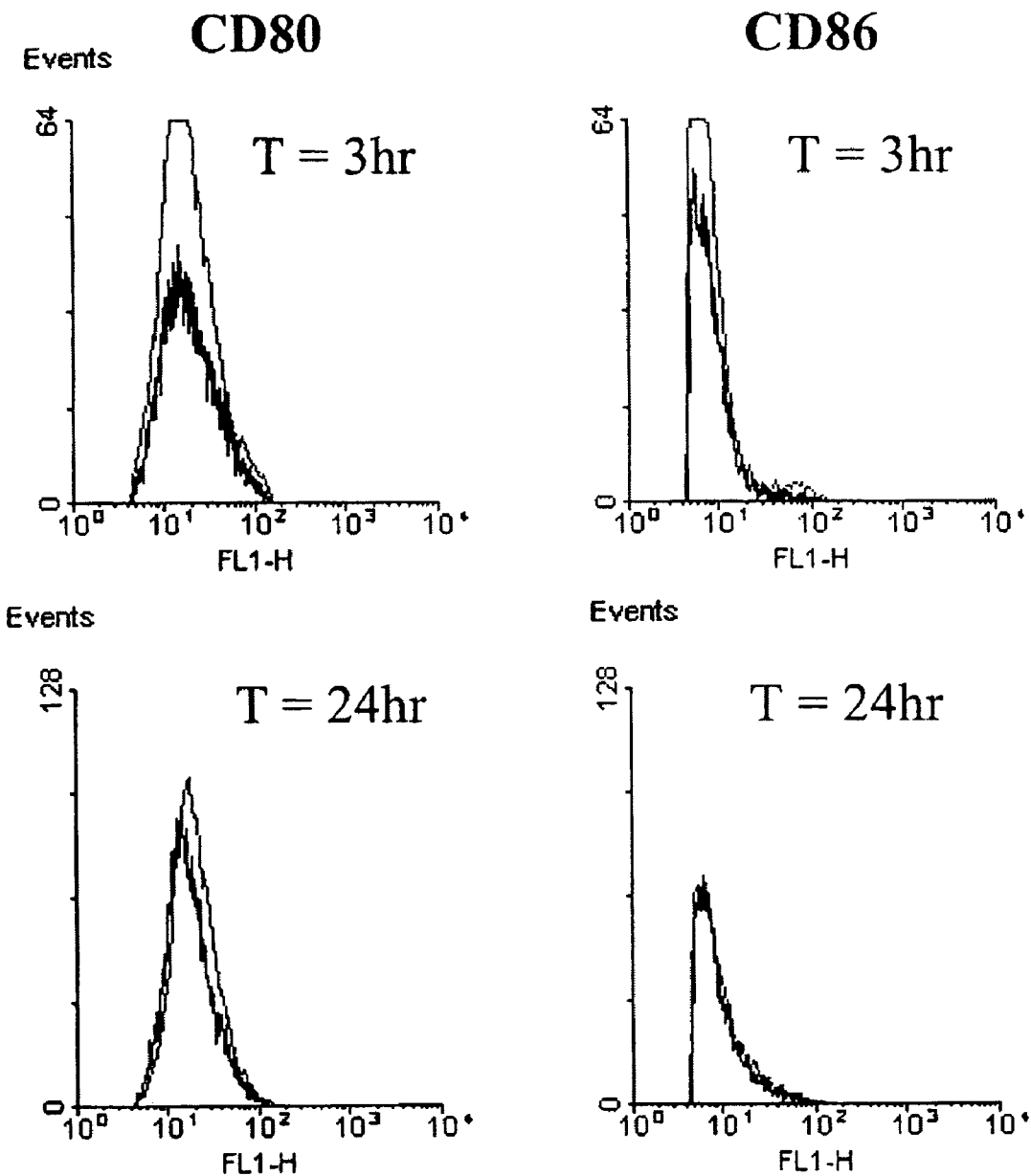
FIG. 14 shows sequential flow cytometry analysis of expression of CD80 and CD86 on CD 19+ve B cells within the PBMC population. The unstimulated controls are shown on the narrow trace, the experimental results from PBMCs targted with the B9E9 sfvScSA are shown in bold.

FIG. 14 demonstrates that the addition of B9E9 sfvScSA has no detectable effect on the expression of CD80 or CD86 on the B cells within the PBMC population. The results show the flow cytometry results for CD19+ve cells at 3 hrs and 24 hrs. PBMCs treated with IL-7 alone or the combination of B9E9 sfvScSA and IL-7 also demonstrated no change in the levels of expression of CD80 and CD86.

3a) Induction of CTL activity with targeted HLA class I/peptide complexes.

Figure 15:
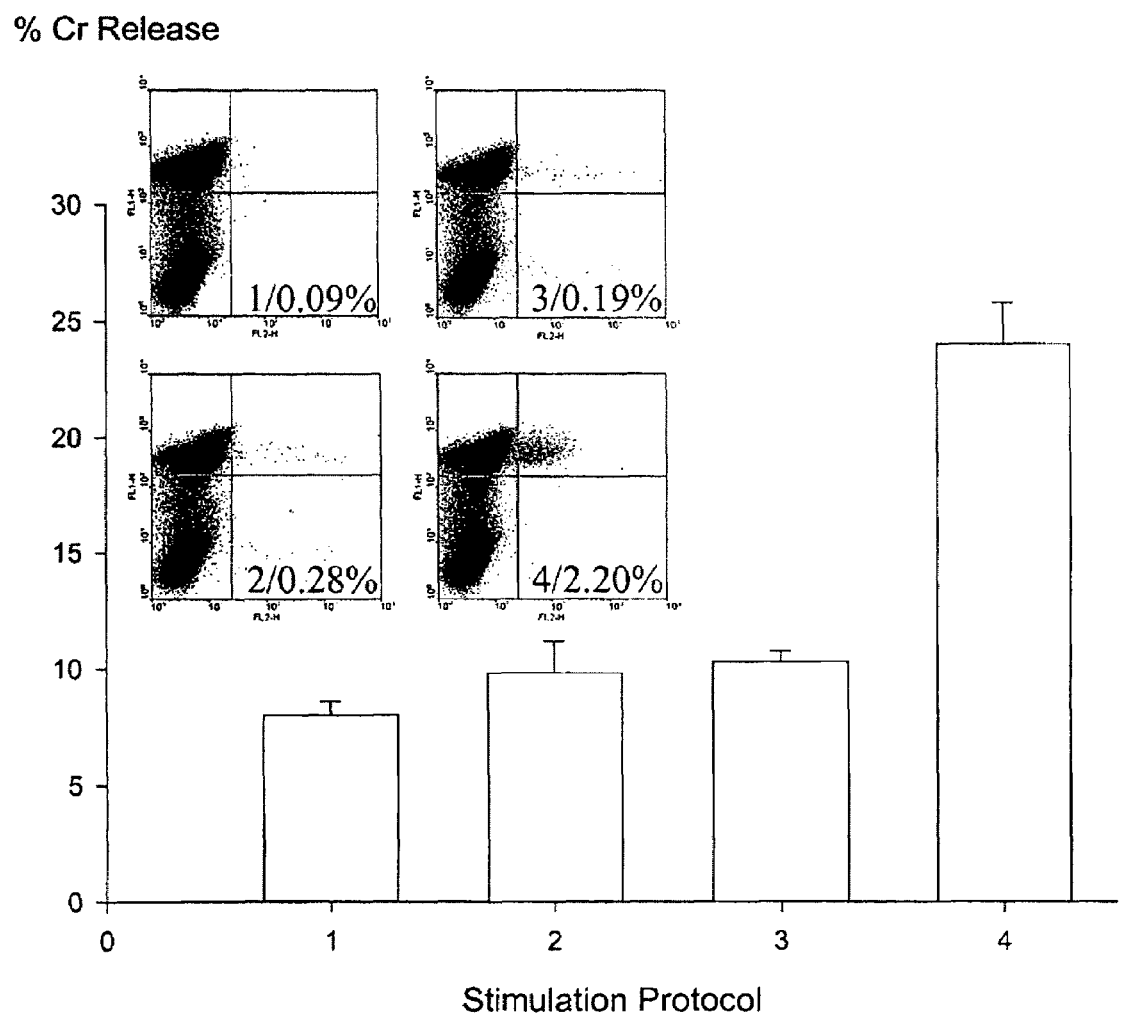
FIG. 15 shows FACs and Cr release assay results from PBMCs stimulated with targeted HLA-A2/M1 complexes. Tetramer results demonstrate staining with anti-CD8 and HLA-A2/M1 tetramer. The Cr release assay demonstrates activity against Daudi cells bearing HLA-A2/M1 complexes. Stimulation protocols: 1/PBMCs alone, 2/PBMCs+B9E9 sfvScSA, 3/PBMCs+free HLA-A2/BMLF1, 4/PBMCs+B9E9 sfvScSA+HLA-A2/BMLF1.

The ability of the antibody targeted complexes to stimulate CTL expansion was initially examined with the HLA-A2/M1 combination. In FIG. 15 the tetramer analysis of the CD8+ve/HLA-A2/M1 positive cells within the unstimulated PBMCs (1), PBMCs targeted with the B9E9 sfvScSA (2), and PBMCs exposed to free soluble HLA-A2/M1 complexes at 0.1 ng/ml (3) demonstrate values of 0.06% to 0.22%. In contrast the PBMCs targeted with the B9E9 sfvScSA and HLA-A2/M1 complexes (4) demonstrated 2.33% tetramer positive CD8+ve cells. Using the unfractionated PBMCs at E:T 10:1, a 4 hour Cr release assay, using HLA-A2/M1 coated Daudi cells as target cells, demonstrated a maximum of 10% lysis from the 3 control experiments but 24% from the PBMCs stimulated with HLA-A2/M1 complexes attached via the B9E9 sfvScSA fusion protein.

3b) Induced CTL responses are specific for the targeted complex.

To confirm the specificity of CTL expansion, PBMCs were targeted with either B9E9 sfvScSA alone (A) or B9E9 sfvScSA and HLA-A2/BMLF1 complexes (B).

Figure 16:
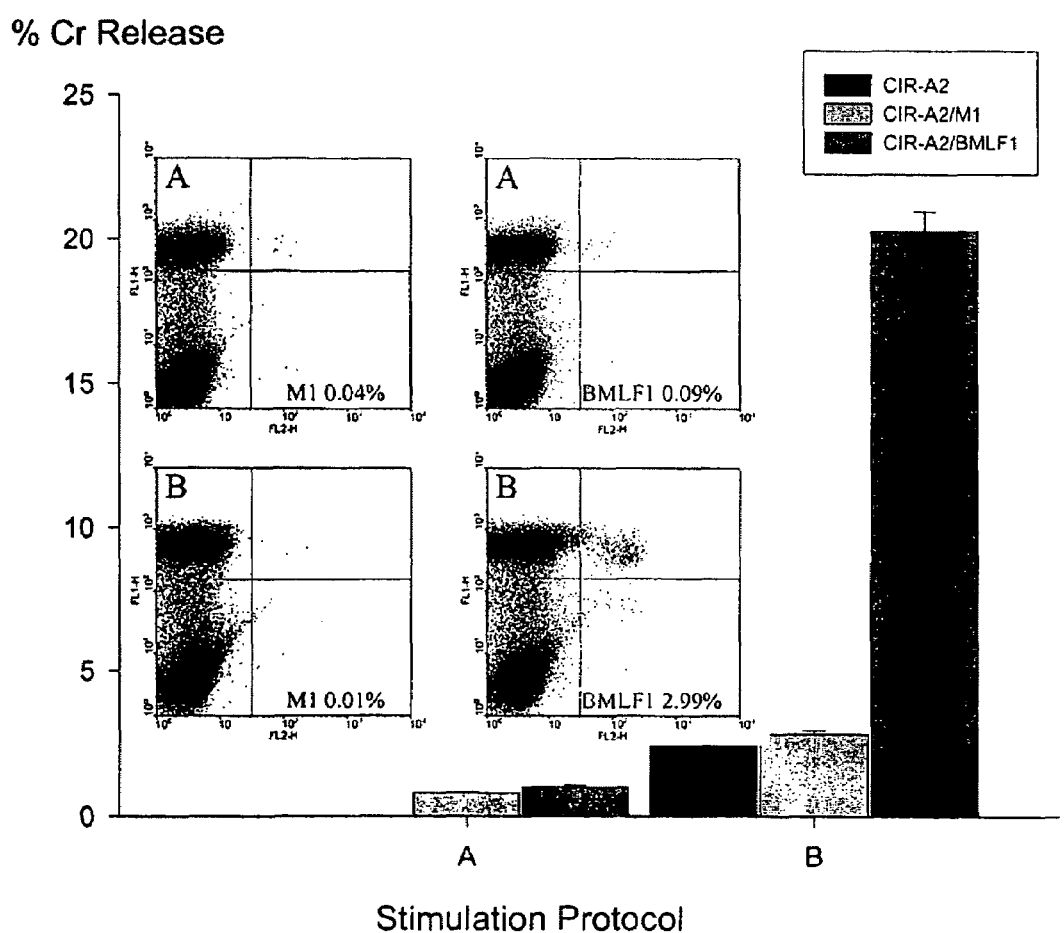
FIG. 16 shows FACs and Cr release assay results from PBMCs stimulated with either A) B9E9 sfvScSA alone or B) B9E9 sfvScSA and targeted HLA-A2/BMLF1 complexes. Tetramer staining results are shown for both HLA-A2/M1 and HLA-A2/BMLF1. The Cr release assay demonstrates PBMC at E:T 10:1 against native/M1/BMLF1 peptide pulsed CIR-A2 target cells.

In FIG. 16 the tetramer analysis of the PBMCs targeted with B9E9 sfvScSA alone demonstrates background staining of 0.04% with HLA-A2/M1 and 0.09% with HLA-A2/BMLF1. In the Cr release assay against CIR-A2 cells either native or pulsed with M1 or BMLF1 peptide the PBMCs showed no significant activity. In contrast PBMCs targeted with the HLA-A2/BMLF1 complexes demonstrate 2.99% staining with the HLA-A2/BMLF1 tetramer but with only a background staining level of 0.01% with the HLA-A2/M1 tetramer. These cells produced 20% lysis of the BMLF1 pulsed CIR-A2 target cells without any significant action on native or M1 pulsed cells.

3c) CTL responses to a single cycle of stimulation with HLA-A2/peptide complexes in healthy donors and melanoma patients.

The numerical values of the tetramer results from PBMCs from a series of healthy donors and melanoma patients are demonstrated in Table 13.

In response to stimulation with targeted HLA-A2/M1 complexes a greater than 5 fold increase in the number of tetramer+ve cells are seen in 6 of the 8 volunteers and one of two melanoma patients. From the HLA-A2/BMLF1 stimulated cells one of the 5 volunteers showed a greater than 5 fold increase with 2 others showing apparent increases. In response to targeted HLA-A2/Melan A complexes greater than 3 fold increases in tetramer positive cells were seen in 3 of 4 volunteers and in one of the melanoma patients.

TABLE 13

| Don | HLA-A2+M1 ($2^{nd}$ and $3^{rd}$ columns) + BMLF1 ($4^{th}$ and $5^{th}$ columns) + MelanA ($6^{th}$ and $7^{th}$ columns) | | | | | |
|---|---|---|---|---|---|---|
|  | 0 | 1 | 0 | 1 | 0 | 1 |
| RT | 0.21 | 1.08 | 0.54 | 0.63 | — | — |
| SL | 0.04 | 0.41 | 0.28 | 0.26 | — | — |
| JaR | 0.00 | 0.32 | 0.30 | 0.85 | — | — |
| LO | 0.00 | 0.01 | 0.08 | 0.31 | — | — |
| LL | 0.09 | 2.20 | 0.09 | 2.99 | 0.06 | 0.26 |
| CJ | 0.16 | 0.57 | — | — | 0.04 | 0.13 |
| JuR | 0.07 | 0.52 | — | — | 0.09 | 0.08 |
| DV | 0.07 | 0.80 | — | — | 0.03 | 0.14 |
| BB* | 0.00 | 0.22 | — | — | 0.41 | 1.33 |
| DB | 0.36 | 0.91 | — | — | 0.42 | 0.21 |

Figure 17:
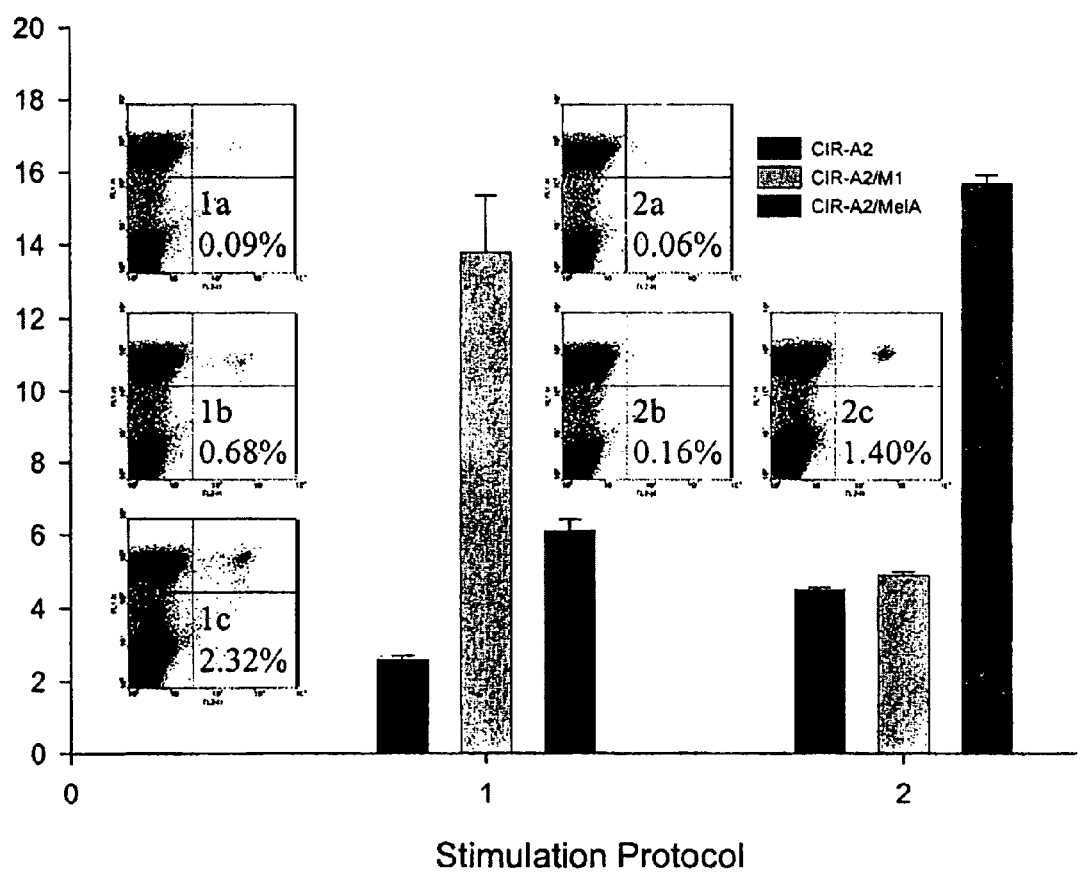
FIG. 17 shows FACs and Cr release assay results from PBMCs stimulated twice with either 1) targeted HLA-A2/M1 complexes or 2) targeted HLA-A2/Melan A complexes. Tetramer results are a/unstimulated, b/targeted once and c/targeted twice. The Cr release assay with twice targeted PBMCs shows the activity against native and peptide pulsed CIR-A2 cells at E:T 20:1.

3d) CTL responses to HLA-A2/M1 and Melan A can be enhanced by a repeated stimulation FIG. 17 demonstrates the CTL responses produced by 2 rounds of in vitro stimulation using the same HLA-A2/peptide complex. The 4 hr Cr release assay (E:T 20:1) demonstrates that PBMCs stimulated with targeted HLA-A2/M1 complexes on both day 1 and day 8 produce 14% lysis of the CIR-A2 M1 pulsed cells compared with 3% lysis of native and 6% lysis of CIR-A2 melanA pulsed cells. The increase in HLA-A2/M1 specific CTLs is shown in the tetramer series with 0.09% from unstimulated cells (1A), 0.68% after one cycle (1B) and 2.32% after two cycles (1C). In this donor similar results were seen with responses to melan A with a 15% lysis of CIR-A2 cells pulsed with the Melan A peptide and increases in tetramer staining from a background of 0.06%, 0.16% after one cycle and 1.40% after two cycles. In this experiment cycles subject to one cycle of stimulation did not produce detectable activity in the Cr release assay.

Discussion

The induction of an effective immune response against malignant cells has been an aim of cancer research for over a century. With the increasing understanding of how the immune system may differentiate between normal and malignant cells a number of cancer vaccine approaches have been examined. To date many of these have centred on the use of undefined antigens via tumour cell lysates or irradiated cells. However with the identification of a number of potential tumour peptide epitopes (Boon and van der Bruggen, 1996, Vonderheide et al, 1999) and the ease. of manufacture of recombinant HLA class I peptide complexes (Garboczi et al, 1992) it is now feasible to consider highly specific approaches to cancer vaccine strategies.

Purified immobilised HLA class I/peptide complexes have been shown to interact and stimulate CTLs when attached to tissue culture plates (Kane et al, 1989), chemically attached to cells (Anjeure et al, 1995, Walter et al, 1997) or when coated onto beads (Motta et al, 1998). More recently antibody targeted HLA class I/peptide complexes have been demonstrated to successfully interact with CTLs to permit lysis of targeted cells in vitro (Ogg et al, 2000, Robert et al, 2000).

The ability of B cells targeted with HLA class I/peptide complexes to induce CTL responses is clearly shown in FIGS. 15, 16 and 17. In vitro CTL responses demonstrated by tetramer and Cr release assays were obtained when the HLA class I/peptide complexes were targeted to PBMCs pre-treated with the B9E9 sfvSA fusion protein. In contrast free HLA class I/peptide complexes produced no apparent responses indicating a requirement for either multimerisation or immobilisation of HLA class I/peptide complexes for effective CTL stimulation as previously described (Motta et al, 1998, Abastado et al, 1995).

The specificity of the CTL expansion is confirmed by the results shown in FIG. 16 where increases in tetramer staining and lysis of peptide pulsed target cells was only seen in response to stimulation with that specific HLA/peptide complex.

The ability of this system to further increase responses by repeated stimulation is shown in the tetramer stain results of FIG. 17. Here the frequencies of CTLs reactive with HLA-A2/M1 increase from 0.09% to 2.32% after a second cycle. In this donor the MelanA results of 0.06% and. 1.4% show as similar pattern, with positive Cr release assays after 2 cycles.

The efficiency of CTL induction, has previously been shown to be related to the stability and length of expression of the HLA class-I complex on the surface of antigen presenting cells (van der Burg et al, 1996, Micheletti et al, 1999, Valmori et al, 1998). In this antibody targeting system we have aimed to optimise the time course for expression of the HLA class I complexes, by using complexes with long half lives and a high affinity binding system to a non-internalising B cell marker. The ability of these complexes to persist in a conformationally correct form for at least 72 hours on the surface of the B cells is demonstrated in FIG. 13. It is probable that functionally active levels of complexes remain on the surface of the B cells for a longer period, we have previously shown that CTLs interact efficiently with B cells with levels of targeted HLA below that detectable by cytometry (Savage et al, 2002).

The data in FIG. 14 demonstrates that binding of the B9E9 sfvScSA to the B cells within the PBMCs either alone or in conjunction with IL-7 had no effect on the expression of B80 and B86. Whilst the enhanced expression of co-stimulatory molecules generally increases CTL responses, it has previously been demonstrated that effective CTL can be produced without accessory molecule expression, particularly when high epitope densities are used (Wang et al, 2000).

At present there has been only limited optimisation of this in vitro stimulation protocol with significant differences in the levels of CTL responses between individuals. However in all experimental cultures using targeted HLA class I/peptide complexes significant inhibition of proliferation compared to those targeted with the B9E9 fusion protein alone was observed (data not shown). It is possible that the effect of the supra-physiological stimulation prevents expansion of the specific CTL population either via a direct apoptotic action or the result high levels of cytokine production within the closed system. Studies in mice have shown that increased antigenic density can result in higher CTL activity but produces a significant reduction at very high densities (Wherry et al, 1999). Similarly in human systems the presence of supra-optimal levels of HLA class I complexes can lead to apoptosis rather than expansion of stimulated CD8+ve CTLs (Alexander-Miller et al, 1998). As CD20 is present at approximately 50,000 copies per B cell (Marti et al, 1992), saturated binding of HLA class I/peptide complexes could result in 50,000-200,000 copies of a single peptide/HLA class I combination per cell. This is significantly higher than produced by peptide pulsing which results in peptide placement in 5,000 copies of an individual HLA allele (Delon et al, 1998) out of a total allele number of $10^5$ per B cell. (Kageyama et al, 1995, McCune et al, 1975) Additionally the stability of the recombinant complexes appears to be greater than those produced by peptide pulsing which have an average ½ life of only 2.5-4 hrs (Wataya et al, 2001) which may further increase the strength and duration of T cell activation.

The ability of this system to specifically induce the expansion of CTLs to a specific peptide/HLA-class I complex will prove useful for in vitro studies analysing the endogenous CTL response or the effects of other in vivo procedures. Potentially this system could also be used for the ex vivo production of CTLs for the adoptive immunotherapy of cancer and other diseases. However a vaccination procedure based on targeting HLA class I/peptide complexes to APCs in vivo via an antibody delivery system could offer significant advances in both the applicability and effectiveness of cancer vaccines.

The B9E9 sfvSA fusion protein is currently in clinical trials for the treatment of B cell lymphoma using radiolabelled biotin as the effector function. The ease of administration, lack of toxicity and option for repeated doses suggest that using this molecule in a vaccine strategy should be feasible. To date recombinant HLA class I molecules are yet to be administered to cancer patients, however as endogenous HLA class I molecules circulate in health and in increased levels in a number of illnesses (McMillan et al, 1997) they are unlikely to have any direct toxicity.

In this work we have focused on stimulation with a single HLA class I/peptide complex, however the ability to make these recombinant molecules of any chosen HLA class I/peptide combination should allow for vaccination with a range of complexes either sequentially or concurrently. As the stability of the HLA class I/peptide complexes appears to varying considerably with the identity of the peptide (Valmori et al, 1998) and stability is closely linked to the immunogenicity of a chosen HLA class I/peptide complex, it is possible that recombinant molecules that incorporate the peptide/ HLA heavy chain/beta-2-microglobulin into fusion proteins may offer potential benefits.

Currently optimisation of the level of targeted HLA class I/complexes on the targeted B cells and the cytokine support for the most effective stimulation and induction of CTL responses in vitro is being examined. Potential clinical studies will initially use PBMCs targeted with complexes ex vivo, which will allow accurate administration of designated numbers of targeted cells at the opyimum epitope density. Considering the potential clinical applicability of this system, it is probable that initially PBMCs will be targeted with complexes ex vivo, potentially via a closed leucapheresis system. This approach should also minimise the potential immunogenicity of the streptavidin in the fusion protein and the potential risk of uncontrolled CTL expansion that could occur with intravenous. HLA classI/complex administration that would result in the targeting of the total B cell population.

Summary

The production of cytotoxic T cells (CTLs) with specificity for cancer cells is a rapidly evolving branch of cancer therapeutics. A variety of approaches aim to amplify anti-tumour CTL responses using purified peptides, tumour cell lysates or recombinant HLA/peptide complexes in differing antigen presenting systems.

Using a two-step biotin-streptavidin antibody targeting system, recombinant HLA-class I/peptide complexes were attached to the surface of B cells via the anti-CD20 B9E9-scFvSA antibody-streptavidin fusion protein. Flow cytometry with a conformation dependant monoclonal antibody to HLA class I indicated that targeted HLA-class I/peptide complexes remain on the surface of B cells in culture for periods in excess of 72 hours. PBMCs were stimulated in vitro for 8-14 days using the autologous B cells as antigen presenting cells. Following a single cycle of stimulation specific CTL responses to targeted HLA-A2 complexes containing the M1, BMLF1 and Melan A peptides could be demonstrated by tetramer staining and Cr release assays. With the HLA-A2/BMLF1 complex up to 2.99% of CD8+ve cells were tetramer positive producing 20% lysis (E:T 10:1) of CIR-A2 target cells in an in vitro cytotoxicity assay compared to baseline levels of 0.09% tetramer +ve and 2% lysis in the unstimulated population.

PBMCs from a healthy donor treated with two cycles of stimulations with targeted HLA-A2/Melan A complexes, demonstrated expansion of the melanA tetramer+ve population from 0.03% to 1.4% producing 15% lysis of Melan A pulsed target cells.

With further consideration to the key variables of HLA/peptide complex density, the ratio of stimulator to effector cells and optimum cytokine support, this system should offer an easy and effective method for the in vitro amplification of specific CTL responses and warrants development for the in vivo induction of CTL responses in cancer therapy.

Example 6

Treatment of a Blood Sample

Protocol for the ex vivo preparation and re-administration of autologous B cells treated with antibody targeted HLA class I/peptide complexes.

1) Take 600 ml of venous blood into standard transfusion bag

2) Transfer to blood transfusion laboratory for work in sterile GLP conditions

3) Centrifuge to prepare 'buffy' coat from 600 mls of whole blood

4) Wash in sterile PBS×1

5) Resuspend in 50 mls sterile PBS

6) Incubate with B9E9 sfvscSA at 10 ug/ml for 30 minutes at room temperature

7) Wash in sterile PBS×3

8) Resuspend in 50 mls sterile PBS.

9) Incubate with biotinylated HLA class I/peptide complex(es) at 0.5 ug/ml for 10 minutes at room temperature.

10) Wash in sterile PBS×1

11) Resuspend in 50 mls of sterile PBS
12) Re-infuse into patient via peripheral venous access over 10 minutes.

Example 7

Method for Producing Antipeptide Cytotoxic T Lymphocytes (CTLs)

Method
Purify PBLs from donor (HLA-A2–ve).
Mix with sfvSA (to CD20).
Add HLA-A2/peptide monomer.
Wash off excess.
Incubate for 7 days with IL-7 and IL-2.
Repeat after 7 days.

Figure 18:
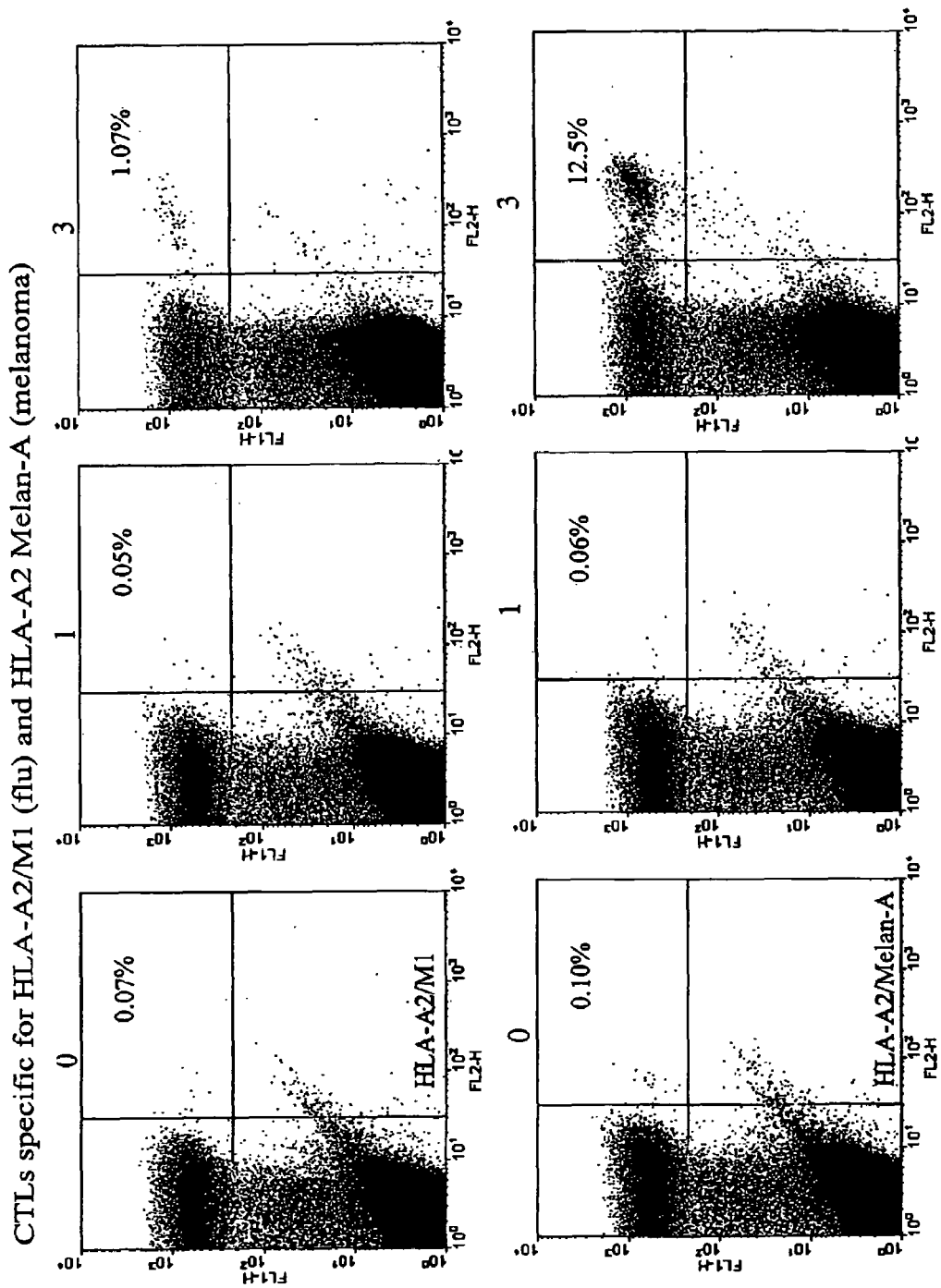
FIG. 18 shows six plots (donor MG HLA-A2 negative) of CTLs which are specific for HLA-A2/M1 (flu) and HLA-A2 Melan-A (melanoma) as measured after 0, 1 or 2 rounds of stimulation.
Figure 19:
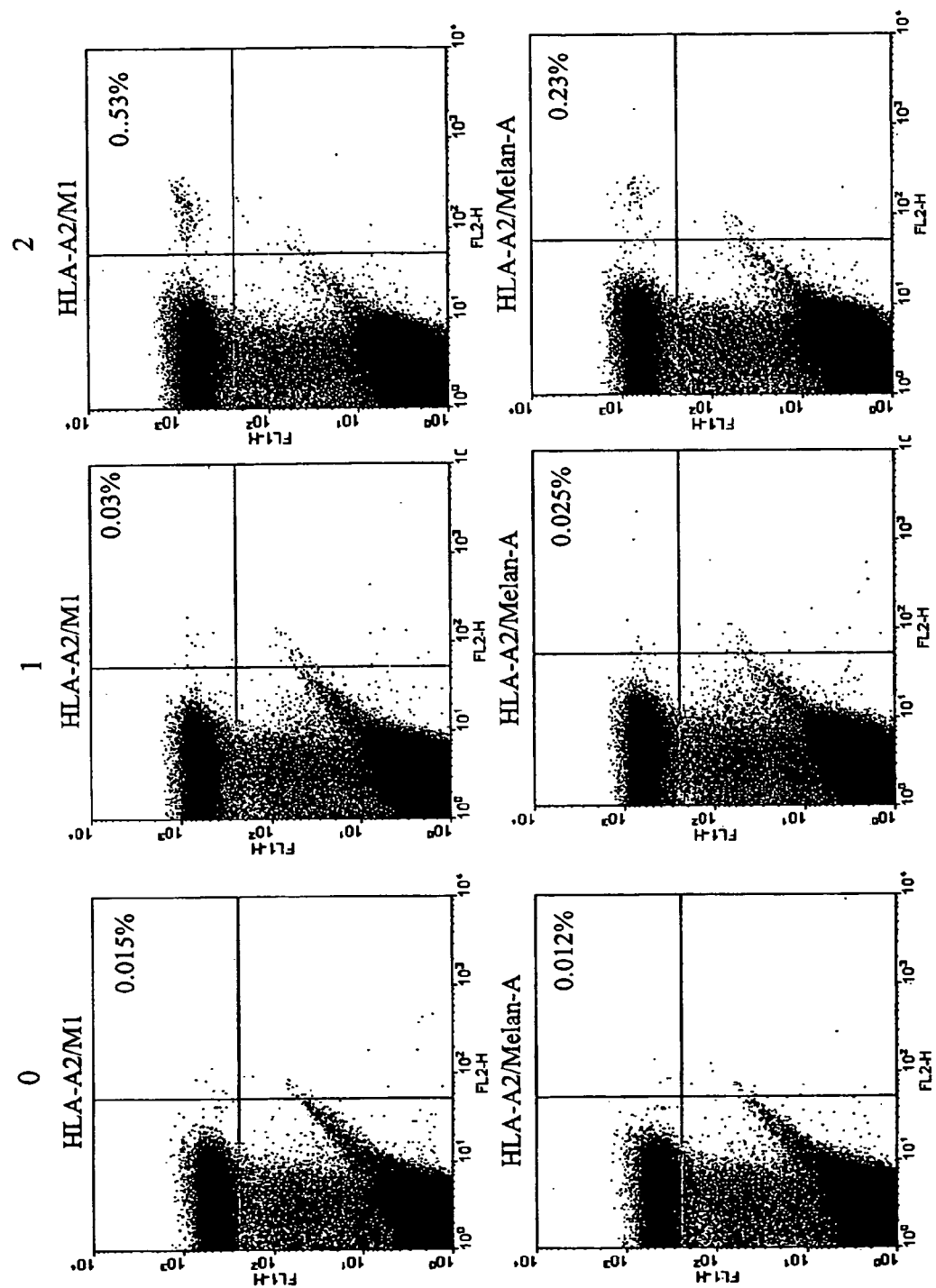
FIG. 19 shows six plots (three HLA-A2/M1 and three HLA-A2/Melan-A) after 0, 1 and 2 rounds of stimulation (see example 7).

Results
FIG. 18 shows CTLs, according to the present invention, which are specific for HLA-A2/M1 (flu) and HLA-A2 Melan-A (melanoma) as measured after 0, 1 or 2 rounds of stimulation.

Example 8

Method for Producing Antipeptide Cytotoxic T Lymphocytes (CTLs)

Figure 20:
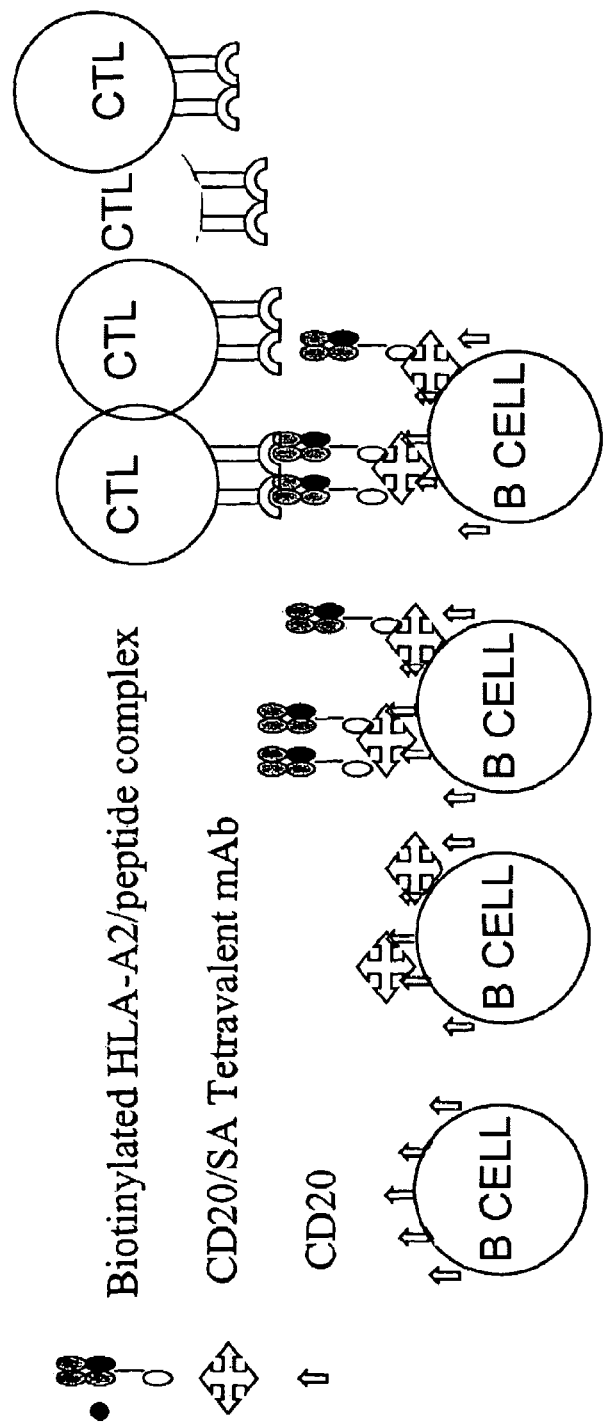
FIG. 20 shows a schematic representation of the two step targeting system delivering HLA-A2/peptide complexes to the surface of B cells from HLA-A2 −ve donors. The presence of the immobilised complexes on the B cells leads to expansion of alloreactive CTL populations.

An in vitro method to produce alloreactive CTLs against a designated HLA class I/peptide combination is demonstrated. In this Example, HLA-A2/Melan-A is used. FIG. 20 helps to illustrate this embodiment of the invention.

Method
PBLs from healthy HLA-A2 –ve donors were purified by HISTOPAQUE (density gradient medium) centrifugation.
B9E9 scFvSA were incubated in PBS at 10 μg/ml for 1 hour at room temperature (RT) and then washed.
Biotinylated HLA-A2/Melan-A were complexed at 0.5 μg/ml for 30 minutes at RT and then washed.
Cells were plated in 24 well plates at $3 \times 10^6$ cells per well in RPMI with 10% AB serum.
IL-7 was added on day 1 at 10 ng/ml.
IL-2 was added at 10 U/ml on day 4 and every further 3 days.
Cells underwent 1, 2, 3 cycles of stimulation.
Read-out analysis by Tetramer/CD8 staining and $^{51}$Cr release assay using peptide pulsed T2 cells was performed.

Figure 21:
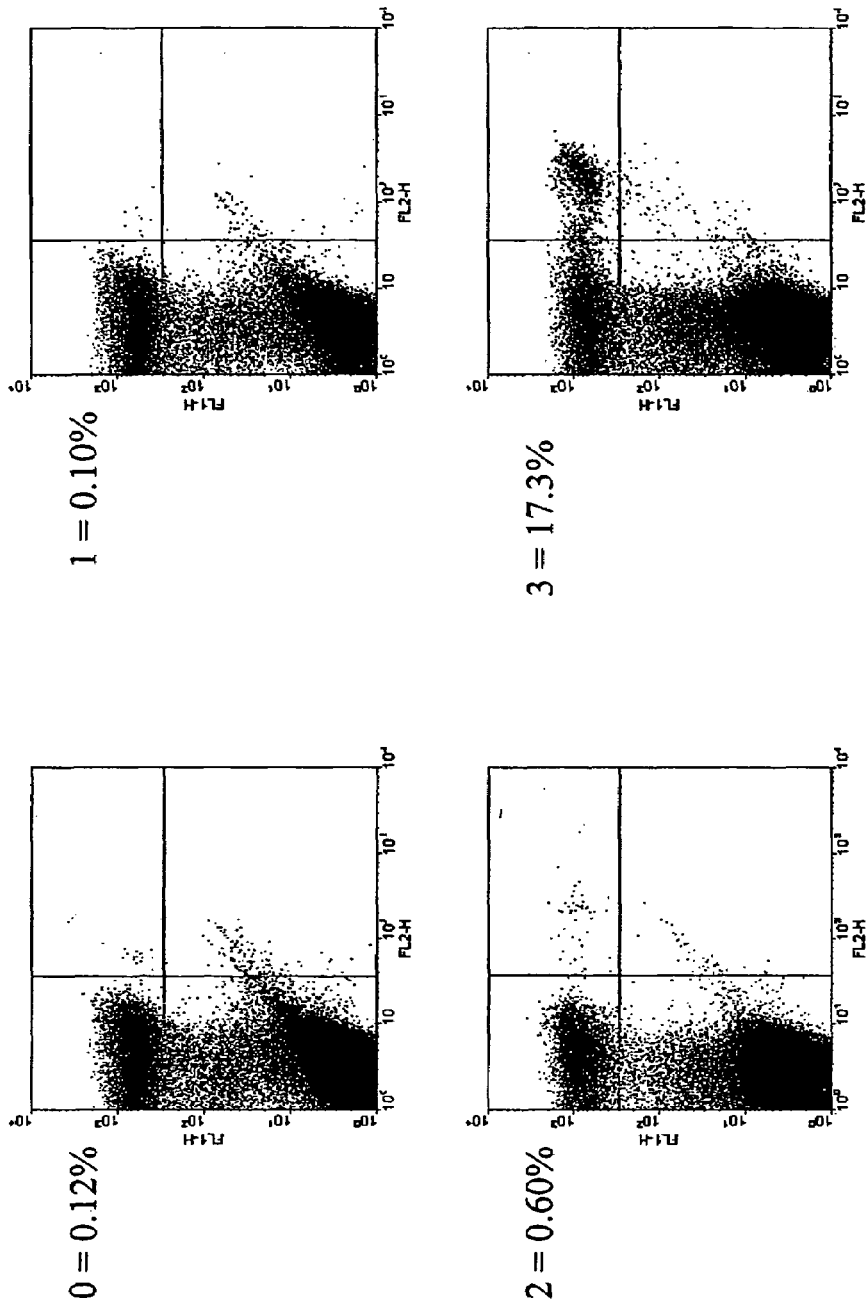
FIG. 21 shows four plots (0, 1, 2 and 3) demonstrating the increasing population of CTLs through cycles of stimulation from 0.12% at 0 cycles to 17.3% after 3 cycles, demonstrated by Tetramer staining with HLA-A2/MelanA tetramer.
Figure 22:
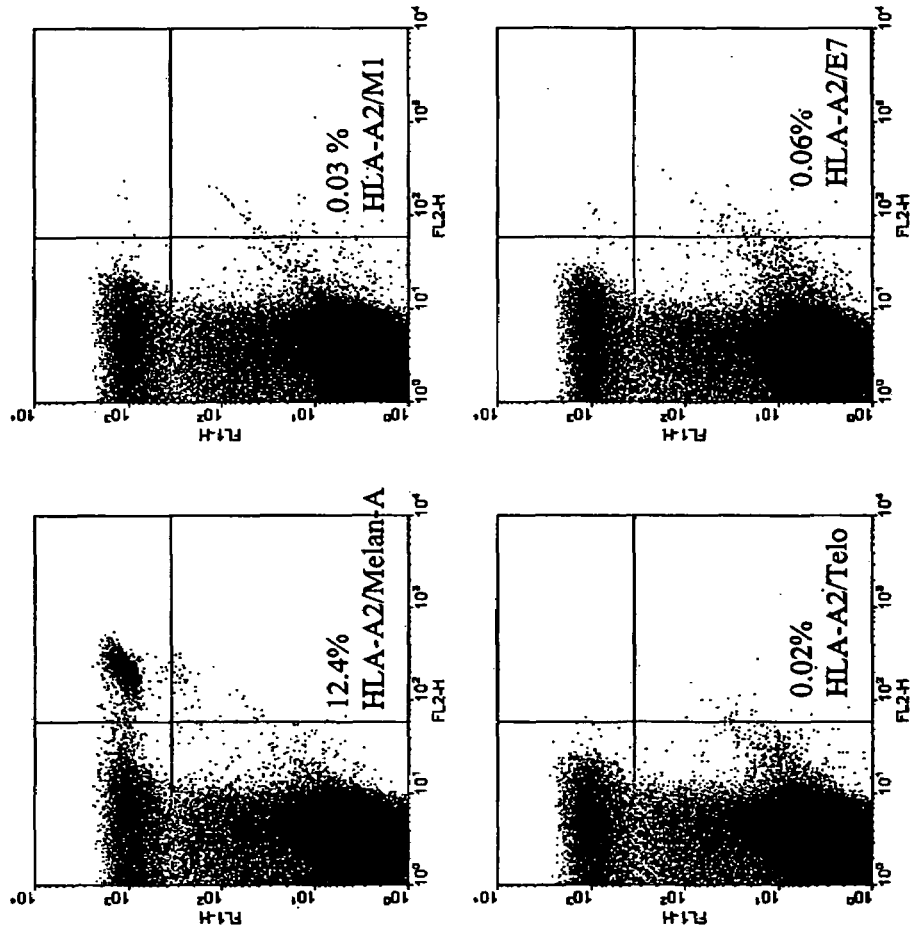
FIG. 22 shows four plots (Melan-A, M1, Telo and E7) demonstrating the specificity of CTLs for the target HLA-A2/peptide complex.

Results
FIGS. 21 and 22 illustrate the efficient production and specificity of CTLs produced according to the present invention. FIG. 21 shows the increasing population of CTLs through cycles of stimulation from 0.12% at 0 cycles to 17.3% after 3 cycles. FIG. 22 shows specificity of CTLs according to the present invention for the target HLA-A2/peptide complex.

Thus it can be seen that the methods of the present invention produce high outputs of CTLs. It further demonstrates that CTLs produced according to the present invention exhibit excellent reactivity with the target complex.

Example 9

Production of Anti-tumour Alloreactive T Cells using Antibody Targeted HLA Class I/peptide Complexes Outline
The effective production of CTLs that recognise clinically important HLA class I/peptide. combinations. is demonstrated herein.

Using recombinant HLA-A2 class I/peptide complexes targeted to autologous B cells of HLA-A2+ve donors, it is demonstrated that specific CD8+ve CTLs can be made from peripheral blood mononuclear cells (PBMCs). Using this technology to deliver HLA-A2/peptide complexes to the surface of the B cells in PBMCs from HLA-A2 –ve donors, we have demonstrated the production of alloreactive CTLs against HLA-A2. Using PBMCs stimulated with targeted HLA-A2/Melan-A complexes, tetramer staining demonstrated that the HLA-A2/Melan-A tetramer positive proportion of the CD8+ve cells increased from 0.12% prior to stimulation to 15.1% after 3 weekly cycles of stimulation.

The specificity of alloreactive CTLs produced to HLA-A2/MelanA and HLA-A2/WT1 from two donors was demonstrated by staining with a panel of HLA-A2 tetramers.

From donor PS the CTLs produced to the HLA-A2/Melan-A and WT1 complexes only produced significant staining with the appropriate tetramer.

From donor BQ, the CTLs produced against HLA-A2/Melan-A stained only with that tetramer, but in contrast, the CTLs produced against HLA-A2/WT1 demonstrated comparable levels of binding to each of the panel of tetramers.

This difference in specificity was reflected in functional Cr release assays. Cells from donor PS showed a significant degree of specificity whilst the WT1 cells from donor BQ demonstrated no peptide specificity.

The ability to simply produce large numbers of alloreactive CTLs with targeted recombinant HLA class I/peptide complexes preferably to GMP standards offers a number of therapeutic and scientific possibilities. Thus the invention further relates to the production of alloreactive cells for adoptive immunotherapy, the cloning of T cell receptor genes from high affinity alloreactive CTLs, the screening of allograft donors for the ease and specificity of production of CTLs against designated targets and the investigation of the molecular mimicry between HLA class I/peptide complexes.

Background
In comparison to normal cells, malignant cells may have differences in the immunogenic peptides displayed within the peptide binding grove of their HLA class I molecules. These immunological differences give the potential for therapies based on enhancing specific T. cell mediated immune responses to these cells (Pardoll 2000). The increasing description of more tumour specific and tumour related HLA class I binding peptides is now further encouraging the development of T cell mediated immunotherapy directed against these defined targets (Rosenberg 1996).

In some malignancies, the existence of pre-existing low levels of CTLs reactive with a number of tumour related HLA class I/peptide combinations has already been demonstrated and these epitopes may be the most suitable for autologous cancer vaccine studies (Pittet 1999). However, due to immunological tolerance, it is difficult to produce autologous high affinity CTLs to many other HLA class I/peptide combinations.

A therapeutic approach of the present invention aimed at overcoming tolerance, is to make high affinity alloreactive anti-tumour CTLs which can recognise these targets (Sadovnikova 1998). This is demonstrated herein.

These CTLs are expanded for use in adoptive immunotherapy. They are also useful in gene delivery mediated immunotherapy using the cloned T cell receptor. (Gao 2000, Stanislawski 2001, Kessels 2001).

The clinical value of alloreactive anti-tumour CTLs can already be seen in leukaemia patients who receive donor bone marrow transplants. Here the production of an alloreactive CTL mediated graft versus leukaemia activity within the graft versus host activity is associated with an enhanced prognosis (Molldrem 2000) and currently a number of projects are in progress which aim to separate these two immunological effects.

As explained above, existing methods of production of alloreactive CTLs frequently rely on the use of antigen presenting cells. such as peptide pulsed T2 or HLA class I transfected Drosophila cells (Moris 2001 Sadovnikova 1998, Dutoit 2002). These systems have a number of limitations including; modest immunostimulatory actions, potential HLA mismatches at more than one allele, the lack of GMP standard reagents and also a lack of flexibility to present other than HLA-A2. In the autologous setting, antibody targeted HLA class I complexes delivered to B cells are effective in the production of autologous CTLs against the targeted complex (Savage et al 2002). In this example, application of antibody targeted HLA class I complexes to produce allorereactive CTL responses to HLA-A2/peptide complexes from PBMCs from non-HLA-A2 donors is described. (See FIG. 20.)

Materials and Methods

Antibodies and cells

The B9E9 anti-CD20 sfvscSA fusion protein (Schultz et al. 2001) was obtained from NeoRx Corp, Seattle USA.

HLA-A2+ve T2 (Salter 1985) cells were grown in RPMI+ 10% FCS supplemented with penicillin and streptomycin in a 37° C. incubator with 5% $CO_2$.

Venous blood was obtained from tissue typed healthy volunteers. (MG HLA A1, A1, B8, B44. PS HLA A3, A24, B35, B57. BQ HLA A1, A26, B7, B27). Unfractionated PBMCs were isolated by differential centrifugation using Histopaque (Sigma, Poole, UK).

HLA-A2/peptide Complex Monomers and Tetramers

Recombinant HLA-A2 class I monomers and fluorescent tetramers were obtained from ProImmune Ltd, (Oxford Science Park, Oxford UK). The peptides used in these experiments were Influenza virus M1 peptide GILGFVFTL (SEQ ID NO: 4) (Gotch et al. 1987), the modified melanoma associated Melan A peptide ELAGIGILTV (SEQ ID NO: 6) (Valmori et al. 1998), the WT1 p126 peptide RMFPNAPYL (SEQ ID NO: 7) (Oka et al. 2000), the telomerase p540 eTRT peptide ILAKFHWL (SEQ ID NO: 8) (Minev et al 2000) and the HPV16 E7 11-20 peptide (YMLDLQPETT) (SEQ ID NO: 9) (Ressing et al. 1995)

In vitro immunisation protocol

PBMCs were incubated with the B9E9 scFvSA (10 μg/ml) diluted in PBS for 1 hour at room temperature. After washing, cells were incubated with the biotinylated HLA class I/peptide complex (0.5 ug/ml in PBS) for 30 minutes at room temperature. After washing, cells were placed into 24 well plates at $3 \times 10^6$ cells per well and cultured in RPMI with 10% human AB-serum. IL-7 (R and D Systems, Minneapolis, Minn.) was added on day 1 at 10 ng/ml and IL-2 (Chiron, Harefield, UK) was added at 10 U/ml on day 4 and every further 3 days, following the method described by Lalvani et al. (1997). For further stimulation cycles, fresh PBMCs were obtained and treated as above. These new cells were then mixed with the existing culture at a 1:2 ratio, and the culture was continued for a further 7 days.

Flow cytometry and Tetramer analysis

To stain CD8+ve cells from the PBMC culture, approximately $1 \times 10^6$ cells were washed in PBS, resuspended and incubated with tetramer solution for 30 minutes at 37° C., followed by FITC conjugated anti-CD8 for 20 minutes at 4° C. After incubation, the cells were washed, resuspended in PBS and analysed by dual colour flow cytometry. The results of flow cytometry analysis of dual stained PBMCs are shown with anti-CD8 (y axis) and HLA-A2/M1 tetramers (x axis). Percentage figures relate to the number of tetramer positive CD8+ve cells from the total CD8+ve population.

Chromium release assay

T2 cells were labelled with 2 μCi/μL of $^{51}Cr$ (Amersham Pharmacia, UK) for 1 hr at 37° C., and then washed and pulsed with the peptide of choice at a concentration of 10 μM for 1 hr at 37° C. The target cells were plated at 3000 cells per well in U bottomed 96 well plates. PBMCs, media, or 5% Triton X-100 were added to a final volume of 200 μl. Plates were incubated for 4 hours at 37° C. in a 5% $CO_2$ atmosphere and 50 μl of supernatant was collected and added to 150 μl of scintillant.

The specific lysis was calculated as:

$$\% \text{lysis} = \frac{\text{experimental cpm} - \text{spontaneous cpm}}{\text{maximum cpm} - \text{spontaneous cpm}} \times 100$$

The spontaneous release was measured from the cells incubated in media alone, the maximum release was measured from the cells incubated in 5% Triton.

Example 9.1

Timecourse of Alloreactive CTL Production

Figure 23A:
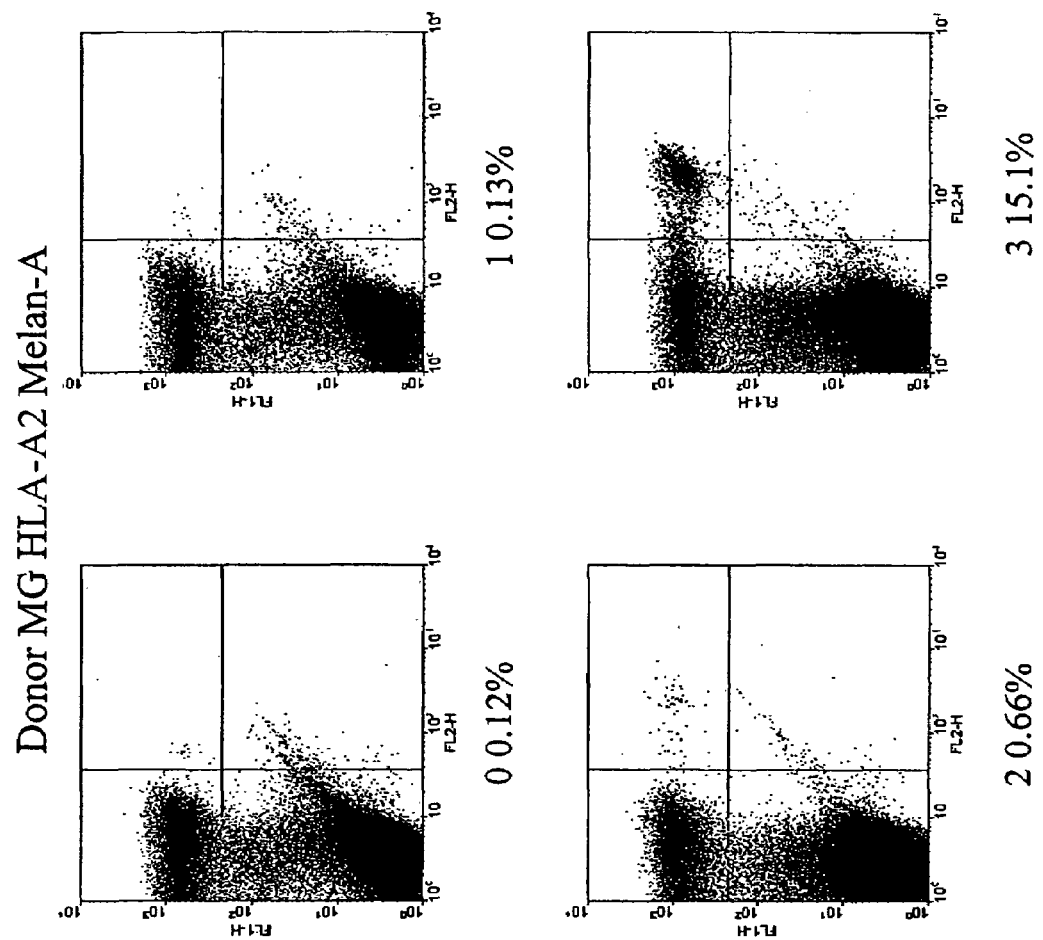
FIG. 23 shows Donor MG Tetramer analysis of PBMCs demonstrating the increasing numbers of tetramer positive cells with repeated cycles of stimulation with targeted HLA-A2/Melan-A (23a) or HLA-A2/M1 (23b).
Figure 23B:
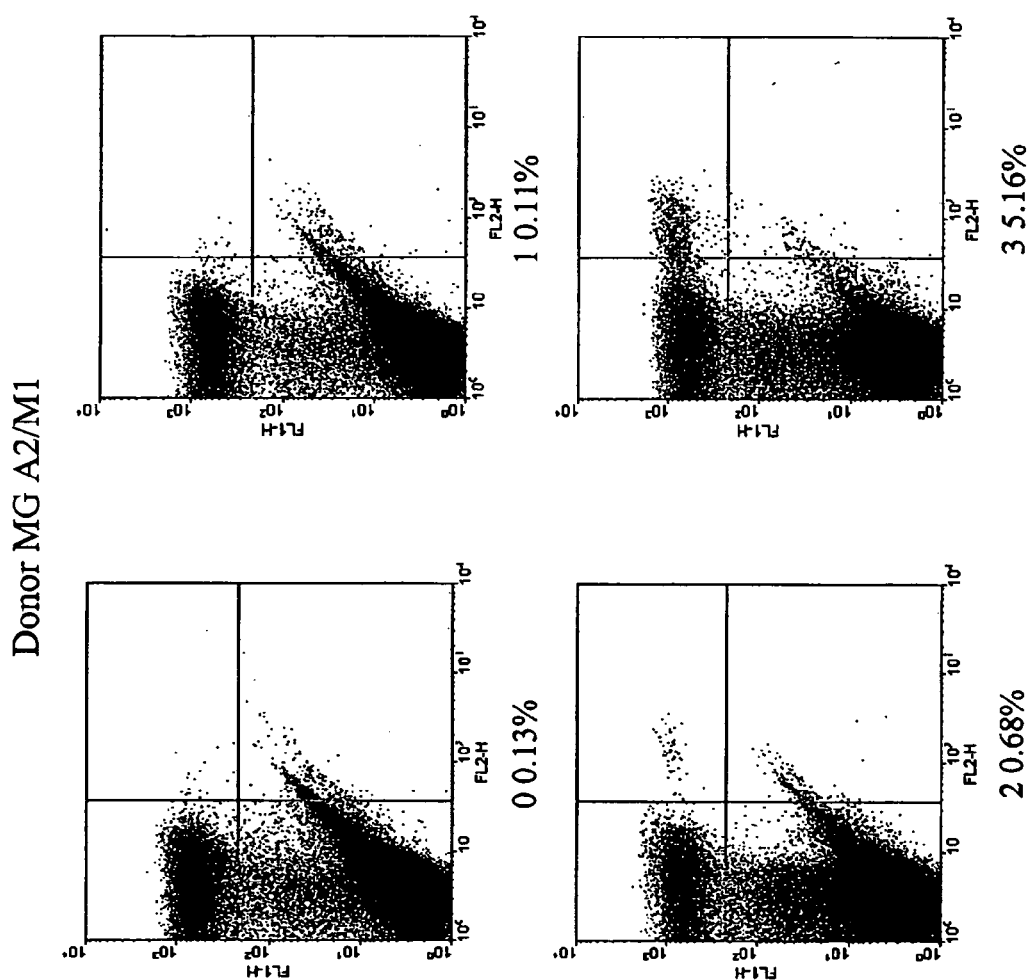

In FIGS. 23a and 23b, the tetramer staining results of PBMCs from Donor MG (HLA A1, A1, B08, B44) targeted with HLA-A2/Melan-A and HLA-A2/M1 complexes are demonstrated. These show increases in the number of HLA-A2/Melan-A tetramer positive CD8+ve cells from 0.12% prestimulation, through to 15.1% after 3 cycles. The results for HLA-A2/M1 are similar increasing from a background level of 0.13% through to 5.16% after 3 cycles.

In Table 14, the results from Donor PS (HLA A3, A24, B35, B57) and Donor BQ (HLA A1, A26, B7, B27) are included. These demonstrate similar levels of CTL production to the more stable HLA-A2/M1 and Melan-A complexes with an approximately 10 fold lower level of CTL production to the less stable HLA-A2/WT1 complex.

TABLE 14

Frequencies of tetramer positive alloreactive CTLs to HLA-A2/M1/Melan-A/WT1 before and after 1-4 cycles of stimulation with targeted HLA-A2/peptide complexes.

| Donor (#cycles) | HLA-A2/M1 | HLA-A2/Melan-A | HLA-A2/WT1 |
|---|---|---|---|
| MG (×3) | 5.2% | 14.9% | — |
| BQ (×5) | 3.1% (×3) | 22.8% (×5) | 0.74% (×5) |
| PS (×4) | — | 15.9% | 0.8% |
| LH (×3) | — | 0.5% | 1.4% |

Example 9.2

Specificity of Tetramer Staining of Alloreactive CTLs from HLA-A2 −ve Donors

Figure 24:
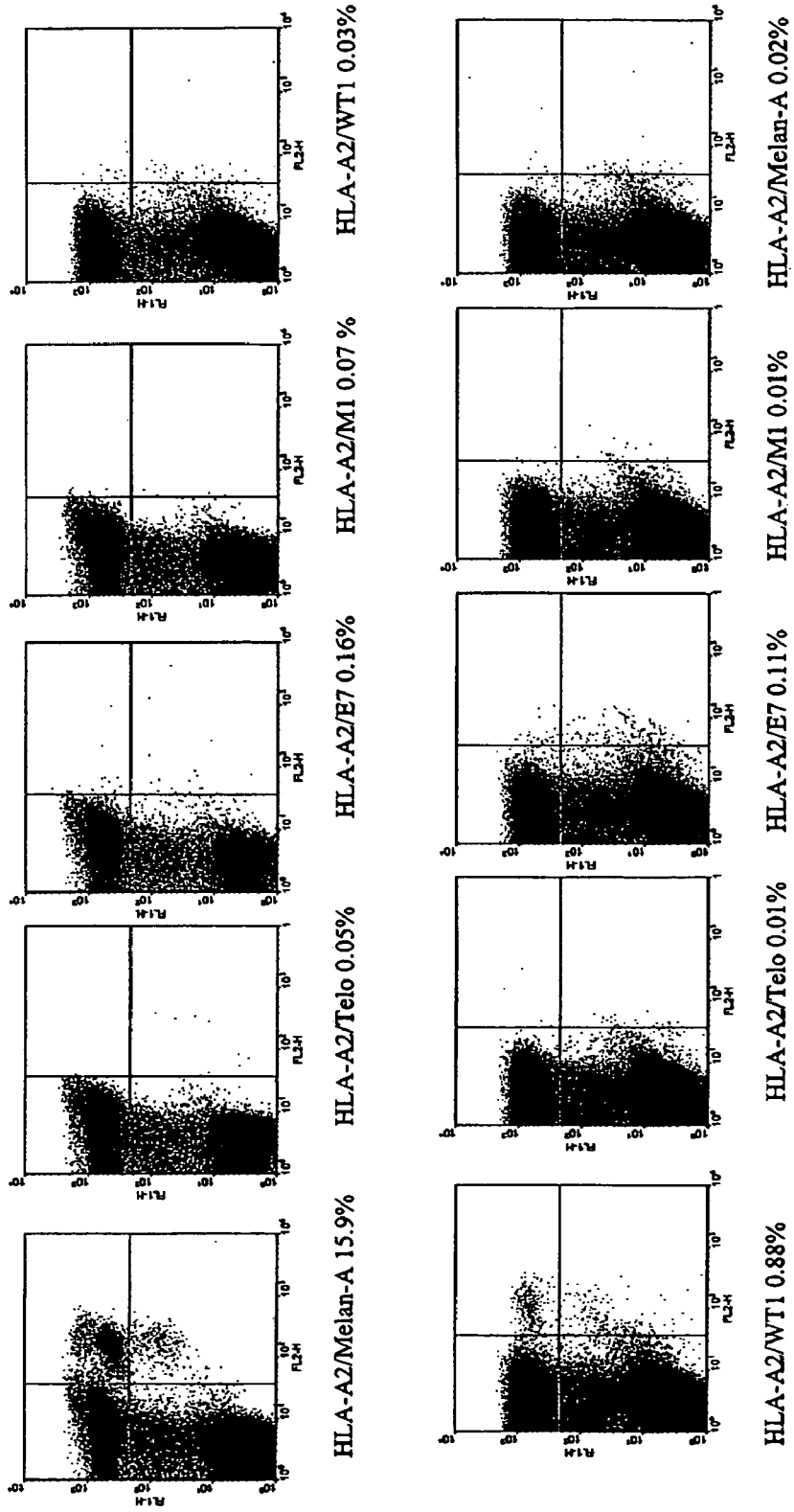
FIG. 24 shows Donor PS Tetramer analysis of CTLs produced with targeted HLA-A2/Melan-A and HLA-A2/WT1 complexes. Staining of both PBMC groups with a panel of 5 HLA-A2 tetramers demonstrates significant staining only with the appropriate tetramer.

The tetramer binding characteristics of the CTLs produced using the targeted HLA-A2 peptide/complexes were investigated with panel of 5 HLA-A2/peptide tetramers. The results from Donor PS, shown in FIG. 24, demonstrate that cells produced against both HLA-A2/Melan-A and HLA-A2/WT1 show significant staining only against the appropriate tetramer. In contrast, Donor BQ gives a different result. FIG. 8 shows that the CTLs produced from Donor BQ with HLA-A2/Melan-A show significant staining with only that tetramer, while the CTLs produced with HLA-A2/WT1 show similar levels (~0.90%) of staining with all 5 tetramers.

PBMCs stained prior to stimulation or after 3-4 cycles of cytokine treatment alone showed staining to all tetramers of <0.15%.

Example 9.3

Functional Activity of Alloreactive CTLs from HLA-A2 –ve Donors

Figure 26A:
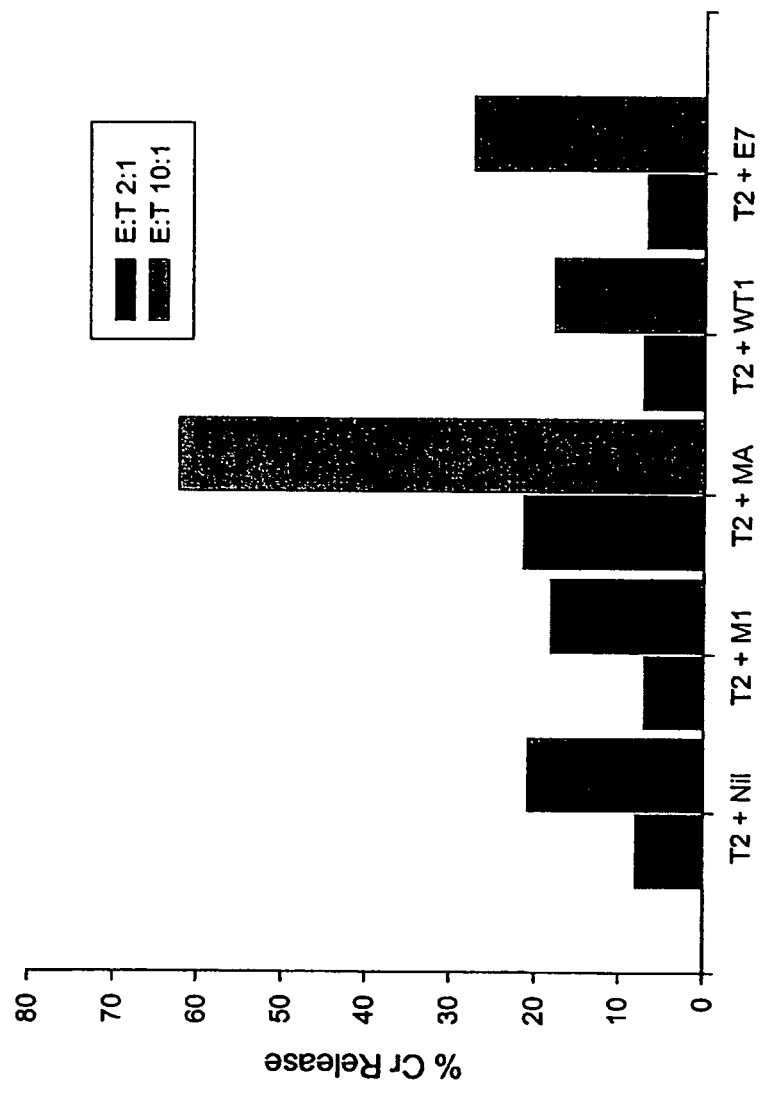
FIG. 26 shows donor PS 4 hr Chromiuim (Cr) release assays using PBMCs targeted with 4 cycles of HLA-A2/Melan-A (26a) or 4 cycles of HLA-A2/WT1 (26b) tested against native and peptide pulsed T2 cells. Both groups of PBMCs show significant peptide specificity towards the immunising peptide complex.
Figure 26B:
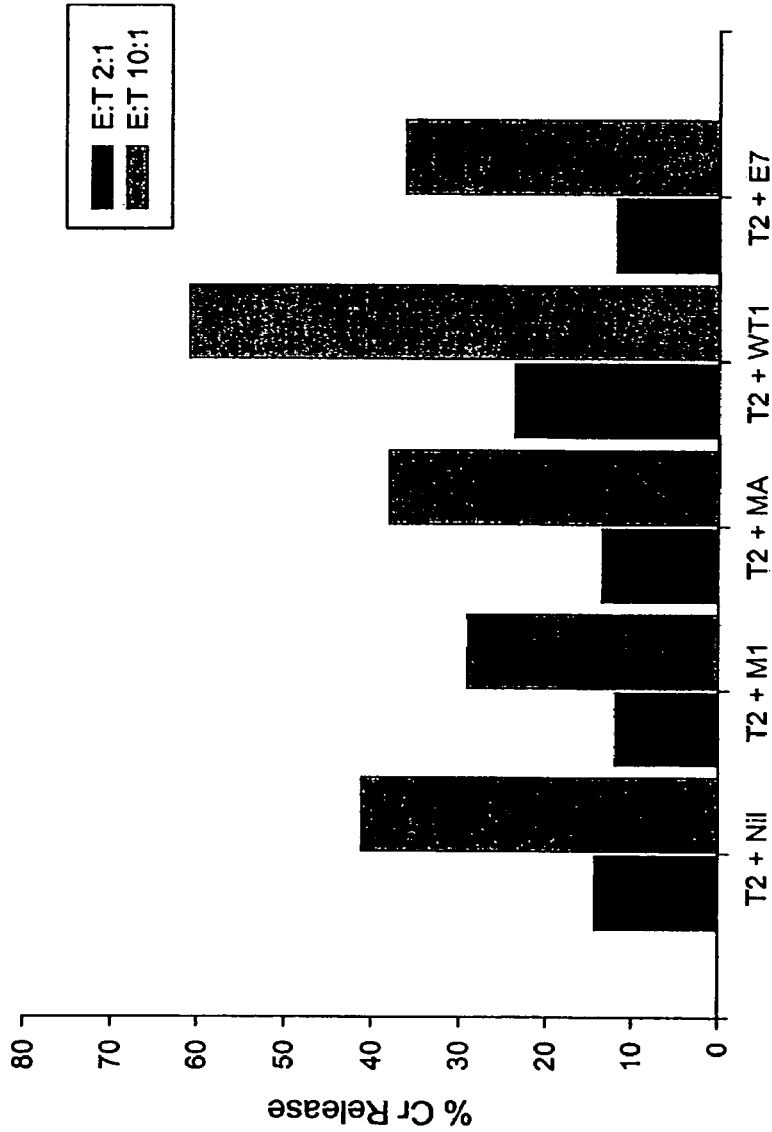

The functional activity of the alloreactive CTLs contained within the PBMCs stimulated with targeted HLA-A2/peptide complexes was investigated in standard 4 hour Cr release assays using native and peptide pulsed HLA-A2+ve T2 target cells. The results from Donor PS are shown in FIGS. 26a and 26b. The cells produced with the HLA-A2/Melan-A complex demonstrated a degree of functional specificity producing, at an E:T ratio of 10:1, 62% lysis of the T2 cells pulsed with the Melan-A peptide and from the control T2 cells a maximum lysis of 27%. Similar results are seen with CTLs produced with HLA-A2/WT1 with 61% lysis of the WT1 pulsed cells with levels of 29-41% seen for control T2 cells.

Control mock targeted PBMCs treated with weekly cycles of the anti-CD20 sfvSA antibody, cytokines but without HLA-A2/peptide complexes showed approximately 20% lysis of each of the peptide pulsed T2 cells at an E:T ratio of 10:1.

Figure 27A:
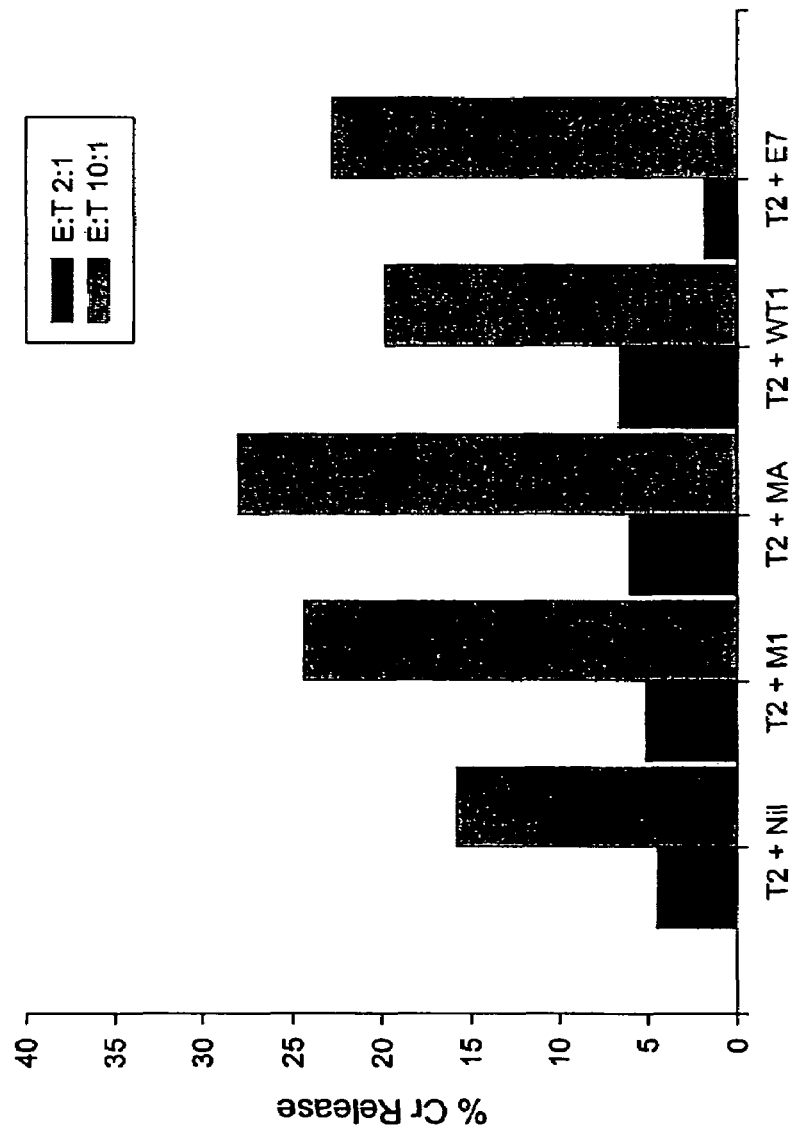
FIG. 27A-B shows donor BQ 4 hour Cr release assays using PBMCs targeted with 4 cycles of HLA-A2/Melan-A (27a) or 4 cycles of HLA-A2/WT1 (27b) tested against native and peptide pulsed T2 cells. The cells from the HLA-A2/Melan-A PBMCs show a small degree of peptide specificity, while the HLA-A2/WT1 PBMCs show no significant lysis of any of the T2 cells.
Figure 27B:
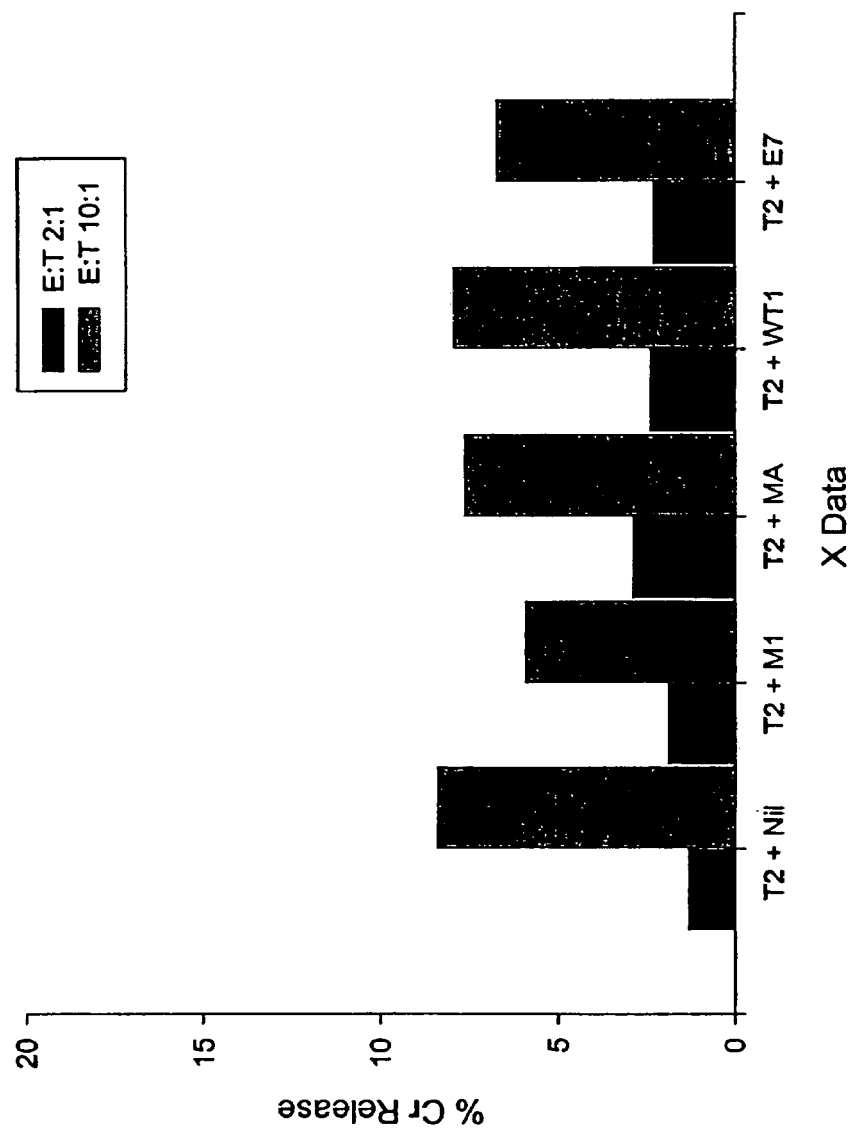

In FIG. 27a and 27b the functional results of the alloreactive CTLs contained within the PBMCs from donor BQ are shown. The cells produced with HLA-A2/Melan-A show their highest activity of 28% against the Melan-A pulsed targets compared to a maximum of 24% with the other peptides. The cells produced with HLA-A2/WT1 demonstrate no peptide specificity with activity levels equivalent to the control mock targeted CTLs.

Summary

The ability to generate CTLs that have specificity for tumour cells as demonstrated herein is of enormous potential value in haematology and cancer immunotherapy.

In this Example, HLA-A2/peptide complexes are targeted to the surface of B cells of HLA-A2 –ve donors producing a powerful alloreactive stimulus to a single designated HLA class I/peptide combination. The ability of this system to quickly and simply produce large numbers of alloreactive CTLs is demonstrated in FIG. 23a and 23b. Here for HLA-A2/Melan-A, a background level of 0.12% prior to stimulation rising to 0.13%, 0.66%, and 15.1% after 1, 2 and 3 rounds of stimulation is demonstrated. Similar results producing CTLs with the HLA-A2/M1 complex are demonstrated in FIG. 23b with 5.16% of the CD8+ve cells tetramer positive after 3 cycles of stimulation. These results compare positively with conventional T2 based technologies that produced 0.06% CD8+ve CTLs to HLA-A2/M1 after 10 days (Moris et al 2001). In Table 14, the additional results of further tetramer analyses of CTLs produced to these epitopes and to HLA-A2/WT1 in two other donors are shown.

The stability of the HLA class I/peptide complex has been shown to be important in the induction of CTL in vitro (Valmori 1999, Micheletti 1999). The results here of CTL production via the alloreactive route suggest a similar effect with more rapid and higher levels of CTL production to the more stable complexes HLA-A2/M1 and HLA-A2/Melan-A, which score 30 and 28 on the SYFPEITHI (SEQ ID NO: 10) database, compared to HLA-A2/WT1 which scores only 22 (Rammensee 1999). Preferably, peptides used in the present invention have high stability as assessed by this technique.

Figure 25:
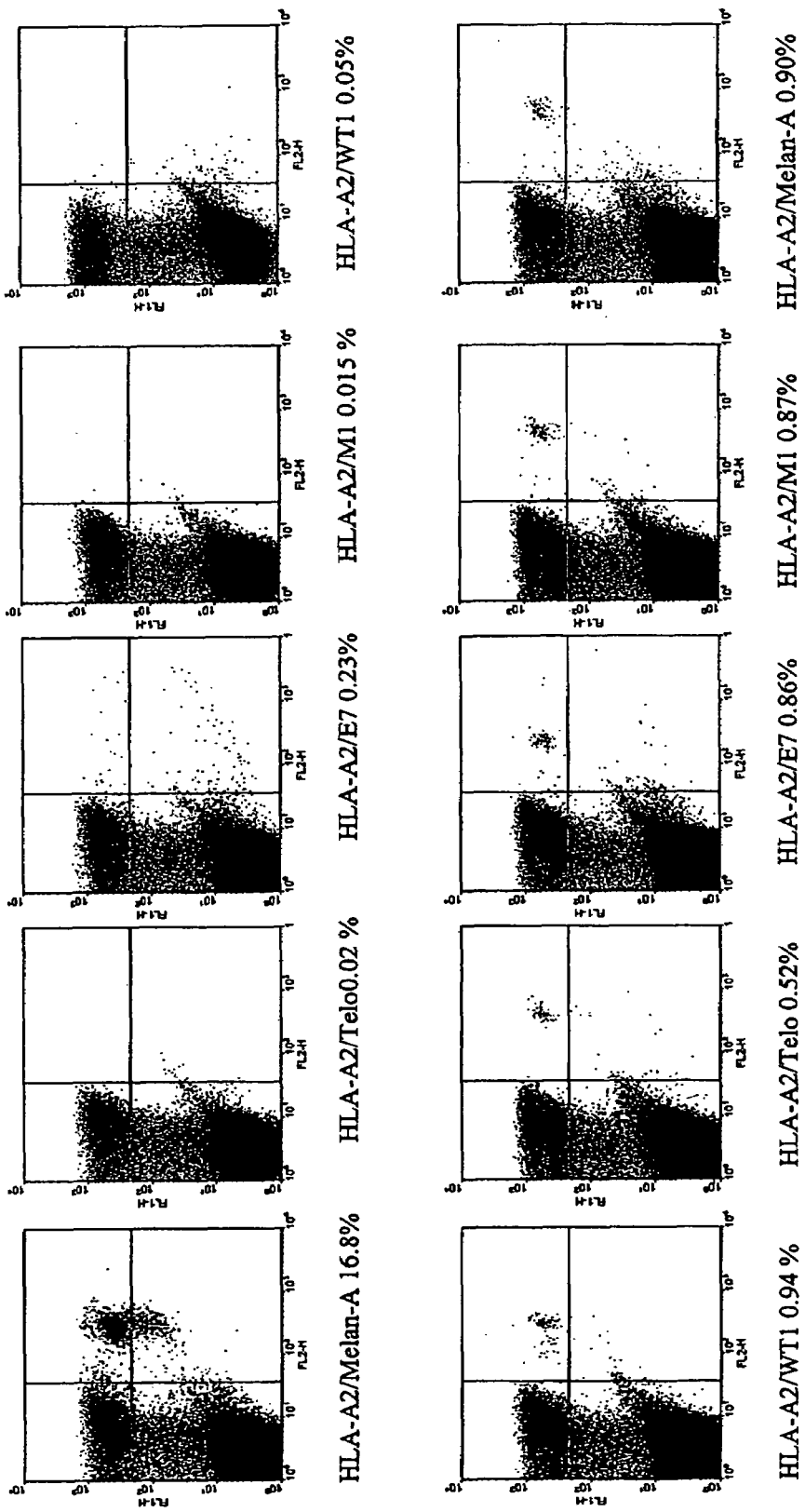
FIG. 25 shows Donor BQ Tetramer analysis of CTLs produced with targeted HLA-A2/Melan-A and HLA-A2/WT1 complexes. Staining of the HLA-A2/Melan-A PBMCs with the panel of 5 HLA-A2 tetramers demonstrates significant staining only with the appropriate tetramer. Staining of the HLA-A2/WT1 PBMCs demonstrate similar levels of staining with all 5 tetramers.

The specificity characteristics of the alloreactive. CTLs produced were investigated by staining with a panel of HLA-A2 tetramers. In FIG. 25, the results demonstrate that the CTLs produced from donor PS using targeted HLA-A2/MelanA and HLA-A2/WT1 complexes showed only significant staining with the appropriate tetramer, with no increase in the staining with the other tetramers (HLA-A2/M1/Telo/E7). The results of the functional T2 cell chromium release assays parallel the tetramer staining with a significant degree of peptide specificity for the cells produced from donor PS to HLA-A2/MelanA (62% vs 18-27%) and HLA-A2/WT1 (61% vs 29-41%).

Similar tetramer results were shown with the CTLs from Donor BQ using targeted HLA-A2/Melan-A, however with targeted HLA-A2/WT1 the PBMCs contain populations of CD8+ve cells that stain with all 5 tetramers examined. From Donor BQ, a potential degree of functional specificity for the cells to HLA-A2/Melan-A is apparent (28% vs 15-24%), however the cells produced with HLA-A2/WT1 showed no significant increase in lysis of any of the T2 cells compared to the background level of mock targeted cells.

Without being bound by theory, the detailed interpretation of these functional Cr release assays may be limited by the advantageously simple nature of the in vitro stimulation procedure of the present invention which uses unfractionated PBMCs. As a result, the bulk cell culture may contain other cell types in addition to CD8+ve CTLs and from the cytokine exposure some may possibly have some non-specific lytic activity. It is also theoretically possible that the bulk population, even from Donor PS, may contain populations of alloreactive that can recognise A2 targets but may not bind specific tetramers.

This example demonstrates that the use of targeted HLA class I/peptide complexes according to the present invention is a simple and powerful method for generating alloreactive CTLs. From the three donors investigated in this example, it is also apparent that targeted HLA class I/peptide complex can produce mixed populations of alloreactive CTLs, including those that may be peptide specific, as judged by tetramer staining and functional assays, cells that may recognise HLA-A2 with any peptide, and potentially a population of non-tetramer staining cells that may recognise HLA-A2 with any peptide. These results are in keeping with the previous observations of the width of the alloreactive response to single epitope stimulation (Sadovnikova 1998, Moris et al. 2001, Dutoit 2002)

This example also demonstrates that alloreactive CTL induction with a single HLA class I/peptide complex advantageously produce either completely or predominantly peptide specific CTLs. However, from some donors there may possibly be produced a proportion of peptide non-specific cells. Without being bound by theory, it is possible that these in vitro results could be a parallel to the situations that occur in vivo in bone marrow allograft patients. Here these differing responses could represent the extremes of beneficial graft versus leukaemia as in the PS donor and broad non-specific graft versus host disease as with the BQ donor response to HLA-A2/WT1. Nevertheless, checking the quality and form of the response is easily accomplished as shown herein, so that only suitable CTLs are infused into subjects according to the present invention.

The systems of the present invention could serve as screening approaches to indicate which allograft donor recipient mismatches are likely to produce a predominant graft versus leukaemia effect with minimised graft versus host disease. Using the HLA class I/peptide targeted B cells in vivo post transplant may advantageously also lead to the selective expansion of CTLs that recognise leukaemic cells without producing GVHD.

For tumour immunotherapy with either adoptive transfer of CTLs or TCR mediated gene therapy the requirement is the production of alloreactive CTLs that are peptide specific. As this example demonstrates, the present invention provides such CTLs and methods for making them.

REFERENCES

Dutoit V, Guillaume P, Romero P, Cerottini J-C, and Valmori D (2002) Functional analysis of HLA-A*0201/Melan-A peptide multimer+CD8+T cells isolated from an HLA-A*0201-donor: exploring tumor antigen allorestricted recognition *Cancer Immunity* 2; 7-19.

Gao L, Bellantuono I, Elsasser A, Marley S B, Gordon M Y, Goldman J M, Stauss H J (2000) Selective elimination of leukemic CD34(+) progenitor cells by cytotoxic T lymphocytes specific for WT1. *Blood* 95:2198-203

Gotch F, Rothbard J, Howland K, Townsend A, McMichael A (1987) Cytotoxic T lymphocytes recognize a fragment of influenza virus matrix protein in association with HLA-A2. *Nature* 326: 881-882

Kessels H W, Wolkers M C, van den Boom M D, van der Valk M A, Schumacher T N (2001) Immunotherapy through TCR gene transfer. Nat Immunol 2: 957-61

Lalvani A, Dong L, Ogg G, Pathan A A, Newell H, Hill A V S, McMichael A J and Rowland-Jones S (1997) Optimisation of a peptide-based protocol employing IL-7 for in vitro restimulation of human cytotoxic T lymphocyte precursors. *J Imm Methods* 210: 65-77

Micheletti F, Bazzaro M, Canella A, Marastoni M, Traniello S and Gavioli R (1999) The lifespan of major histocompatability complex ca1ssI/peptide complexes determines the efficiency of cytotoxic T lymphocyte responses. *Immunology* 96: 411-415

Minev B, Hipp J, Firat H, Schmidt J D, Langlade-Demoyen P, Zanetti M (2000). Cytotoxic T cell immunity against telomerase reverse transcriptase in humans. *Proc Natl Acad Sci USA* 97: 4796-801

Molldrem J J, Lee P P, Wang C, Felio K, Kantarjian H M, Champlin R E, Davis M M (2000) Evidence that specific T lymphocytes may participate in the elimination of chronic myelogenous leukemia. *Nat Med* 6:1018-23

Moris, A., Teichgraber, V., Gauthier, L., Buhring, H-J. and Rammensee H-G. (2001) Cutting edge: Characterization of Allorestricted and peptide-selective alloreactive T cells using HLA-tetramer selection. *J of Immunol* 166: 4818-4821.

Oka Y, Udaka K, Tsuboi A, Elisseeva O A, Ogawa H, Aozasa K, Kishimoto T, Sugiyama H (2000). Cancer immunotherapy targeting Wilms' tumor gene WT1 product *J Immunol* 164: 1873-80

Pardoll D M (2000) Therapeutic vaccination for cancer. *Clin Immunol* 95: S44-62

Pittet M, Valmori D, Dunbar P R, Speiser D E, Lienard D, Lejeune F, Fleischhauer K, Cerundolo V, Cerottini J-C and Romero P (1999) High frequencies of naïve Melan-A/Mart-1 specific CD8+ T cells in a large proportion of human histocompatability leukocyte antigen (HLA)-A2 individuals. *J Exp Med* 190: 705-716

Rammensee H-G, Bachmann J, Emmerich N N, Bachor O A, Stevanovic S (1999) SYFPEITHI: database for MHC ligands and peptide motifs. *Immunogenetics* 50: 213-219.

Ressing M E, Sette A, Brandt R M, Ruppert J, Wentworth P A, Hartman M, Oseroff C, Grey H M, Melief C J, Kast W M (1995). Human CTL epitopes encoded by human papillomavirus type 16 E6 and E7 identified through in vivo and in vitro immunogenicity studies of HLA-A*0201-binding peptides. *J Immunol* 154: 5934-43

Rosenberg S A (1996) Development of cancer immunotherapies based on identification of the genes encoding cancer regression antigens. *J Natl Cancer Inst* 88: 1635-1644

Sadovnikova E, Jopling L A, Soo K S, Stauss H J (1998). Generation of human tumor-reactive cytotoxic T cells against peptides presented by non-self HLA class I molecules. *Eur J Immunol* 28: 193-200.

Salter R D, Cresswell P (1986). Impaired assembly and transport of HLA-A and -B antigens in a mutant T×B cell hybrid. *EMBO J* 5: 943-9

Savage P, Cowburn P, Clayton A, Man S, McMichael A, Lemoine N, Epenetos A, Ogg G (2002). Induction of viral and tumour specific CTL responses using antibody targeted HLA class I peptide complexes. *Br J Cancer* 86: 1336-42

Schultz J, Lin Y, Sanderson J, Zuo Y, Stone D, Mallett R, Wilbert S and Axworthy D (2000) A tetravalent single-chain antibody-streptavidin fusion protein for pretargeted lymphoma therapy. *Cancer Res* 60: 6663-6669.

Stanislawski T, Voss R H, Lotz C, Sadovnikova E, Willemsen R A, Kuball J, Ruppert T, Bolhuis R L, Melief C J, Huber C, Stauss H J, Theobald M (2001). Circumventing tolerance to a human MDM2-derived tumor antigen by TCR gene transfer. *Nat Immunol* 2: 962-70

Valmori D, Fonteneau J-F, Lizana C M, Gervois N, Lienard D, Rimoldi D, Jongeneel V, Jotereau F, Cerottini J-C and Romero P (1998). Enhanced generation of specific tumour reactive CTL in vitro by selected Melan-A/MART-1 immunodominant peptide analogues. *J Immunol* 160: 1750-1758

All publications mentioned in the above specification are herein incorporated by reference. Various modifications and variations of the described methods and systems of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in immunology, biochemistry and biotechnology or related fields are intended to be within the scope of the following claims.

I claim:
1. A method for expanding cytotoxic T lymphocytes (CTLs) recognizing a designated HLA class I-peptide combination comprising:
(a) attaching to antigen presenting cells (APCs), in a sample of peripheral blood lymphocytes (PBLs), a complex, wherein the complex comprises an HLA class I molecule or fragment thereof having a peptide binding groove, a recognition peptide, and attachment means comprising a linking polypeptide with high specific affinity for an antigen presenting cell specific molecule on the surface of the antigen presenting cell for selectively attaching said HLA class I molecule or fragment thereof to the APC, and wherein the said HLA class I molecule or fragment thereof is bound or is attached to a recognition peptide in the peptide binding groove of the HLA class I molecule or fragment thereof, and is arranged to be presented by said HLA class I molecule or fragment thereof for T cell recognition, and the HLA class I molecule or fragment thereof comprises a T cell binding portion, and the attaching comprises the steps of:
  (i) introducing onto the surface of the APC the attachment means; followed by,
  (ii) introducing onto the surface of the APC said the class I HLA molecule or fragment thereof and a recognition peptide;
(b) optionally removing excess attachment means or class I HLA molecule or fragment thereof and recognition peptide; and
(c) optionally incubating with one or more proliferative cytokines;
whereby said cytotoxic T lymphocytes in a population of peripheral blood lymphocytes are expanded.

2. The method according to claim 1, wherein the APC is a B-cell.

3. The method according to claim 1, wherein the attachment means selectively binds to a B cell.

4. The method according to claim 1, wherein the attachment means comprises a single chain sfvSA to CD20 or CD19.

5. The method according to claim 1, wherein the peptide is a tumour peptide.

6. The method according to claim 5, wherein the tumour peptide is selected from the group consisting of a Melan-A, a WT1 and a telomerase peptide.

7. The method according to claim 1, wherein the proliferative cytokines are IL-7 and IL-2.

8. The method according to claim 1, wherein the incubation is about 7 days.

9. The method according to claim 8, wherein the incubation step is repeated for about 7 days further.

* * * * *